US008476288B2

(12) United States Patent
Bennett et al.

(10) Patent No.: US 8,476,288 B2

(45) Date of Patent: Jul. 2, 2013

(54) SALTS 756

(75) Inventors: Nicholas James Bennett, Leicestershire (GB); Thomas McInally, Leicestershire (GB); Austen Pimm, Leicestershire (GB); Yoshiaki Isobe, Osaka (JP)

(73) Assignees: AstraZeneca AB, Sodertalje (SE); Dainippon Sumitomo Pharma Co., Ltd., Osaka (JP)

(*) Notice: Subject to any disclaimer, the term of this patent is extended or adjusted under 35 U.S.C. 154(b) by 451 days.

(21) Appl. No.: 12/784,226

(22) Filed: May 20, 2010

(65) Prior Publication Data

US 2010/0298364 A1 Nov. 25, 2010

(30) Foreign Application Priority Data

May 21, 2009 (GB) .................................. 0908772.7

(51) Int. Cl.
*A61K 31/505* (2006.01)
*C07D 239/48* (2006.01)

(52) U.S. Cl.
USPC .......................................... 514/275; 544/325

(58) Field of Classification Search
USPC .......................................... 514/275; 544/325
See application file for complete search history.

(56) References Cited

U.S. PATENT DOCUMENTS 4,179,562 A 12/1979 Ponsford
4,689,338 A 8/1987 Gerster
4,698,348 A 10/1987 Gerster
4,714,701 A 12/1987 Beauchamp
4,912,112 A 3/1990 Seydel et al.
5,736,549 A 4/1998 Beasley et al.
5,994,361 A 11/1999 Penney et al.
6,028,076 A 2/2000 Hirota et al.
6,110,923 A 8/2000 Ely
6,329,381 B1 12/2001 Kurimoto et al.
6,376,501 B1 4/2002 Isobe et al.
6,458,798 B1 10/2002 Fujita et al.
6,951,866 B2 10/2005 Fujita et al.
7,157,465 B2 1/2007 Isobe et al.
8,012,964 B2 9/2011 Kurimoto et al.
8,268,990 B2 * 9/2012 Bennett et al. .................... 540/1
2002/0128264 A1 9/2002 Taylor
2003/0191086 A1 10/2003 Hanus
2004/0214192 A1 10/2004 Hashida et al.
2005/0054590 A1 3/2005 Averett
2005/0119273 A1 6/2005 Lipford et al.
2006/0052403 A1 3/2006 Isobe et al.
2007/0190071 A1 8/2007 Kurimoto et al.
2007/0225303 A1 9/2007 Ogita et al.
2008/0269240 A1 10/2008 Hashimoto et al.
2008/0300244 A1 12/2008 Bonnert et al.
2009/0082332 A1 3/2009 Abbot et al.
2009/0099216 A1 4/2009 Millichip et al.
2009/0105212 A1 4/2009 Isobe et al.
2009/0118263 A1 5/2009 Hashimoto et al.
2009/0143400 A1 6/2009 McInally et al.
2009/0192153 A1 7/2009 Hashimoto et al.
2009/0209524 A1 8/2009 Bennett et al.
2009/0264447 A1 10/2009 Dietz et al.
2010/0087443 A1 4/2010 Bonnert et al.
2010/0093998 A1 4/2010 Isobe et al.
2010/0099870 A1 4/2010 Isobe et al.
2010/0130491 A1 5/2010 Bonnert et al.
2010/0240623 A1 9/2010 Cook et al.
2010/0280001 A1 11/2010 Bonnert et al.
2011/0028715 A1 2/2011 Isobe et al.
2011/0046369 A1 2/2011 Hashimoto et al.
2011/0054168 A1 3/2011 Kurimoto et al.
2011/0136801 A1 6/2011 Isobe et al.

FOREIGN PATENT DOCUMENTS

| | | |
|---|---|---|
| EP | 1550662 | 7/2005 |
| EP | 1728793 | 12/2006 |
| EP | 2246353 | 11/2010 |
| GB | 1375162 | 11/1974 |
| JP | 08-165292 | 6/1996 |
| JP | 347422/1997 | 11/1997 |
| JP | 367449/1997 | 12/1997 |
| JP | 367451/1997 | 12/1997 |
| JP | 11-193282 | 7/1999 |
| WO | WO 98/01448 | 1/1998 |
| WO | WO 99/28321 | 6/1999 |
| WO | WO 99/32122 | 7/1999 |
| WO | WO 99/50249 | 10/1999 |
| WO | WO 01/07027 | 2/2001 |
| WO | WO 02/04449 | 1/2002 |
| WO | WO 2004/029054 | 4/2004 |
| WO | WO 2005/009978 | 2/2005 |
| WO | WO 2005/092892 | 10/2005 |
| WO | WO 2005/092893 | 10/2005 |
| WO | WO 2006/137706 | 12/2006 |
| WO | WO 2007/031726 | 3/2007 |
| WO | WO 2007/031829 | 3/2007 |
| WO | WO 2007/034173 | 3/2007 |

(Continued)

OTHER PUBLICATIONS

Byrn et al., Solid-State Chemistry of Drugs, 1999, SSCI, Inc., Second Edition, pp. 62-63.*
Newman et al., Solid-state analysis of the active pharmaceutical ingredient in drug products, DDT, vol. 8, No. 19, Oct. 2003, pp. 898-905.*
Chawla et al., Challenges in Polymorphism of Pharmaceuticals, CRIPS, vol. 5, No. 1, Jan.-Mar. 2004, pp. 9-12.*
Brittain et al., Polymorphism in Pharmaceutical Solids, 1995, vol. 95, p. 228-229.*
Aoki et al., "Weekly dosing of AZD8848/DSP-3025, a novel TLR7 agonist antedrug, demonstrates a prolonged period of control against markers of pulmonary inflammation in an alergen challenge model in the mouse," ATS, New Orleans, May 2010.

(Continued)

*Primary Examiner* — Kristin Bianchi
(74) *Attorney, Agent, or Firm* — Morgan Lewis Bockius LLP

(57) ABSTRACT

The invention provides salts of 4-(dimethylamino)butyl 2-(4-((2-amino-4-methyl-6-(pentylamino)pyrimidin-5-yl)methyl)phenyl)acetate, pharmaceutical compositions containing them and their use in therapy.

35 Claims, 25 Drawing Sheets

FOREIGN PATENT DOCUMENTS

| | | |
|---|---|---|
| WO | WO 2007/034817 | 3/2007 |
| WO | WO 2007/034881 | 3/2007 |
| WO | WO 2007/034882 | 3/2007 |
| WO | WO 2007/034916 | 3/2007 |
| WO | WO 2007/034917 | 3/2007 |
| WO | WO 2008/001070 | 1/2008 |
| WO | WO 2008/004948 | 1/2008 |
| WO | WO 2008/015250 | 2/2008 |
| WO | WO 2008/083465 | 7/2008 |
| WO | WO 2008/114006 | 9/2008 |
| WO | WO 2008/114008 | 9/2008 |
| WO | WO 2008/114817 | 9/2008 |
| WO | WO 2008/114819 | 9/2008 |
| WO | WO 2008/135791 | 11/2008 |
| WO | WO 2009/067081 | 5/2009 |
| WO | WO 2009/078798 | 6/2009 |
| WO | WO 2009/091031 | 7/2009 |
| WO | WO 2009/091032 | 7/2009 |
| WO | WO 2010/033074 | 3/2010 |

OTHER PUBLICATIONS

Bell et al., "AZD8848/DSP-3025, a novel potent TLR7 agonist antedrug, demonstrates negligible systemic activity and a prolonged period of control after cessation of weekly dosing in a brown Norway rat ovalbumin challenge model," ATS, New Orleans, May 2010.
Biffen et al., "Biological activity of a novel TLR7 agaonist antedrug for the treatment of allergic diseases," ATS, New Orleans, May 2010.
Falco et al., "2,4-Diaminopyrimidines as Antimalarials. I.1 5-Aryloxyl and 5-Alkoxyl Derivatives," J. Am. Chem. Soc., 73 (8): 3753-3758 (1951).
Ikeda et al., "AZD8848/DSP-3025, a novel potent TLR7 agonist antedrug, demonstrates efficacy against airway obstruction and other inflammatory endpoint in Guinea pig models of Rhinitis and asthma with acute and weekly dosing," ATS, New Orleans, May 2010.
Kurimoto et al. "Synthesis and biological evaluation of novel 9-substituted-8-hydroxyadenine derivatives as potent interferon inducers" Journal of Medicinal Chemistry 49(6): 2088-2095 (2006).
Kurimoto et al., "Synthesis and biological evaluation of 8-oxoadenine derivatives as Toll-like Receptor 7 agonists introducing the antedrug concept," J. Med. Chem., 2010, 53, pp. 2964-2972.
Lee et al. "Activation of anti-hepatitis C virus responses via Toll-like receptor 7" Proc. Natl. Acad. Sci. USA 103(6): 1828-1833 (2006).
Matsui et al., "Mechanisms of inhibition of type-2 Cytokines by novel TLR7 agonist antedrugs," ATS New Orleans, May 2010.
Mclnally et al, "Identification of a novel TLR7 agonist antedrug," EFMC-ISMC 201, Brussels, Belgium, Sep. 5-9, 2010.
Mclnally, "Identification and pharmacology of novel TLR7 agonist antedrugs," RSC BMSC Inflammation meeting Nov. 18, 2010.
Tojo et al., "Synthesis and biological evaluation of a novel TLR7 agonist with an antedrug strategy," EFMC-ISMC 201, Brussels, Belgium, Sep. 5-9, 2010.
Yoshimoto et al., "ation analysis of Baker's studies on enzyme inhibition. 2. Chymotrypsin, trypsin, thymidine phosphorylase, uridine phosphorylase, thymidylate synthetase, cytosine nucleoside deaminase, dihydrofolate reductase, malate dehydrogenase, glutamate dehydrogenase, lactate dehydrogenase, and glyceraldehyde-phosphate dehydrogenase," J. Med. Chem., 19(1): 71-98 (1976).
English translation of Opposition against Costa Rican Patent Application No. 11451, 2010.
Biffen et al. "Novel TLR7 agonists for the treatment of allergic diseases," Toll 2011 Meeting, Riva del Garda, Italy, May 4-7, 2011, Abstract.
Eiho et al. "Mechanism of long-lasting suppression against Th2 immune response in the lung by a novel antedrug TLR7 agonist," European Respiratory Society Annual Congress, Amsterdam, Sep. 24-28, 2011, Abstract and Poster.
Greiff et al. "Repeated intranasal TLR7 stimulation reduces allergen responsiveness in allergic rhinitis," European Respiratory Society Annual Congress, Amsterdam, Sep. 24-28, 2011, Abstract and Poster.
Hirota et al. "Discovery of 8-hydroxydenines as a novel type of interferon inducer" J. Med. Chem. 45(25):5419-5422 (2002).
Isobe et al. "Synthesis and biological evaluation of novel 9-substituted-8-hydroxyadenine derivatives as potent interferon inducers" J. Med. Chem. 49(6):2088-2095 (2006).
Isobe et al. "Synthesis and structure-activity relationships of 2-substituted-8-hydroxyadenine derivatives as orally available interferon inducers without emetic side effects" Bioorganic & Medicinal Chemistry 11:3641-3647 (2003).
Kurimoto et al. "Prodrugs of 9-benzyl-8-hydroxy-2-(2-hydroxyethylthio)adenine: Potent interferon inducing agents in monkeys" Chemical and Pharmaceutical Bulletin 52(4):466-469 (2004).
Kurimoto et al. "Synthesis and evaluation of 2-substituted 8-hydroxyadenines as potent interferon inducers with improved oral bioavailabilities" Bioorganic & Medicinal Chemistry 12:1091-1099 (2004).
Kurimoto et al. "Synthesis and structure-activity relationships of 2-amino-8-hydroxyadenines as orally active interferon inducing agents" Bioorganic & Medicinal Chemistry 11:5501-5508 (2003).
Lee et al. "Molecular basis for the immunostimulatory activity of guanine nucleoside analogs: Activation of Toll-like receptor 7" Proc. Natl. Acad. Sci. USA 100(11):6646-6651 (2003).
Nichol et al. "Stimulation of murine interferon by a substituted pyrimidine" Antimicrobial Agents and Chemotherapy 9(3):433-439 (1976).
Reiter et al. "Cytokine induction in mice by the immunomodulator imiquimod" Journal of Leukocyte Biology 55(2):234-240 (1994).
Stringfellow et al. "Antiviral and interferon-inducing properties of 1,5-diamino anthraquinones" Antimicrobial Agents and Chemotherapy 15(1):111-118 (1979).

* cited by examiner

SALTS 756

This application claims the benefit under 35 U.S.C. §119 (a)-(d) of Application No. 0908772.7 (GB) filed on 21 May 2009.

NAMES OF PARTIES TO A JOINT RESEARCH AGREEMENT

The subject matter claimed in this application was made as a result of activities undertaken within the scope of a joint research agreement dated Dec. 19, 2003, between AstraZeneca AB and Sumitomo Pharmaceuticals Co., Ltd. All of the rights and obligations of Sumitomo Pharmaceuticals Co., Ltd. as defined in the joint research agreement between AstraZeneca AB and Sumitomo Pharmaceuticals Co., Ltd. were assumed by Dainippon Sumitomo Pharma Co., Ltd., a company created by the merger of Dainippon Pharmaceuticals Co., Ltd. and Sumitomo Pharmaceuticals Co., Ltd. effective Oct. 3, 2005.

FIELD OF THE INVENTION

The present invention relates to salts of pyrimidine derivatives, pharmaceutical compositions containing them and their use in therapy.

BACKGROUND OF THE INVENTION

The immune system is comprised of innate and acquired immunity, both of which work cooperatively to protect the host from microbial infections. It has been shown that innate immunity can recognize conserved pathogen-associated molecular patterns through toll-like receptors (TLRs) expressed on the cell surface of immune cells. Recognition of invading pathogens then triggers cytokine production (including interferon alpha (IFNα)) and upregulation of co-stimulatory molecules on phagocytes, leading to modulation of is T cell function. Thus, innate immunity is closely linked to acquired immunity and can influence the development and regulation of an acquired response.

TLRs are a family of type I transmembrane receptors characterized by an $NH_2$-terminal extracellular leucine-rich repeat domain (LRR) and a COOH-terminal intracellular tail containing a conserved region called the Toll/IL-1 receptor (TIR) homology domain. The extracellular domain contains a varying number of LRR, which are thought to be involved in ligand binding. Eleven TLRs have been described to date in humans and mice. They differ from each other in ligand specificities, expression patterns, and in the target genes they can induce.

Ligands which act via TLRs (also known as immune response modifiers (IRMS)) have been developed, for example, the imidazoquinoline derivatives described in U.S. Pat. No. 4,689,338 which include the product Imiquimod for treating genital warts, and the adenine derivatives described in WO 98/01448 and WO 99/28321.

WO2009/067081 describes a class of pyrimidine derivatives having immuno-modulating properties that act via TLR7 which are useful in the treatment of viral or allergic diseases and cancers.

4-(Dimethylamino)butyl 2-(4-((2-amino-4-methyl-6-(pentylamino)pyrimidin-5-yl)methyl)phenyl)acetate and certain salts thereof are described in Example 57 of International Patent Application No. PCT/SE2008/051334 filed on 21 Nov. 2008, published as WO2009/067081.

DISCLOSURE OF THE INVENTION

Figure 1:
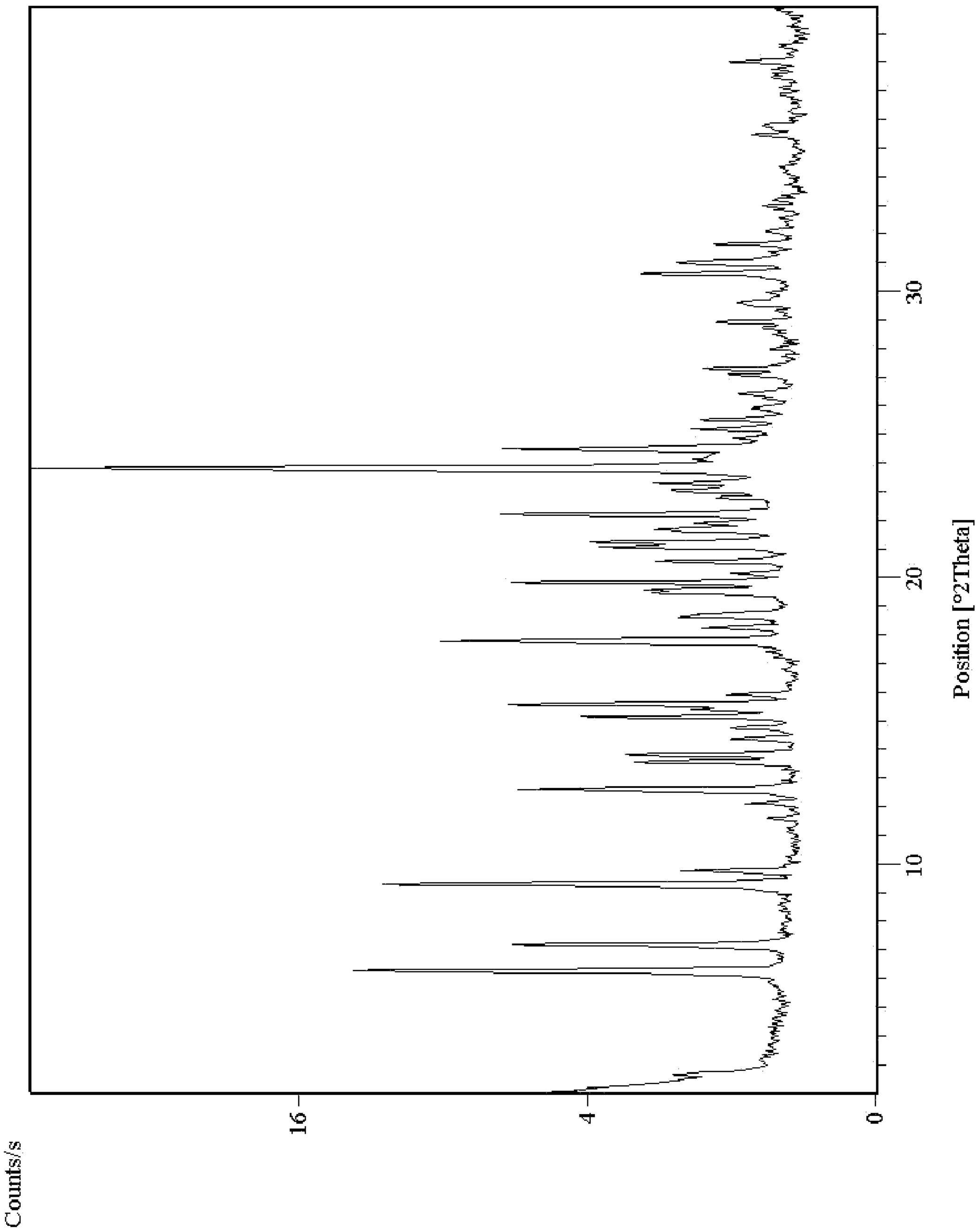
FIG. 1 shows an X-ray powder diffraction pattern of a mono-benzoic acid salt of Compound (I).

In the formulation of drug substances, it is important for the drug substance (active compound) to be in a form in which it can be conveniently handled and processed. This is of importance, not only from the point of view of obtaining a commercially-viable manufacturing process for the drug substance itself, but also from the point of view of subsequent manufacture of pharmaceutical formulations comprising the active compound and suitable excipients. In this connection, the chemical stability and the physical stability of the active compound are important factors. The active compound, and formulations containing it, should be capable of being effectively stored over appreciable periods of time, without exhibiting any significant change in the physico-chemical characteristics (e.g. chemical composition, density, hygroscopicity and solubility) of the active is compound.

Furthermore, if the active compound is to be incorporated into a formulation for pulmonary administration, e.g., via a dry powder inhaler such as the Turbuhaler® device, it is desirable if the active compound can be readily micronised to yield a powder with good flow properties and comprising a high fine particle fraction (i.e. a fraction in which the active compound particles have a mass median diameter (MMD) of less than or equal to 10 μm (micrometer)). Such a fraction is capable of being carried deep into the lungs leading to faster and increased absorption of the active compound.

The person skilled in the art will appreciate that, typically, if a drug substance can be readily obtained in a stable form, such as a stable crystalline form, advantages may be provided, in terms of ease of handling, ease of preparation and extended shelf-life of suitable pharmaceutical formulations, and a more reliable solubility profile.

It has now surprisingly been found possible to prepare certain salts of 4-(dimethylamino)butyl 2-(4-((2-amino-4-methyl-6-(pentylamino)pyrimidin-5-yl)methyl)phenyl)acetate having improved physico-chemical properties compared to the free base compound, which are capable of being formulated in a dry powder formulation for nasal/pulmonary administration.

The structure of 4-(dimethylamino)butyl 2-(4-((2-amino-4-methyl-6-(pentylamino)pyrimidin-5-yl)methyl)phenyl) acetate (hereafter "Compound (I)") is shown below:

Compound (I)

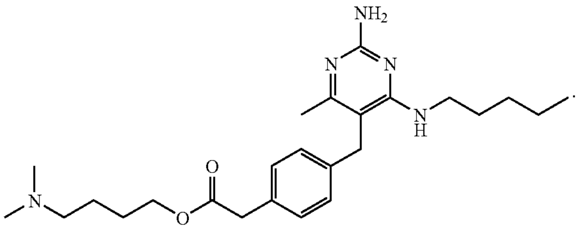

Thus, in accordance with the present invention, there is provided a benzoic acid, trans-cinnamic acid, methanesulphonic acid, disaccharin, 1-hydroxy-2-naphthoic acid, 2,5-dichlorobenzenesulphonic acid, 1,5-naphthalenedisulphonic acid, citric acid, phosphoric acid, fumaric acid, L-tartaric acid or succinic acid salt of Compound (I) (active pharmaceutical ingredient, API).

In the context of the present invention, the term "salt" defines a crystalline material in which the API and the acid are ionized or alternatively, where both components utilise prominent intermolecular interactions, such as hydrogen bonding, to combine and yield a is uniform crystalline material (a co-crystal). It will be appreciated that a salt according to the invention may be partially ionic and partially co-crystal.

In another aspect, the invention provides a benzoic acid, trans-cinnamic acid, methanesulphonic acid, disaccharin, 1-hydroxy-2-naphthoic acid, 2,5-dichlorobenzenesulphonic acid, 1,5-naphthalenedisulphonic acid, citric acid, phosphoric acid, fumaric acid, L-tartaric acid or succinic acid salt of Compound (I) which exhibits the characteristic X-ray powder diffraction peaks (expressed in degrees 2θ) as shown in the appropriate Table I to XIX in Example 20 below.

Unless stated otherwise, all of the X-ray powder diffraction data described herein was obtained using CuKα radiation as described in the Examples.

The invention also provides solvates (including hydrates) of the salts according to the invention. However, the salts according to the invention are preferably anhydrous, and are preferably in non-solvated form.

In an embodiment of the invention, the salt according to the invention or a solvate thereof has crystalline properties and is preferably at least 50% crystalline, more preferably at least 60% crystalline, still more preferably at least 70% crystalline and most preferably at least 80% crystalline. Crystallinity can be estimated by conventional X-ray diffractometry techniques.

In another embodiment of the invention, the salt or solvate thereof is from 50%, 60%, 70%, 80% or 90% to 95%, 96%, 97%, 98%, 99% or 100% crystalline.

Unless otherwise indicated, the stoichiometry of Compound (I) to acid in the salts according to the invention may vary, e.g. from 2:1 to 1:2 or any ratio in between such as 1:1. Examples of preferred salts according to the invention include the Compound (I) to acid, 1:1, salts of benzoic acid, trans-cinnamic acid, methanesulphonic acid, 2,5-dichlorobenzenesulphonic acid, 1,5-naphthalenedisulphonic acid, citric acid, phosphoric acid, fumaric acid, L-tartaric acid and succinic acid, or the Compound (I) to acid, 1:2, salts of saccharin (i.e. disaccharin), 1-hydroxy-2-naphthoic acid (i.e. di-1-hydroxy-2-naphthoic is acid), 2,5-dichlorobenzenesulphonic acid (i.e. di-(2,5-dichlorobenzenesulphonic acid)), phosphoric acid (i.e. diphosphoric acid) or succinic acid (i.e. disuccinic acid). Another suitable salt is the 1:2 salt of fumaric acid (i.e. difumaric acid).

We have surprisingly found that the disaccharin, difumaric acid, di-1-hydroxy-2-naphthoic acid and benzoic acid salts of Compound (I) exhibit good solid state chemical stability when stored under conditions of high temperature and humidity (for example 40° C. and 75% relative humidity). In addition, stability studies on mixtures of the disaccharin salt with lactose monohydrate and mixtures of the difumaric acid salt with lactose monohydrate show that these salts are also particularly stable in the presence of lactose monohydrate, a common carrier used for the formulation of drugs for inhalation. The stability of these salts is illustrated in the Examples herein. These salts are therefore expected to be advantageous because they are expected to exhibit, for example, improved storage stability.

Accordingly, in one embodiment of the invention there is provided a disaccharin, difumaric acid, di-1-hydroxy-2-naphthoic acid or benzoic acid salt of Compound (I).

In another embodiment of the invention there is provided a disaccharin, di-1-hydroxy-2-naphthoic acid or benzoic acid salt of Compound (I).

In another embodiment of the invention there is provided a disaccharin, difumaric acid or benzoic acid salt of Compound (I).

In another embodiment there is provided a disaccharin or difumaric acid salt of Compound (I).

Disaccharin Salts of Compound (I)

In another embodiment of the invention there is provided a disaccharin salt of Compound (I).

Figure 4:
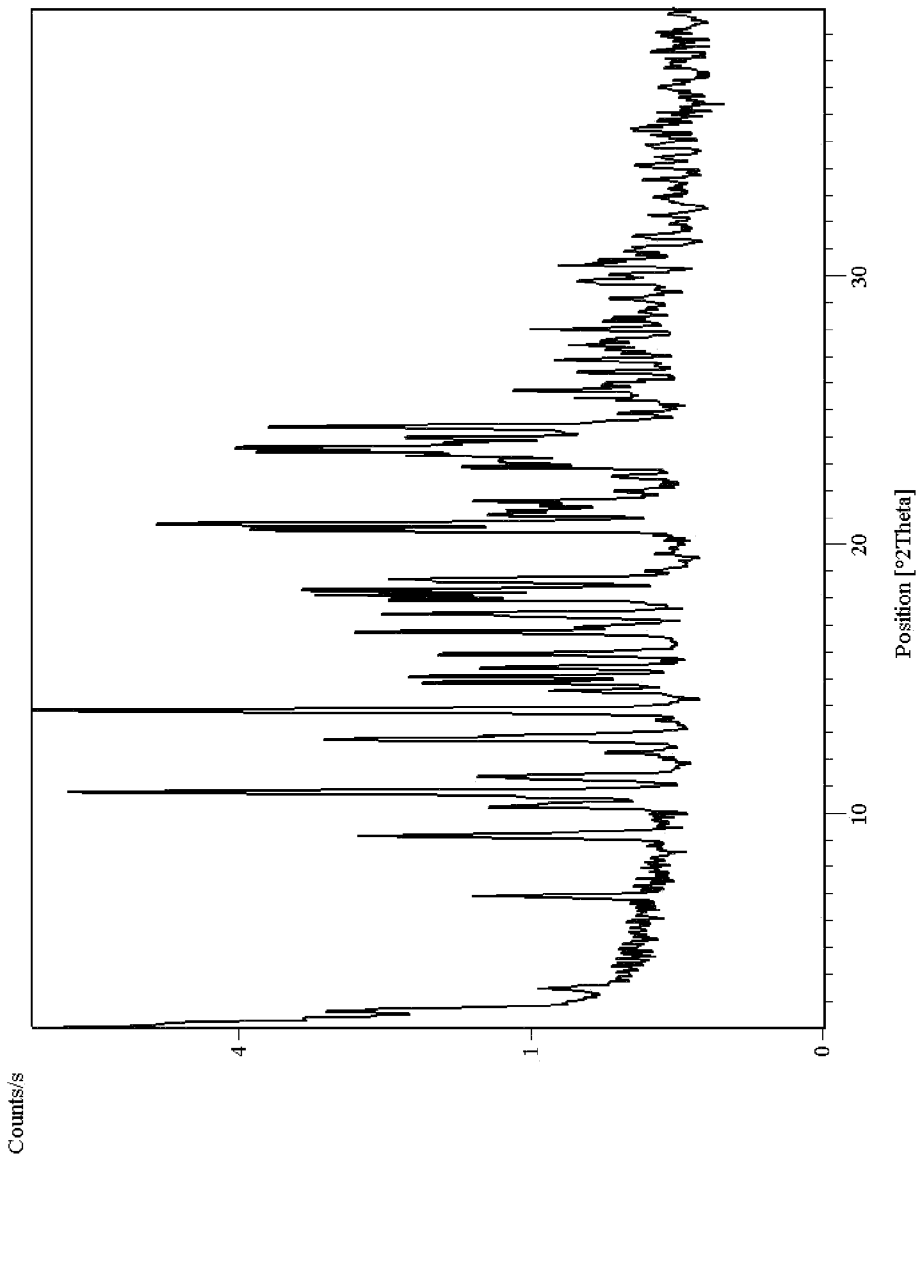
FIG. 4 shows an X-ray powder diffraction pattern of the disaccharin salt of Compound (I) (Form A).

We have found that the disaccharin salt of Compound (I) exists in a number of crystalline forms. One crystalline form of the disaccharin salt, hereafter "disaccharin salt of Compound (I) Form A" provides an X-ray powder diffraction pattern substantially as shown in FIG. 4. The most prominent peaks of Form A are shown in Table IV in the Examples. The disaccharin salt of Compound (I) Form A is thought to be the most thermodynamically stable crystalline form of this salt.

Accordingly a further aspect of the invention provides the disaccharin salt of is Compound (I) Form A.

According to a further aspect of the invention there is provided the disaccharin salt of Compound (I) Form A, characterised in that said Form A has an X-ray powder diffraction pattern with at least one specific peak at 2θ about=9.2°, 14.9° or 15.2°.

According to a further aspect of the invention there is provided the disaccharin salt of Compound (I) Form A, characterised in that said Form A has an X-ray powder diffraction pattern with at least one specific peak at 2θ about=9.2°, 10.3°, 11.4°, 12.8°, 14.9°, 15.2°, 22.9° or 23.4°.

According to a further aspect of the invention there is provided the disaccharin salt of Compound (I) Form A, characterised in that said Form A has an X-ray powder diffraction pattern with specific peaks at 2θ about=9.2°, 14.9° and 15.2°.

According to a further aspect of the invention there is provided the disaccharin salt of Compound (I) Form A, characterised in that said Form A has an X-ray powder diffraction pattern with specific peaks at 2θ about=9.2°, 10.3°, 11.4°, 12.8°, 14.9°, 15.2°, 22.9° and 23.4°.

According to a further aspect of the invention there is provided the disaccharin salt of Compound (I) Form A, characterised in that said Form A has an X-ray powder diffraction pattern substantially as shown in FIG. 4.

Figure 20:
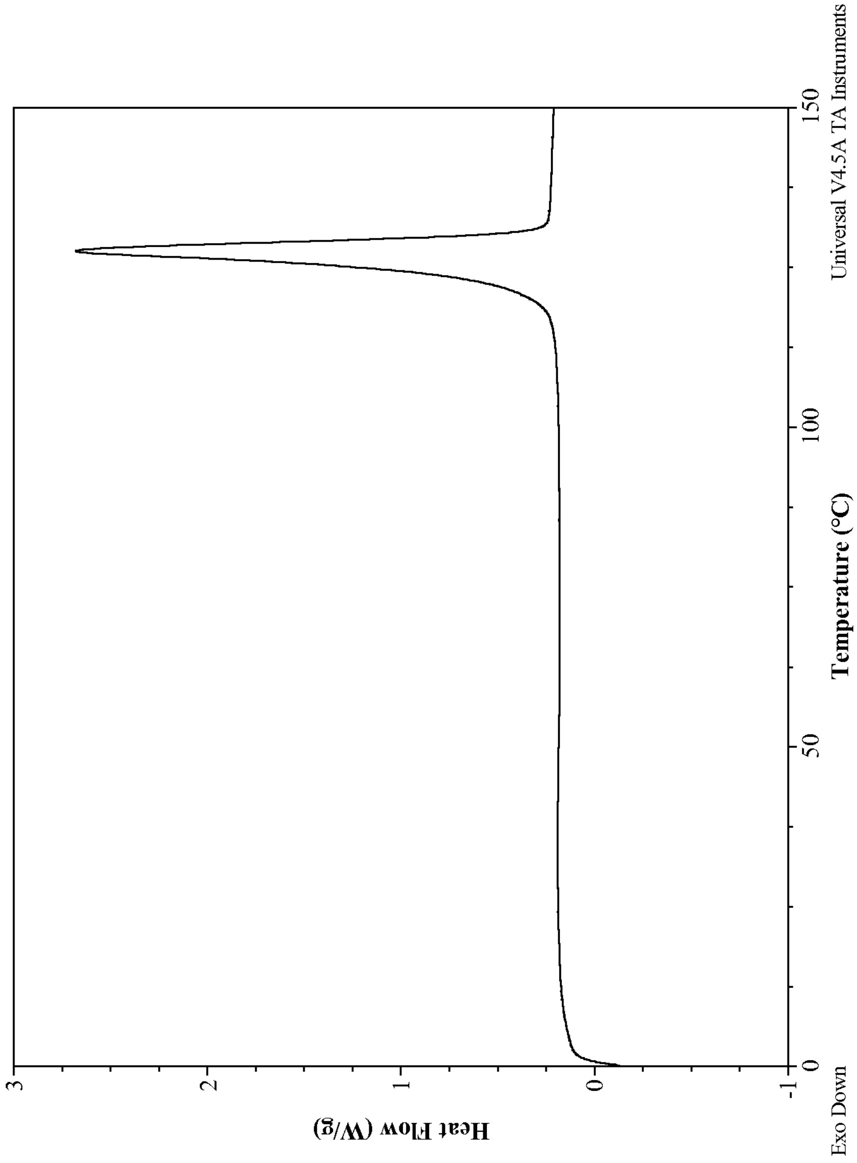
FIG. 20 shows a differential scanning calorimetry (DSC) trace for the disaccharin salt of Compound (I) Form A. The x-axis shows temperature (° C.) and the y-axis heat flow (watts/g).

When heated in a Differential Scanning Calorimeter (DSC) (conditions as described in the Examples section) the disaccharin salt of Compound (I) Form A exhibits a melting endotherm with an onset temperature at about 124° C., and a peak temperature at about 127° C. as illustrated in FIG. 20.

According to a further aspect of the invention there is provided a process for the preparation of the disaccharin salt of Compound (I) Form A comprising (i) reacting Compound (I) with approximately 2 molar equivalents of saccharin in ethyl acetate and (ii) crystallizing the said Form A.

The reaction in step (i) is suitably carried out at ambient temperature.

Crystallisation of Form A in step (ii) may occur spontaneously following the salt formation. In this case it may be necessary to stir the resulting suspension of the salt to allow full crystallisation to occur. The stirring of the salt slurry is conveniently carried out at ambient temperature. Generally stirring of the salt slurry for a few days in the ethyl acetate, for example 1 to 10 days, such as about 6 days, provides crystalline Form A.

According to a further aspect of the invention there is provided another process for the preparation of the disaccharin salt of Compound (I) Form A comprising (i) reacting Compound (I) with approximately 2 molar equivalents of saccharin in acetonitrile; (ii) concentrating the reaction mixture; and (iii) crystallizing the said Form A from ethyl acetate.

The reaction is step (i) is suitably carried out at ambient temperature.

Concentration of the mixture in step (ii) may be achieved by, for example, evaporating some or all of the acetonitrile off.

Crystallisation of Form A in step (iii) may be effected by, for example, stirring a slurry or solution of the salt in the ethyl acetate. The stirring of the salt slurry/solution is conveniently carried out at ambient temperature. Generally stirring for a few days in the ethyl acetate, suitably 1 to 10 days, for example 2 to 7 days, provides crystalline Form A.

The specific reaction conditions which resulted in the formation of the disaccharin salt of Compound (I) Form A are illustrated in the Examples.

Crystallisation of the Form A in the processes described above may be aided by seeding with crystals of the Form A. The seed crystals may be obtained using one of the methods described in the Examples. The use of seeding is particularly advantageous in larger-scale manufacture of the salt. Seeding may also allow alternative solvents and process conditions to be used to give the disaccharin salt of Compound (I) Form A.

Accordingly, in one embodiment the disaccharin salt of Compound (I) Form A is prepared by a process comprising:

(i) dissolving Compound (I) in acetonitrile and reacting with approximately 2 molar equivalents of saccharin;

(ii) adding ethyl acetate whilst maintaining the temperature of the mixture at about 40° C.;

(iii) seeding the mixture with crystals of the disaccharin salt of Compound (I) Form A;

(iv) cooling the mixture; and (v) isolating the disaccharin salt of Compound (I) Form A.

In step (ii) following seeding, the mixture is suitably stirred for a period of time to allow crystallisation, for example about 5 hours. In step (iv) the mixture is cooled to promote further crystallisation. In one embodiment the mixture is cooled to about 10 to 20° C. In one embodiment the mixture is cooled to about 20° C. In one embodiment the is mixture is cooled to about 20° C. In another embodiment the mixture is cooled in stages, first to about 35° C. and then further to about 15° C. In the first stage after cooling to about 35° C., the mixture is stirred for about 4 hours prior to cooling to about 15° C. The mixture is then suitably stirred for approximately 2 more hours prior to isolation of the Form A. Optionally, the salt may be recrystallised by dissolving the salt in acetonitrile and recrystallising by repeating steps (ii) to (v) above.

Figure 5:
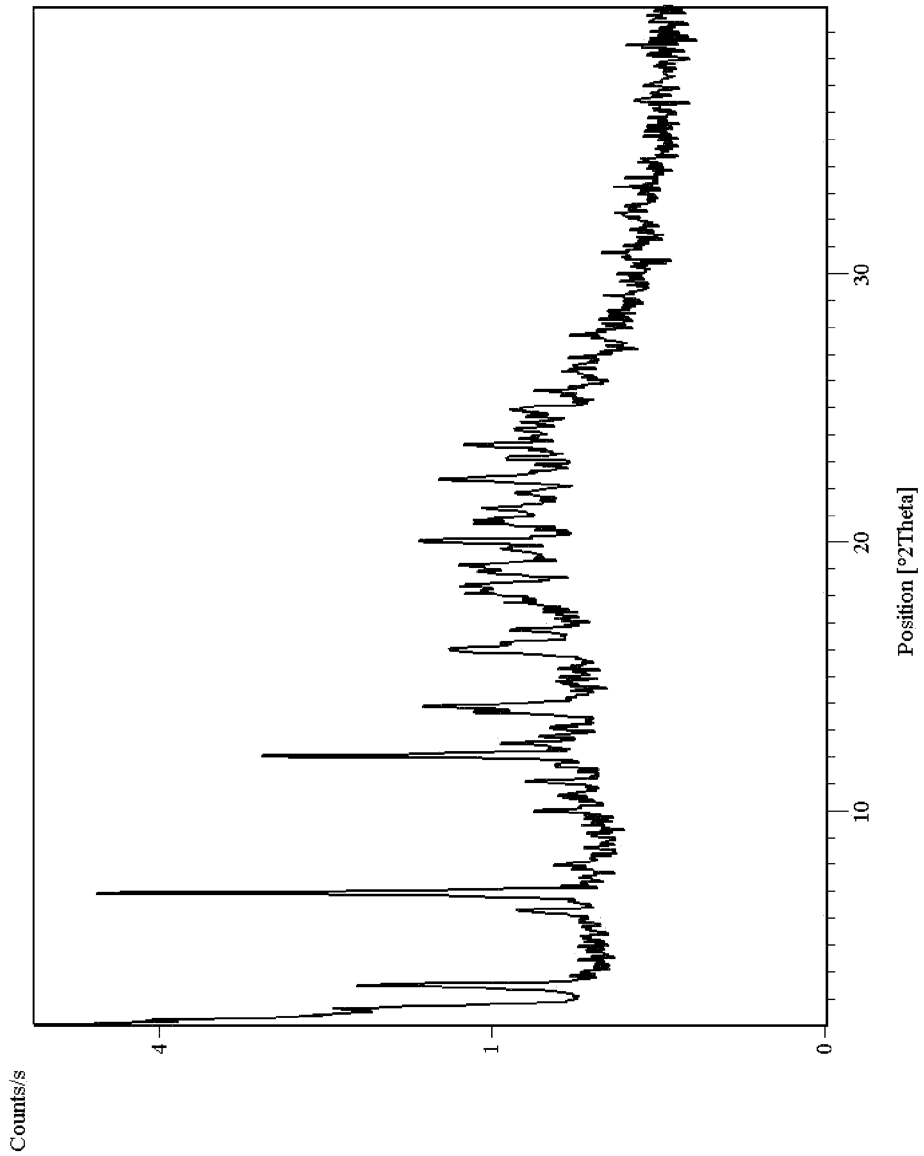
FIG. 5 shows an X-ray powder diffraction pattern of the disaccharin salt of Compound (I) (Form B).

Another crystalline form of the disaccharin salt, hereafter "disaccharin salt of Compound (I) Form B" provides an X-ray powder diffraction pattern substantially as shown in FIG. 5. The most prominent peaks of Form B are shown in Table V in the Examples.

Accordingly, a further aspect of the invention provides the disaccharin salt of Compound (I) Form B.

According to a further aspect of the invention there is provided the disaccharin salt of Compound (I) Form B, characterised in that said Form B has an X-ray powder diffraction pattern with at least one specific peak at 2θ about=12.0°, 12.5°, 16.4° or 19.8°.

According to a further aspect of the invention there is provided the disaccharin salt of Compound (I) Form B, characterised in that said Form B has an X-ray powder diffraction pattern with at least one specific peak at 2θ about=7.0°, 10.8°, 12.0°, 12.5°, 13.9°, 16.4°, 17.3° or 19.8°.

According to a further aspect of the invention there is provided the disaccharin salt of Compound (I) Form B, characterised in that said Form B has an X-ray powder diffraction pattern with specific peaks at 2θ about=12.0°, 12.5°, 16.4° and 19.8°.

According to a further aspect of the invention there is provided the disaccharin salt of Compound (I) Form B, characterised in that said Form B has an X-ray powder diffraction pattern with specific peaks at 2θ about=7.0°, 10.8°, 12.0°, 12.5°, 13.9°, 16.4°, 17.3° and 19.8°.

According to a further aspect of the invention there is provided the disaccharin salt of Compound (I) Form B, characterised in that said Form B has an X-ray powder diffraction pattern substantially as shown in FIG. 5.

Figure 21:
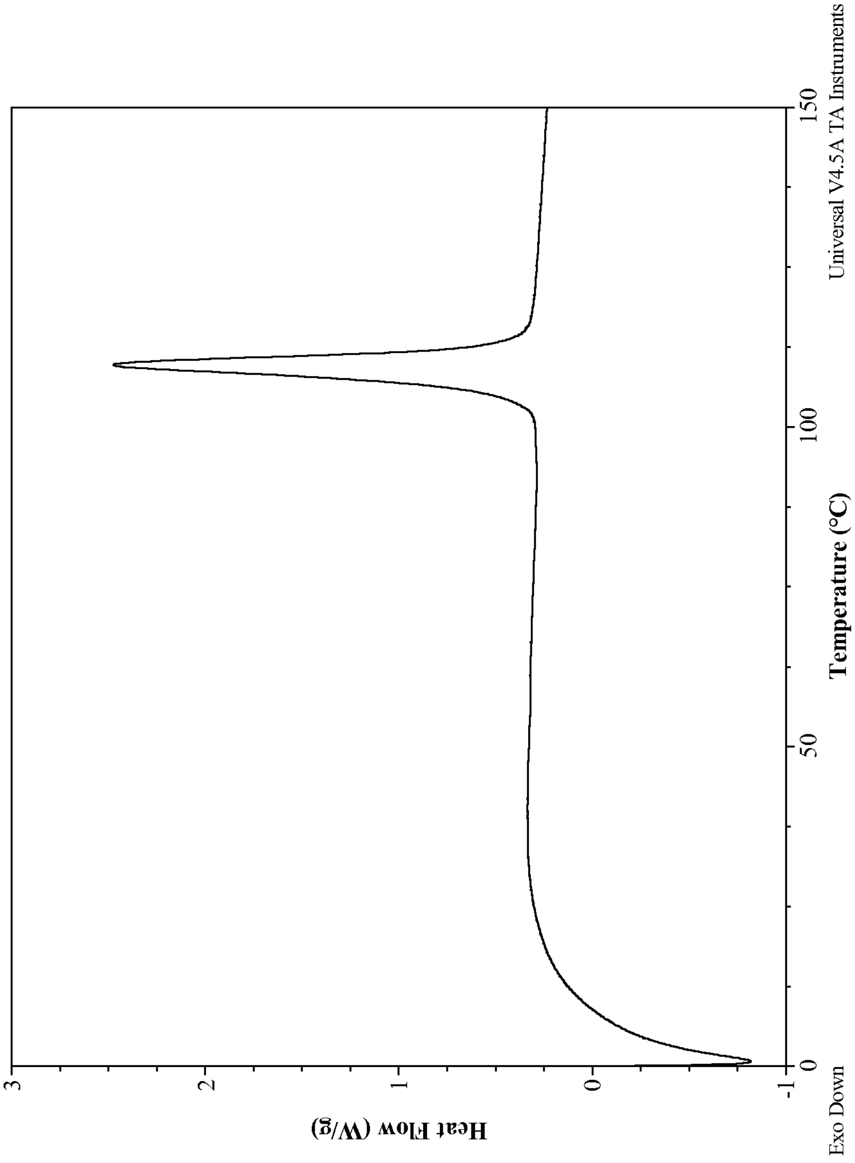
FIG. 21 shows a differential scanning calorimetry (DSC) trace for the disaccharin salt is of compound (I) Form B. The x-axis shows temperature (° C.) and the y-axis heat flow (watts/g).

When heated in a Differential Scanning Calorimeter (DSC) (conditions as described in the Examples section) the disaccharin salt of Compound (I) Form B exhibits a melting is endotherm with an onset temperature at about 106° C., and a peak temperature at about 110° C. as illustrated in FIG. 21.

The disaccharin salt of Compound (I) Form B may be prepared by a process comprising reacting Compound (I) with approximately 2 molar equivalents of saccharin in ethyl acetate or acetonitrile. The Form B is may then be crystallised from ethyl acetate using the specific conditions described in the Examples. Crystallisation of the Form B may be aided by seeding the salt slurry with crystals of the Form B. The seed crystals may be obtained using one of the methods described in the Examples.

Difumaric Acid Salt of Compound (I)

In another embodiment of the invention there is provided a difumaric acid salt of Compound (I).

Figure 19:
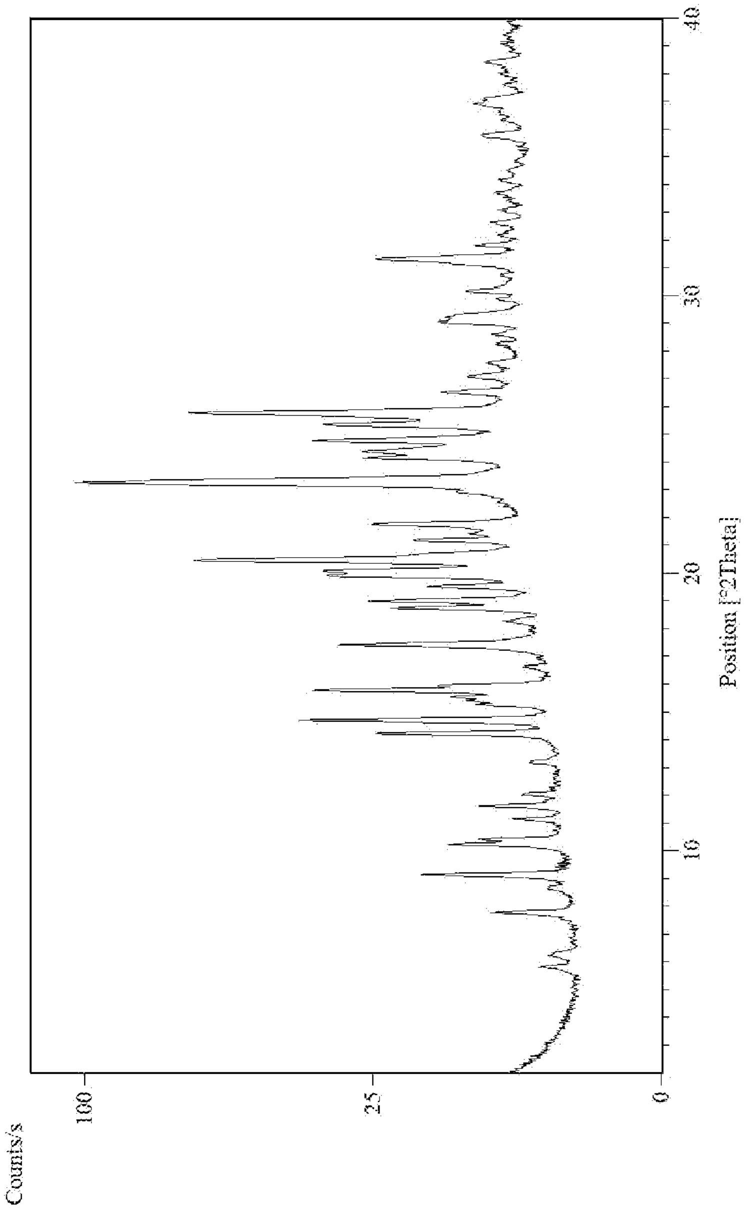
FIG. 19 shows an X-ray powder diffraction pattern of a difumarate salt of Compound (I).

The difumaric acid salt of Compound (I) is crystalline and provides an X-ray powder diffraction pattern substantially as shown in FIG. 19. The most prominent peaks of the difumaric acid salt are shown in Table XIX in the Examples.

According to a further aspect of the invention there is provided a difumaric acid salt of Compound (I), characterised in that said salt has an X-ray powder diffraction pattern with at least one specific peak at 2θ about=9.1°, 14.2°, 15.8° or 20.4°.

According to a further aspect of the invention there is provided a difumaric acid salt of Compound (I), characterised in that said salt has an X-ray powder diffraction pattern with at least one specific peak at 2θ about=7.8°, 9.1°, 14.2°, 15.8°, 18.7°, 19.0°, 20.4° or 24.7°.

According to a further aspect of the invention there is provided a difumaric acid salt of Compound (I), characterised in that said salt has an X-ray powder diffraction pattern with specific peaks at 2θ about=9.1°, 14.2°, 15.8° and 20.4°.

According to a further aspect of the invention there is provided a difumaric acid salt of Compound (I), characterised in that said salt has an X-ray powder diffraction pattern with specific peaks at 2θ about=7.8°, 9.1°, 14.2°, 15.8°, 18.7°, 19.0°, 20.4° and 24.7°.

In another embodiment there is provided a difumaric acid salt of Compound (I), characterised in that said salt has an X-ray powder diffraction pattern substantially as shown in FIG. 19.

Figure 22:
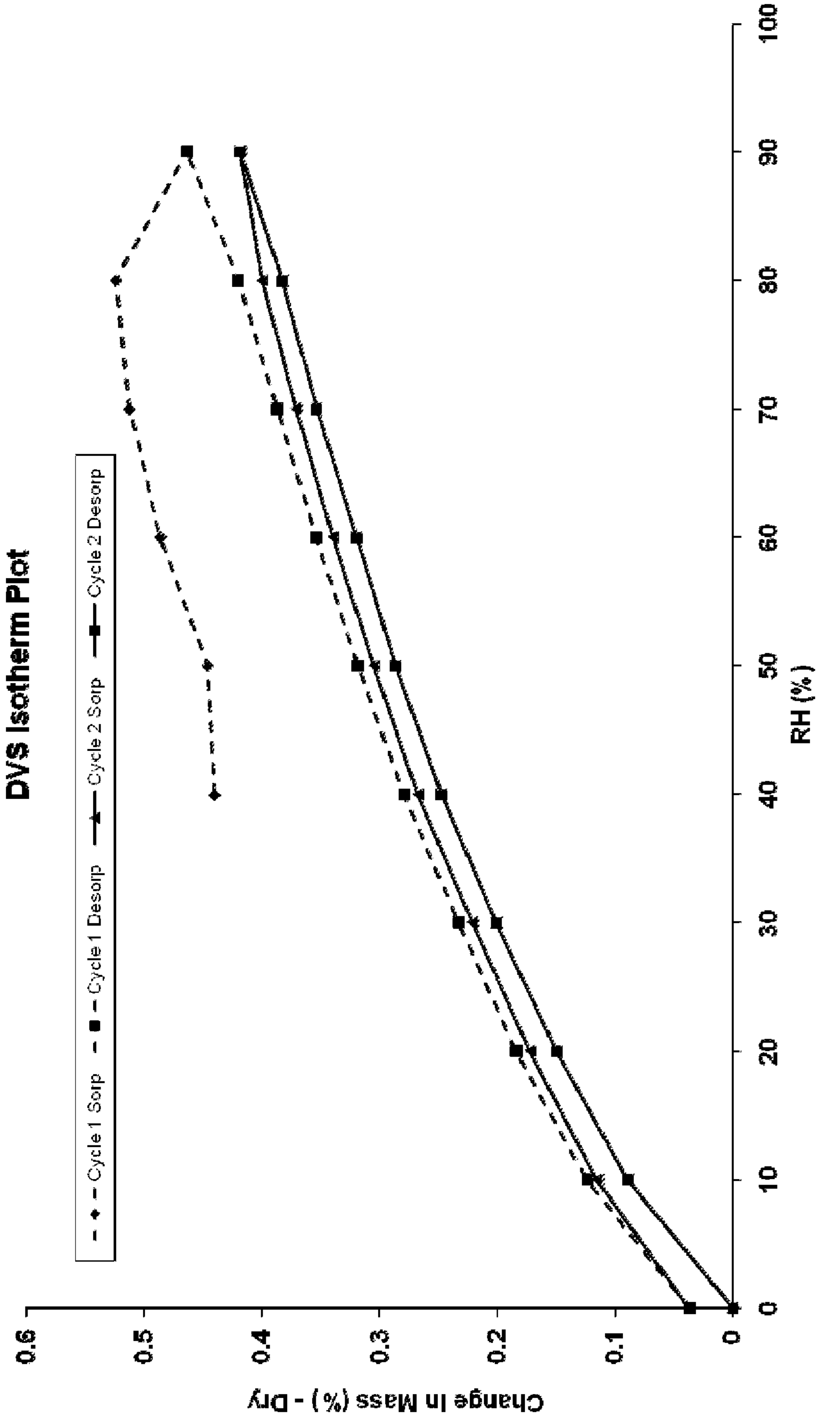
FIG. 22 shows a dynamic vapour sorption (DVS) isothermal plot for the difumaric acid salt of Compound (I). The x-axis shows the relative humidity (RH %) and the y-axis shows the change in mass of the sample.

Humidity sorption measurements using gravimetrical vapour sorption (DVS as described in the Examples Section) showed that the Compound (I) difumaric acid salt is slightly hygroscopic (0.2-2% w/w moisture uptake at 80% relative humidity, see FIG. 22).

According to a further aspect of the invention there is provided a process for the preparation of the difumaric acid salt of Compound (I) comprising (i) reacting Compound (I) with approximately 2 molar equivalents of fumaric acid in acetonitrile, or a mixture of acetonitrile and tetrahydrofuran (THF), to form the difumaric acid salt; and (ii) crystallising the difumaric acid salt from diethyl ether.

The reaction in step (i) is suitably carried out at ambient temperature. Conveniently the fumaric acid may be dissolved in THF. This solution is then added to the solution of Compound (I) in acetonitrile. Alternatively, the fumaric acid may be added to the solution of Compound (I) as a solid. Following the reaction the difumaric acid salt may be isolated by for example evaporating off the solvent(s).

The crystallisation in step (ii) is conveniently carried out by slurrying the salt in diethyl ether. Crystalline difumaric acid salt is observed after stirring the slurry at ambient temperature for a few days, for example about 5 to 7 days.

According to a further aspect of the invention there is provided a process for the preparation of the difumaric acid salt of Compound (I) comprising (i) reacting Compound (I) with approximately 2 molar equivalents of fumaric acid in ethanol; and (ii) crystallising the difumaric acid salt, for example by adding a suitable anti-solvent such as isopropyl acetate.

Crystalisation of the difumaric acid salt may be aided by seeding the mixture with crystals of the difumaric acid salt. The seed crystals may be prepared using one of the methods described in the Examples. When seeding is used to initiate crystallisation of the difumaric acid salt it may be possible to use a wider range of solvents and anti-solvents for the crystallisation. For example the difumaric acid salt could be crystallised from an alcohol such as methanol or ethanol. Conveniently, when seeding is used, the difumaric acid salt may be crystallised from methanol or ethanol using a suitable anti-solvent to effect the crystallisation. Suitable anti-solvents include, for example an ester such as isopropyl acetate. The use of an solvent/anti-solvent system such as methanol/isopropyl acetate together with seeding is expected to provide a convenient method for the preparation of the difumaric acid salt on a large scale. Accordingly in one embodiment the difumaric acid salt is prepared by a process comprising:

(i) dissolving Compound (I) in ethanol and reacting with approximately 2 molar equivalents of fumaric acid;

(ii) adding isopropyl acetate whilst maintaining the temperature of the mixture at about 30° C.;

(iii) seeding the mixture with crystals of the difumaric acid salt of Compound (I);

(iv) adding further isopropyl acetate and cooling the mixture to about 20° C.; and (v) isolating the difumaric acid salt of Compound (I).

Suitably in step (i) the compound (I) is dissolved in about 6 volume ratios of the ethanol. In step (ii) suitably about a 2.8 volume ratio of isopropyl acetate is added to the mixture. In step (iii) the mixture is suitably stirred for about 2.5 hours following seeding to allow crystallisation to occur. In step (iv) suitably about a 3.2 volume ratio of isopropyl acetate is added to the mixture. The mixture is then suitably stirred for about 1 hour.

Di-1-hydroxy-2-naphthoic acid Salt of Compound (I)

In another embodiment of the invention there is provided a di-1-hydroxy-2-naphthoic acid salt of Compound (I).

Figure 6:
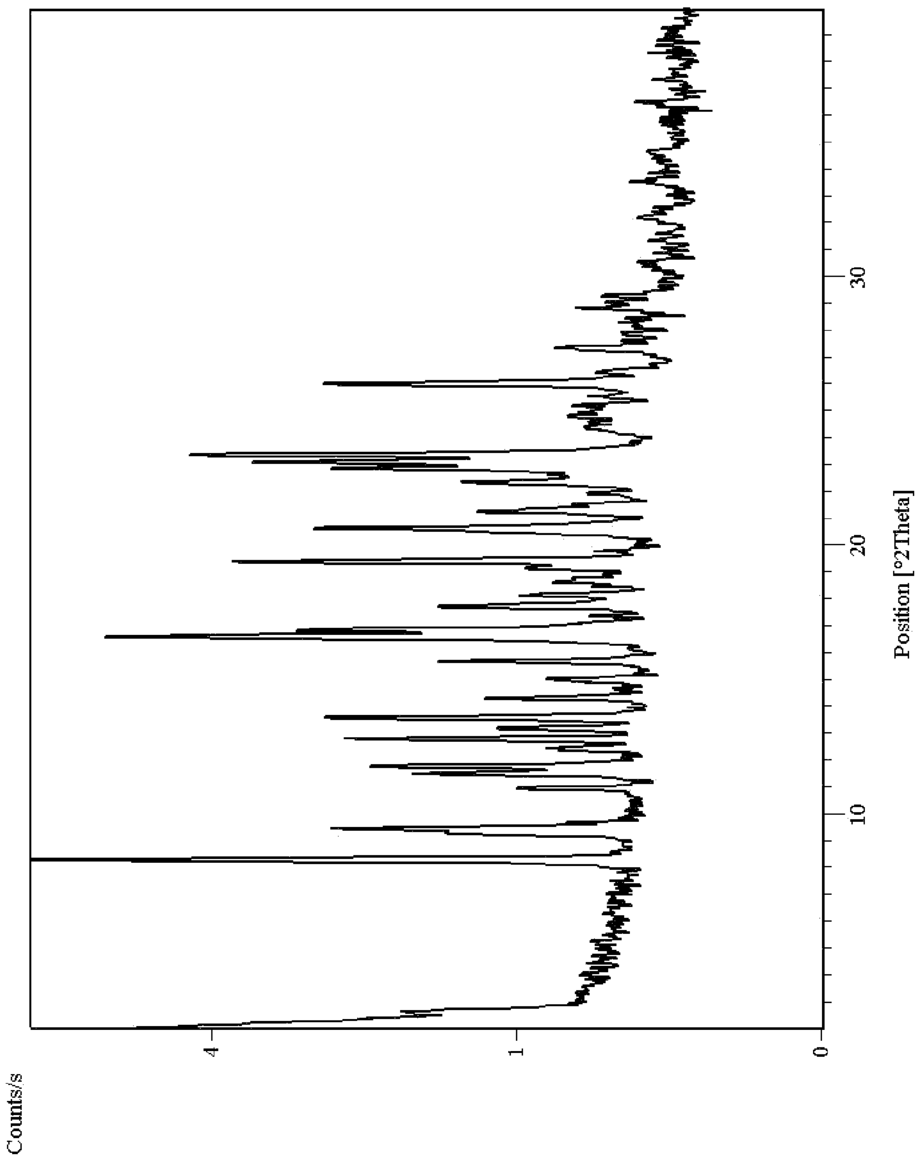
FIG. 6 shows an X-ray powder diffraction pattern of a di-(1-hydroxy-2-naphthoic is acid) salt of Compound (I).
Figure 7:
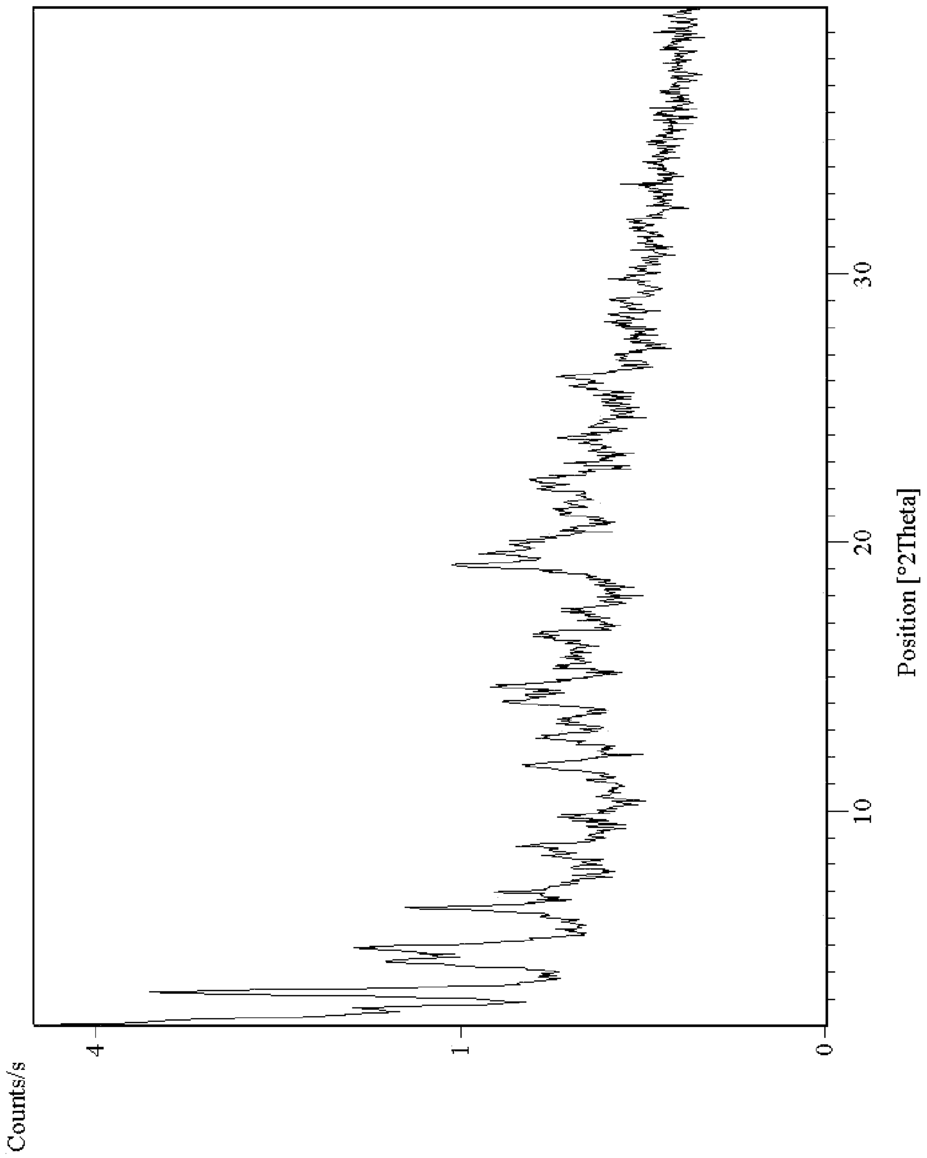
FIG. 7 shows an X-ray powder diffraction pattern of a mono-(2,5-dichlorobenzenesulphonic acid) salt of Compound (I).
Figure 8:
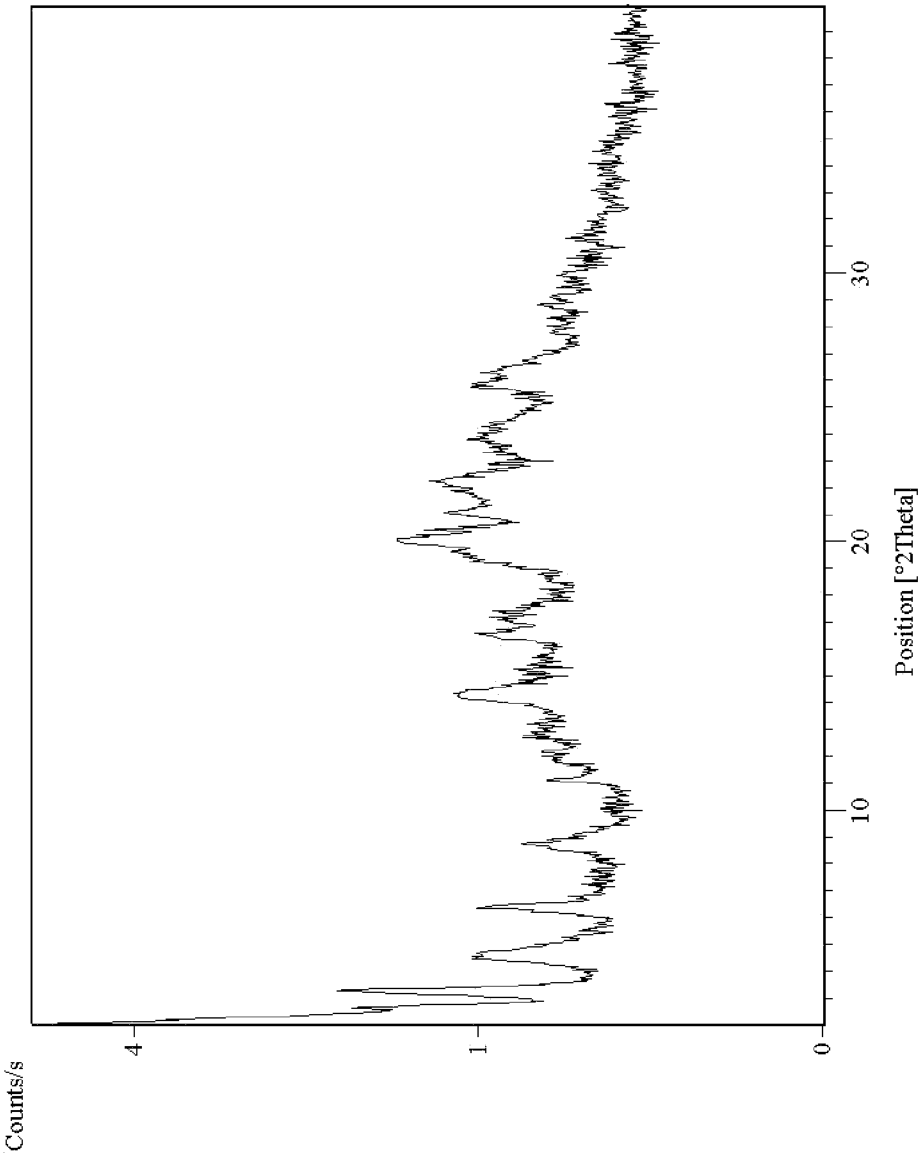
FIG. 8 shows an X-ray powder diffraction pattern of a di-(2,5-dichlorobenzenesulphonic acid) salt of Compound (I).
Figure 9:
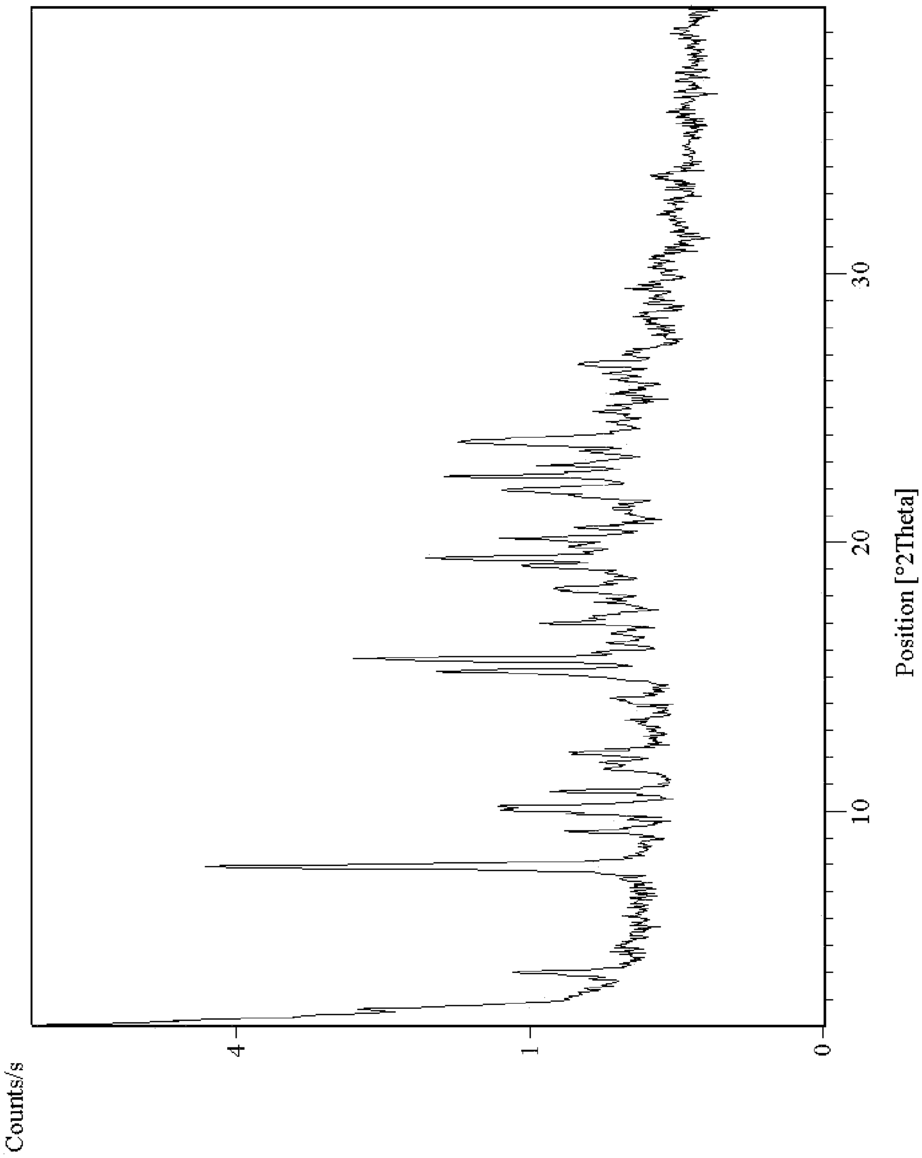
FIG. 9 shows an X-ray powder diffraction pattern of the mono-1,5-naphthalenedisulphonic acid salt of Compound (I) (Form A).
Figure 10:
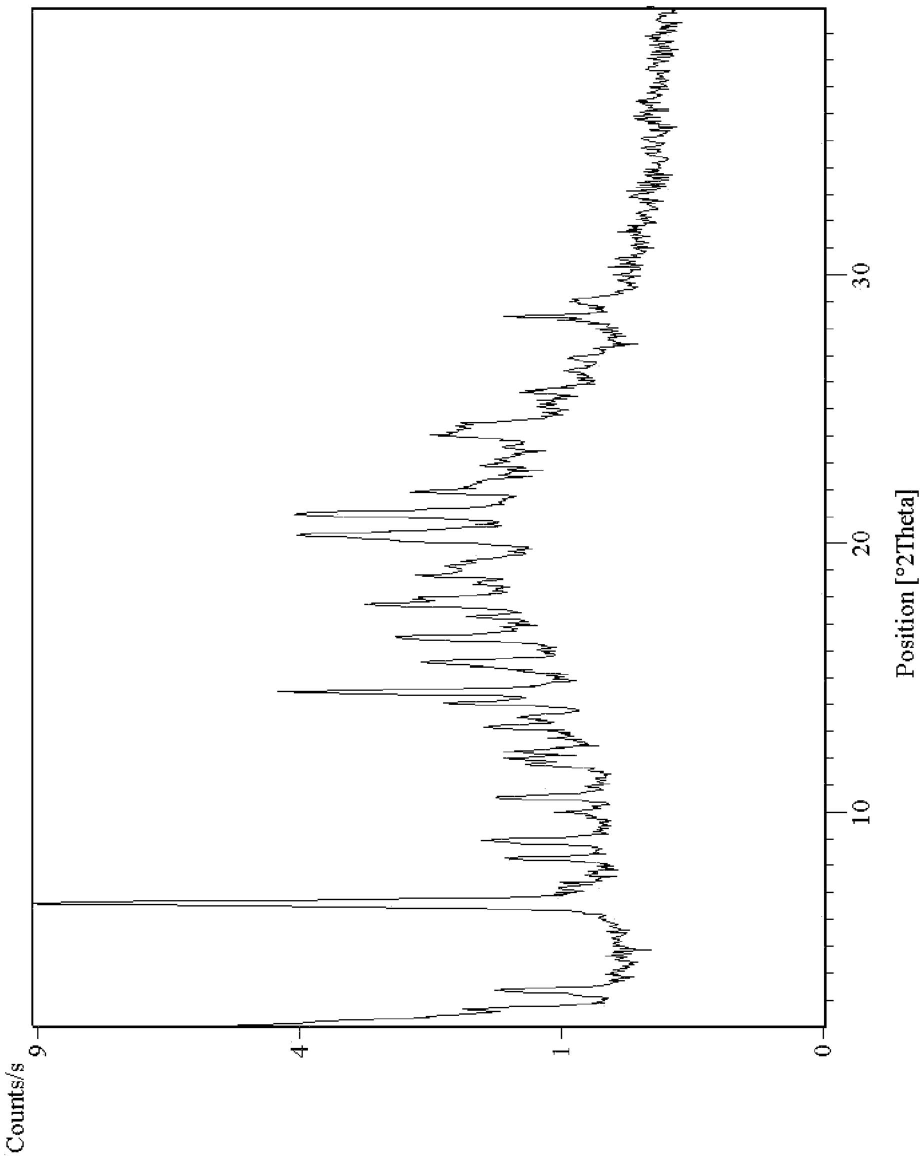
FIG. 10 shows an X-ray powder diffraction pattern of the mono-1,5-naphthalenedisulphonic acid salt of Compound (I) (Form B).
Figure 11:
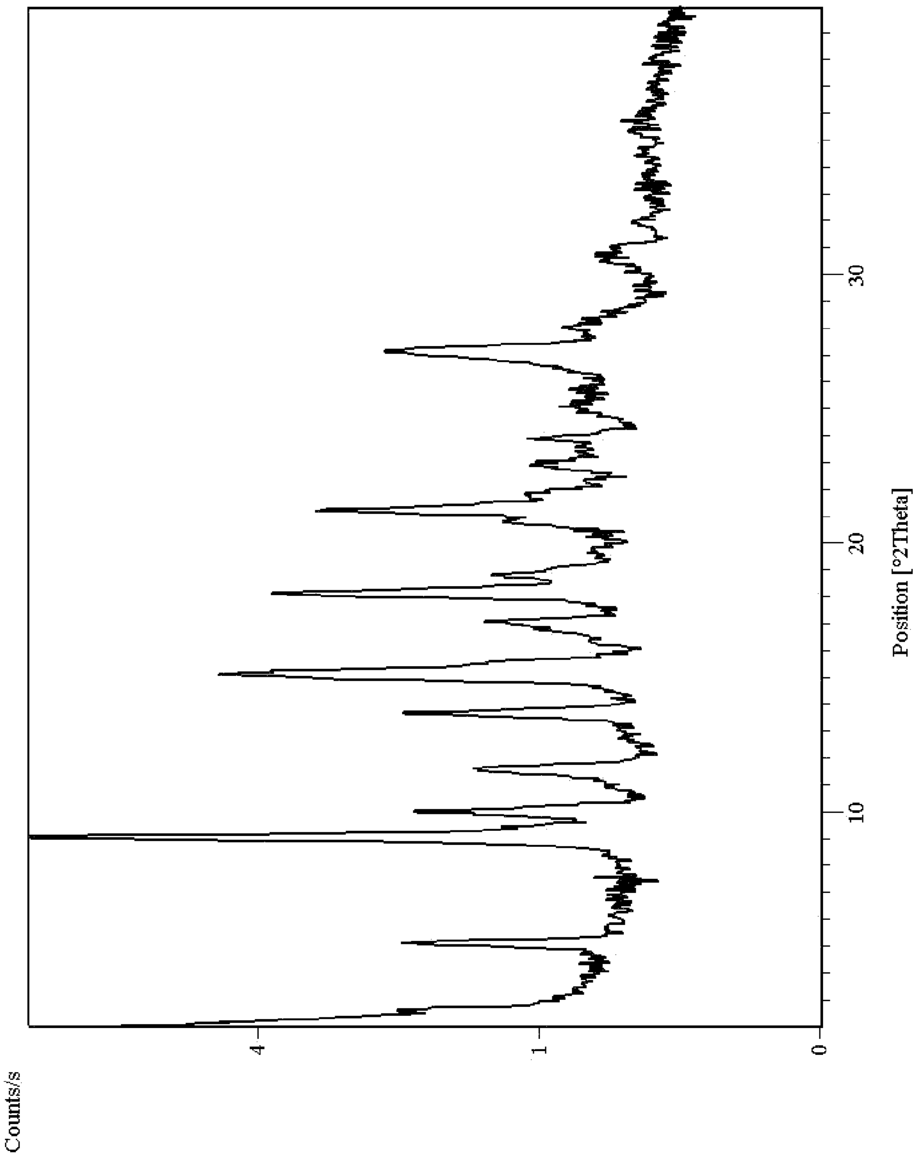
FIG. 11 shows an X-ray powder diffraction pattern of the mono-citric acid salt of Compound (I) (Form A).
Figure 12:
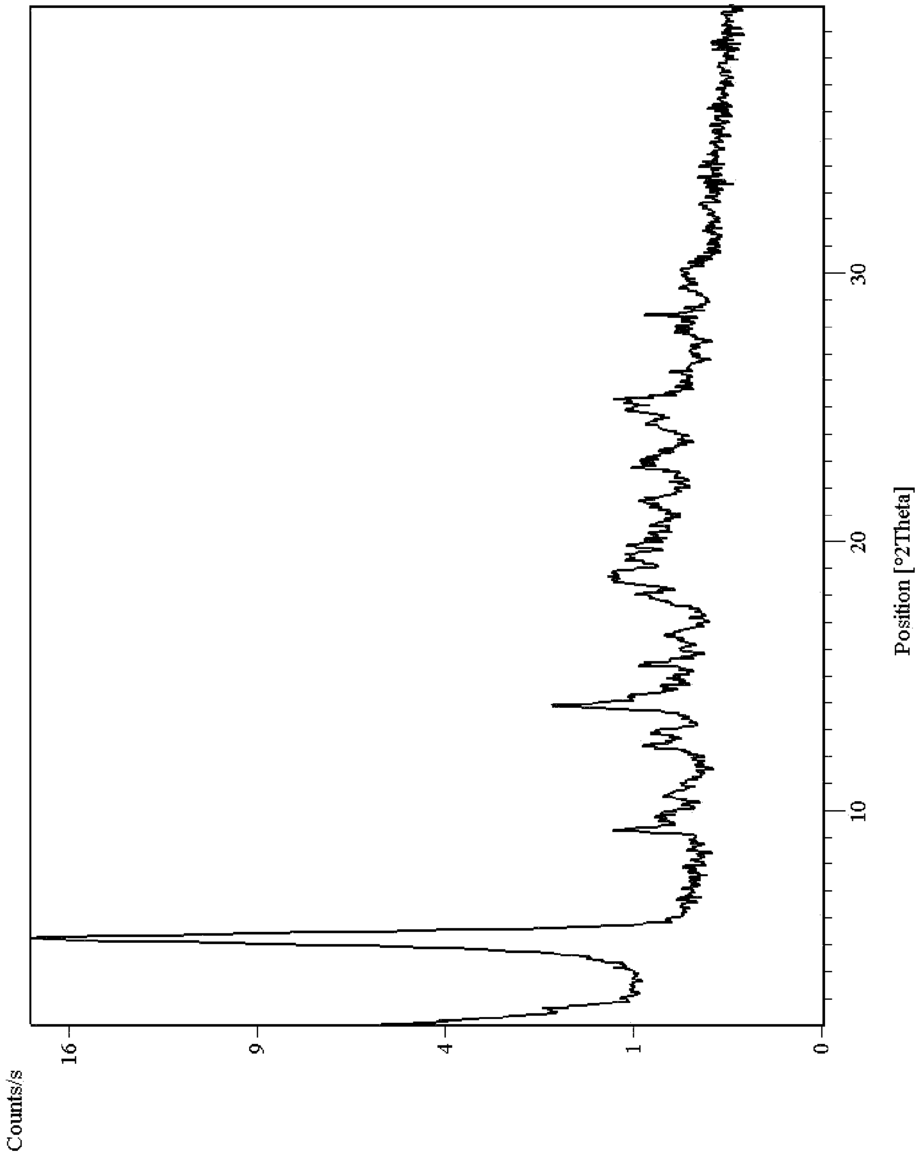
FIG. 12 shows an X-ray powder diffraction pattern of the mono-citric acid salt of Compound (I) (Form B).
Figure 13:
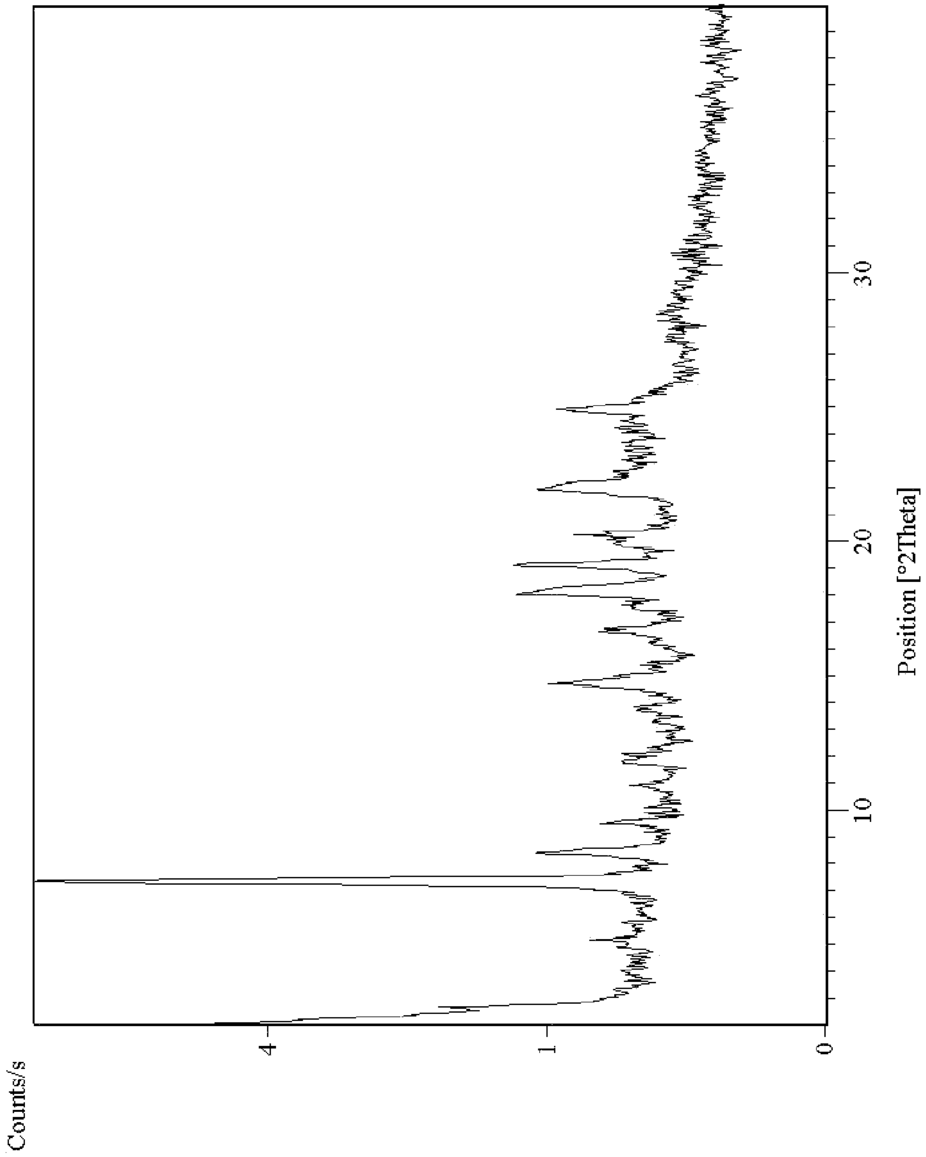
FIG. 13 shows an X-ray powder diffraction pattern of a mono-phosphoric acid salt of Compound (I).
Figure 14:
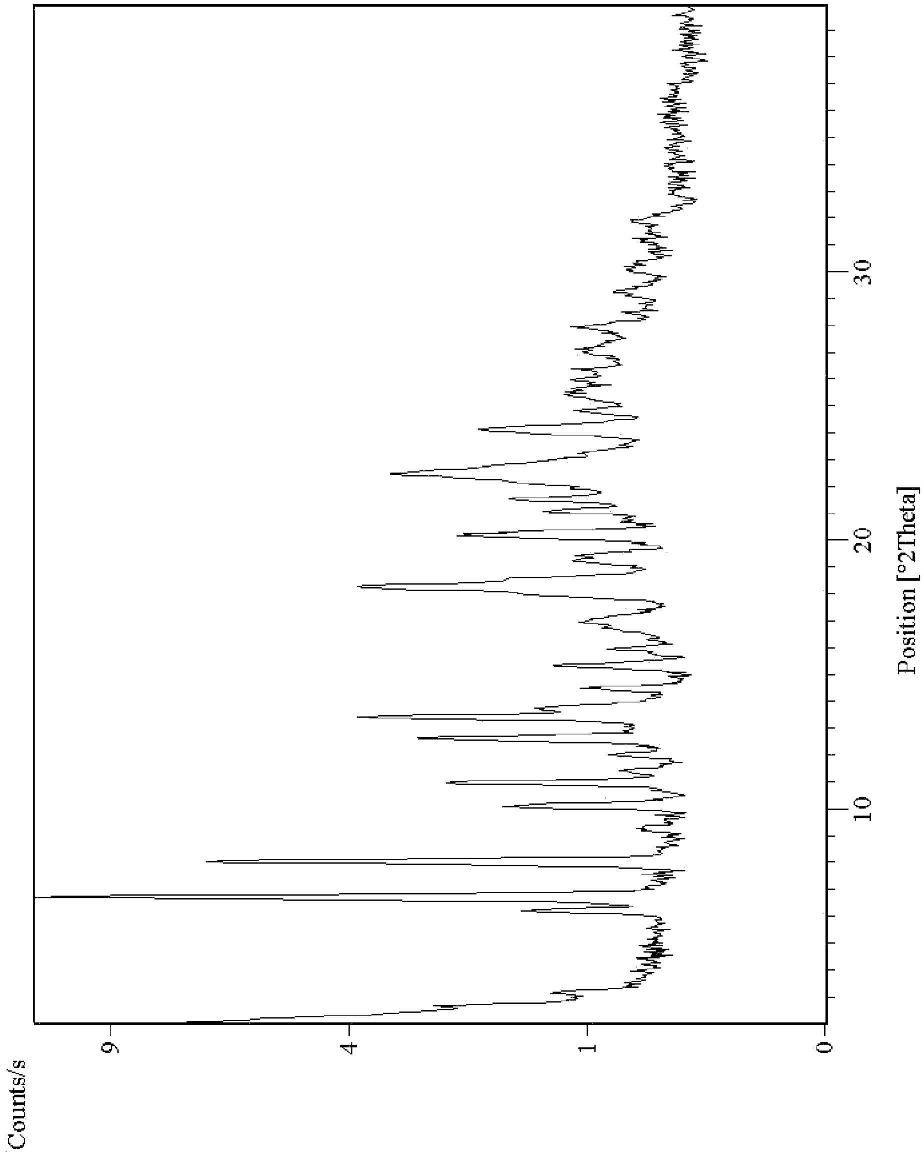
FIG. 14 shows an X-ray powder diffraction pattern of a diphosphoric acid salt of Compound (I).
Figure 15:
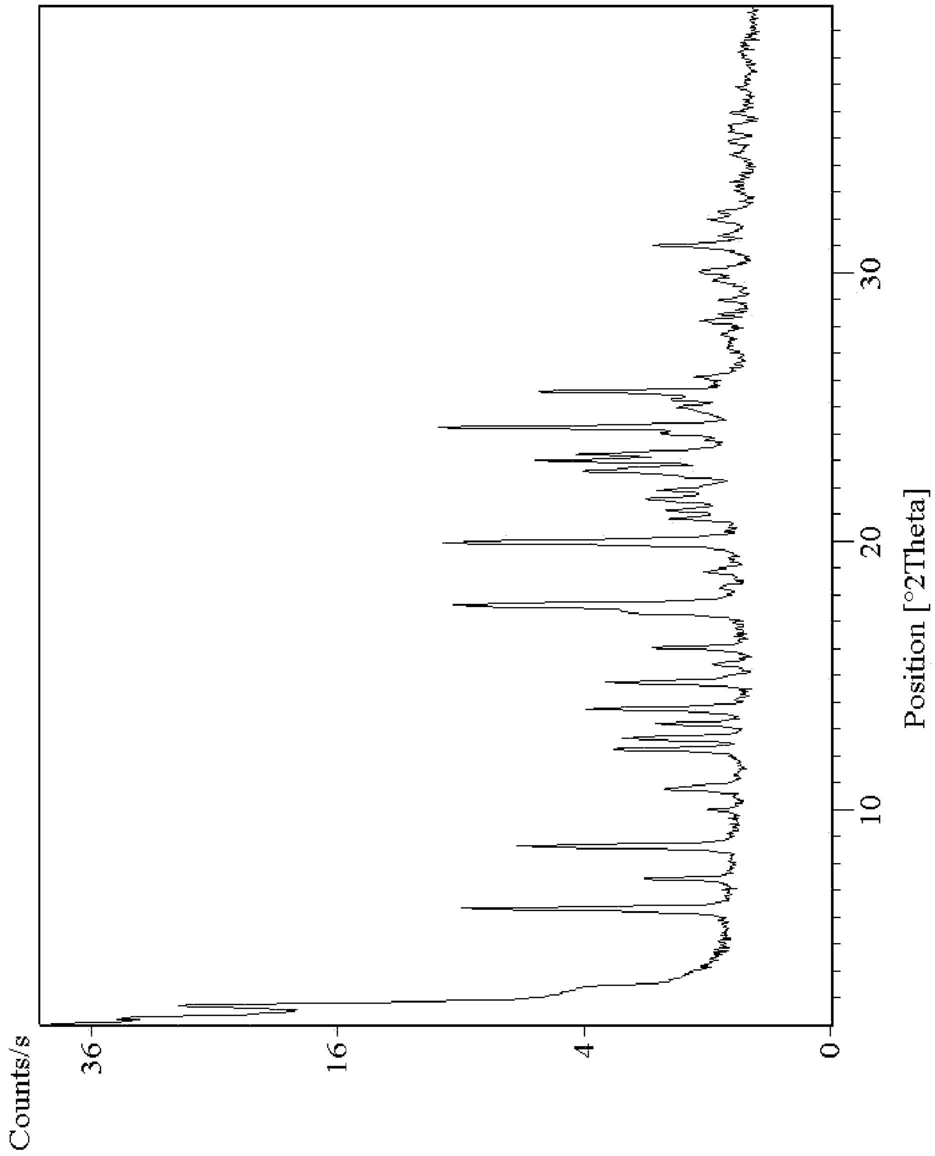
FIG. 15 shows an X-ray powder diffraction pattern of a mono-fumaric acid salt of Compound (I).
Figure 16:
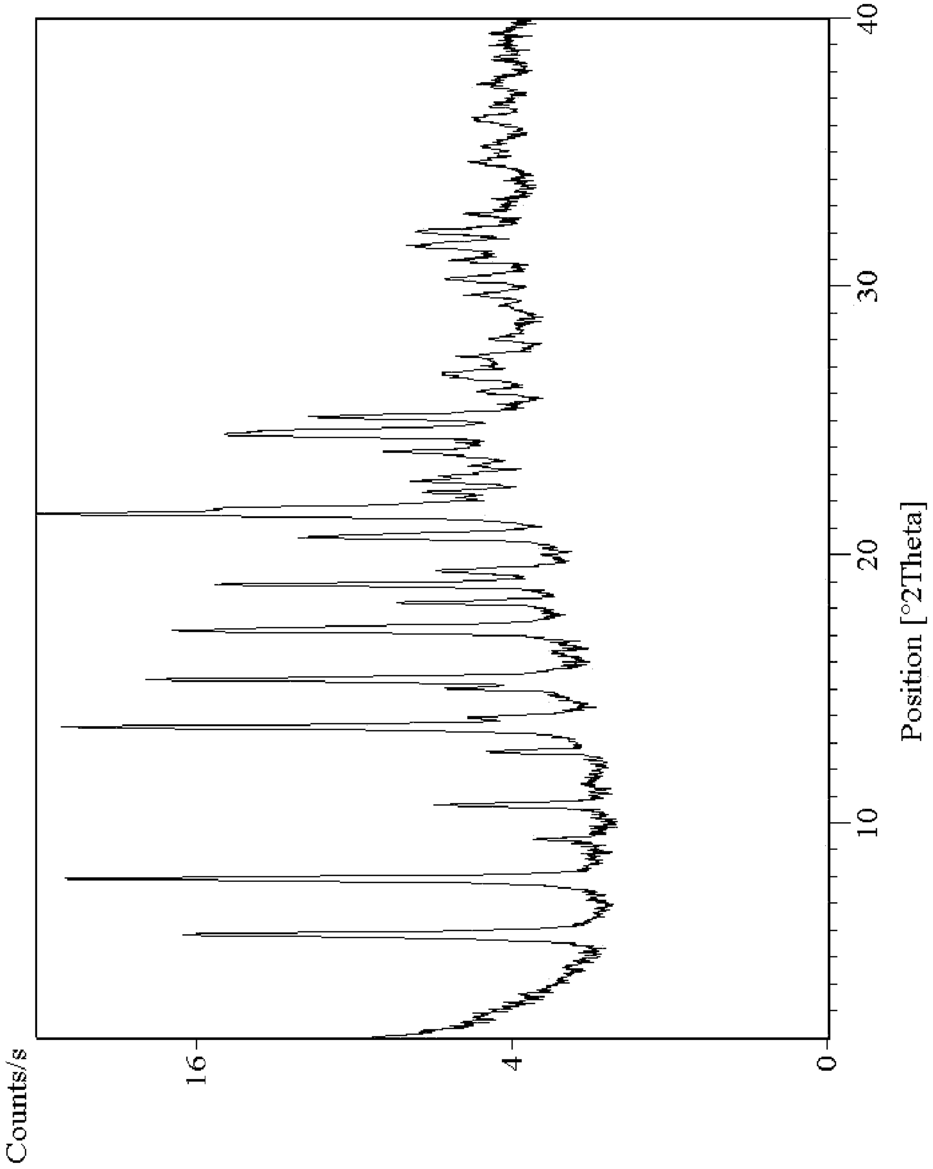
FIG. 16 shows an X-ray powder diffraction pattern of a mono-L-tartaric acid salt of Compound (I).
Figure 17:
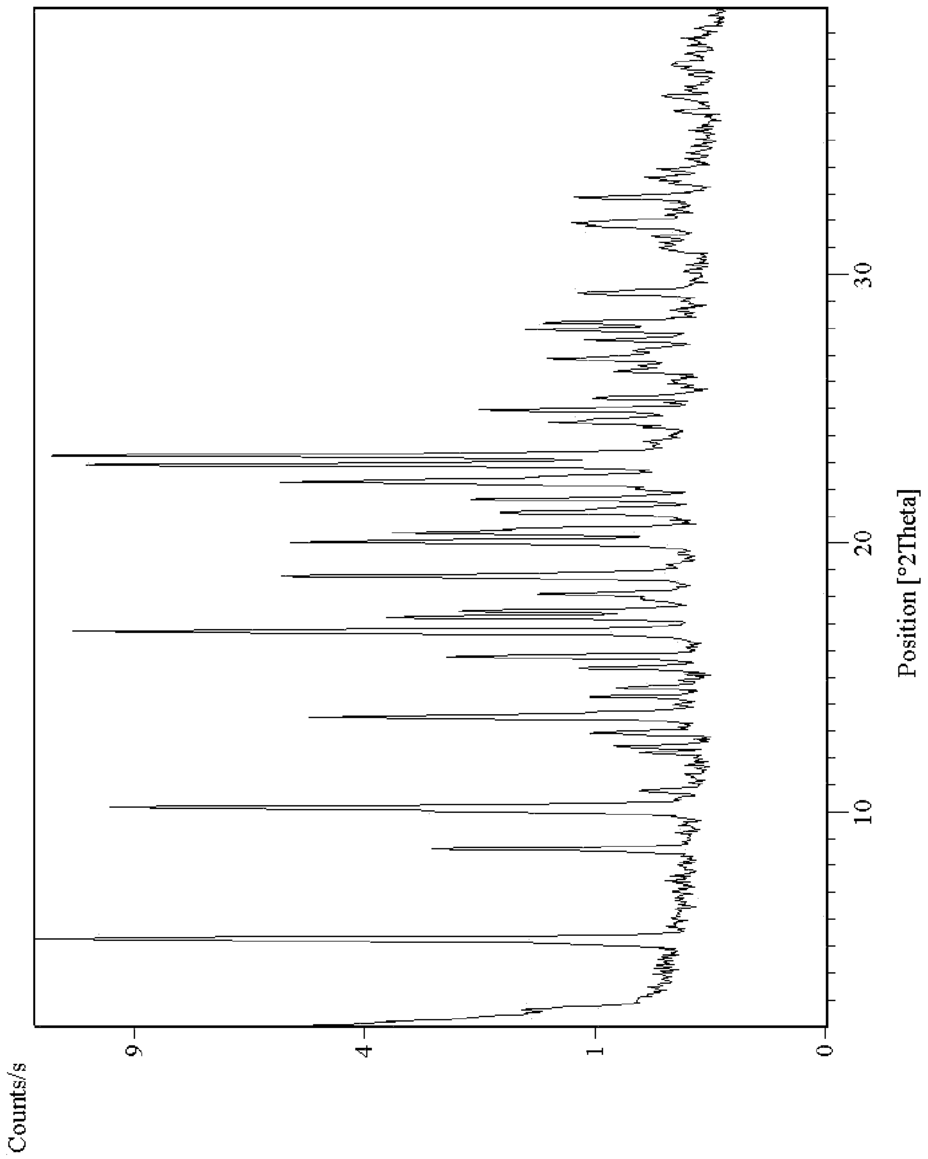
FIG. 17 shows an X-ray powder diffraction pattern of a mono-succinic acid salt of Compound (I).
Figure 18:
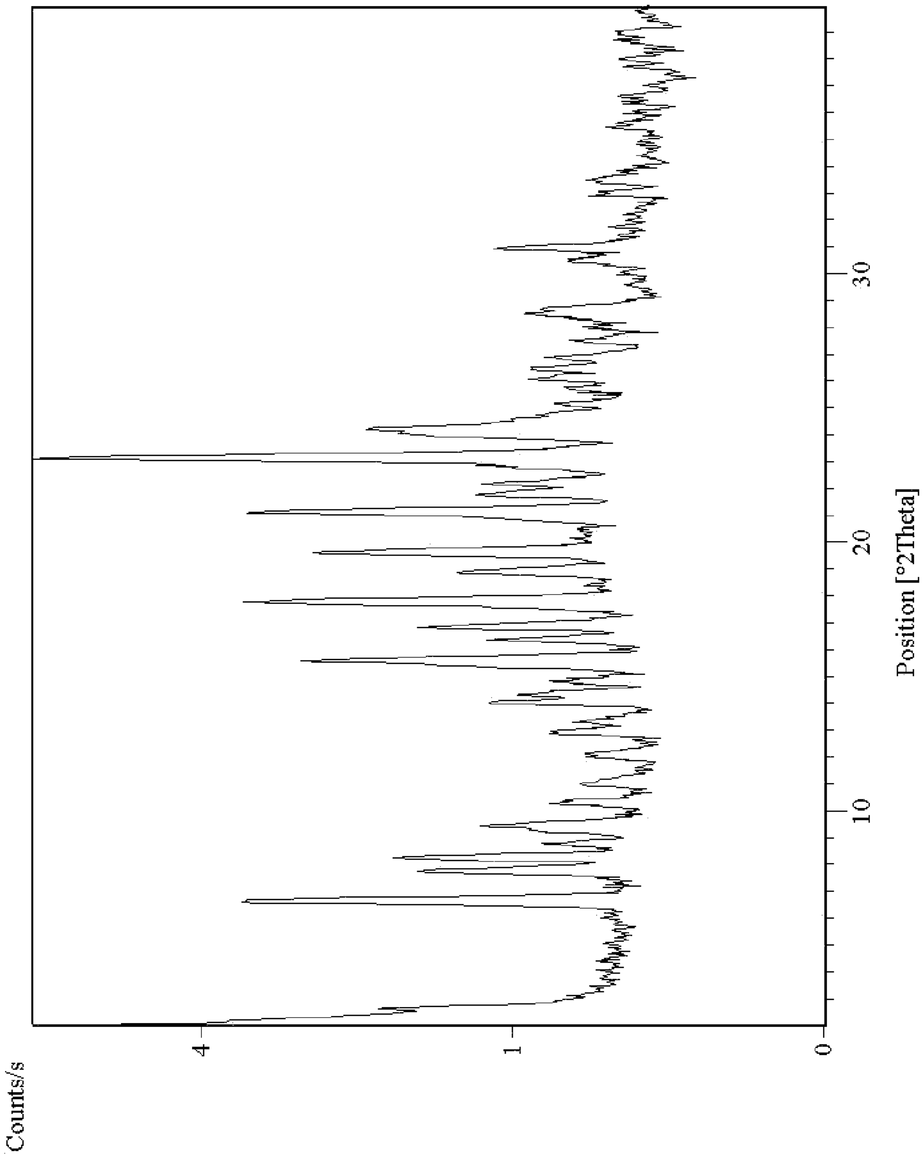
FIG. 18 shows an X-ray powder diffraction pattern of a disuccinic acid salt of Compound (I).

The di-1-hydroxy-2-naphthoic acid salt of Compound (I) is crystalline and provides an X-ray powder diffraction pattern substantially as shown in FIG. 6. The most prominent peaks of the di-1-hydroxy-2-naphthoic acid salt are shown in Table VI in the Examples.

In another embodiment there is provided a di-1-hydroxy-2-naphthoic acid salt of Compound (I), characterised in that said salt has an X-ray powder diffraction pattern with at least one specific peak at 2θ about=8.3°, 16.6°, 19.4° or 23.4°.

In another embodiment there is provided a di-1-hydroxy-2-naphthoic acid salt of Compound (I), characterised in that said salt has an X-ray powder diffraction pattern with at least one specific peak at 2θ about=8.3°, 9.5°, 11.5°, 11.8°, 12.8°, 13.6°, 16.6°, 16.9°, 19.4° or 23.4°

In another embodiment there is provided a di-1-hydroxy-2-naphthoic acid salt of Compound (I), characterised in that said salt has an X-ray powder diffraction pattern with specific peaks at 2θ about=8.3°, 16.6°, 19.4° and 23.4°.

In another embodiment there is provided a di-1-hydroxy-2-naphthoic acid salt of is Compound (I), characterised in that said salt has an X-ray powder diffraction pattern with specific peaks at 2θ about=8.3°, 9.5°, 11.5°, 11.8°, 12.8°, 13.6°, 16.6°, 16.9°, 19.4° and 23.4°

In another embodiment there is provided a di-1-hydroxy-2-naphthoic acid salt of Compound (I), characterised in that said salt has an X-ray powder diffraction pattern substantially as shown in FIG. 6.

According to a further aspect of the invention there is provided a process for the preparation of the di-1-hydroxy-2-naphthoic acid salt of Compound (I) comprising (i) reacting Compound (I) with approximately 2 molar equivalents of 1-hydroxy-2-naphthoic acid in acetonitrile; (ii) concentrating the mixture from step (i); and (iii) crystallising the 1-hydroxy-2-naphthoic acid salt of Compound (I).

Concentration of the mixture in step (ii) may be achieved by removing some or all of the solvent by for example evaporation or distillation. Suitably in step (iii) the salt crystallised by for example, slurrying the salt in a small quantity of ethyacetate for a few days (for example 1 to 7 days) as illustrated in the Examples. Crystalisation of the salt may be aided by seeding the mixture with crystals of the salt. The seed crystals may be prepared using one of the methods described in the Examples.

Benzoic Acid Salt of Compound (I)

In another embodiment of the invention there is provided a benzoic acid salt of Compound (I). The benzoic acid salt in this embodiment is a 1:1 salt with Compound (I) i.e. a mono-benzoic acid salt of Compound (I). The mono-benzoic acid salt of Compound (I) is crystalline and provides an X-ray powder diffraction pattern substantially as shown in FIG. 1. The most prominent peaks of the mono-benzoic acid salt are shown in Table I in the Examples.

In another embodiment there is provided a mono-benzoic acid salt of Compound (I), characterised in that said salt has an X-ray powder diffraction pattern with at least one specific peak at 2θ about=6.3°, 9.3°, 17.8° or 23.8°.

In another embodiment there is provided a mono-benzoic acid salt of Compound (I), characterised in that said benzoic acid salt has an X-ray powder diffraction pattern with at least one specific peak at 2θ about=6.3°, 7.2°, 9.3°, 12.6°, 15.6°, 17.8°, 19.8°, 22.2°, 23.8° or 24.5°.

In another embodiment there is provided a mono-benzoic acid salt of Compound (I), characterised in that said salt has an X-ray powder diffraction pattern with specific peaks at 2θ about=6.3°, 9.3°, 17.8° and 23.8°.

In another embodiment there is provided a mono-benzoic acid salt of Compound (I), characterised in that said salt has an X-ray powder diffraction pattern with specific peaks at 2θ about=6.3°, 7.2°, 9.3°, 12.6°, 15.6°, 17.8°, 19.8°, 22.2°, 23.8° and 24.5°.

In another embodiment there is provided a mono-benzoic acid salt of Compound (I), characterised in that said salt has an X-ray powder diffraction pattern substantially as shown in FIG. 1.

According to a further aspect of the invention there is provided a process for the preparation of the mono-benzoic acid salt of Compound (I) comprising (i) reacting Compound (I) with approximately 1 molar equivalent of benzoic acid in acetonitrile; (ii) concentrating the mixture from step (ii); and (iii) crystallising the mono-benzoic acid salt of Compound (I).

Concentration of the mixture in step (ii) may be achieved by for example removing some or all of the solvent by evaporation or distillation. Suitably in step (iii) the salt may be crystallised by for example, slurrying the salt in a small quantity of acetonitrile as described in the Examples. Crystalisation of the salt may be aided by seeding the mixture with crystals of the salt. The seed crystals may be prepared using one of the methods described in the Examples.

In particular embodiments of the invention the individual crystalline Forms of the salts of Compound (I) are substantially free from other crystalline forms of that salt of Compound (I). For example the described crystalline disaccharin salt of Compound (I) Form A includes less than 30%, 20%, 15%, 10%, 5%, 3% or particularly, less than 1% by weight of other crystalline forms of the disaccharin salt of Compound (I), such as Form B. Accordingly in one embodiment the disaccharin salt of Compound (I) Form A is substantially free from the disaccharin salt of Compound (I) Form B.

In particular embodiments of the invention when the salt stoichiometery is specifically described, for example a 1:1 Compound (I) to acid salt (i.e. a mono-acid salt) or a 1:2 Compound (I) to acid salt (i.e. a di-acid) salt, that salt is suitably substantially free from salts with other stoichiometries. For example, the difumaric acid salt of Compound (I) is substantially free from the mono-fumaric acid salt. Suitably a particular salt of Compound is (I) includes less than 30%, 20%, 15%, 10%, 5%, 3% or particularly, less than 1% by weight of salts of a different stoichiometry.

Where herein the salts are described as having "X-ray powder diffraction pattern with at least one specific peak at 2θ about= . . . " the XRPD of the salt may contain one or more of the 2θ values listed. For example one or more of the 2θ values, 2 or more of the 2θ values or 3 or more of the 2θ values listed.

In the preceding paragraphs defining the X-ray powder diffraction peaks for the crystalline forms of the salts of Compound (I), the term "about=" is used in the expression ". . . at 2θ about= . . . " to indicate that the precise position of peaks (i.e. the recited 2-theta angle values) should not be construed as being absolute values because, as will be appreciated by those skilled in the art, the precise position of the peaks may vary slightly between one measurement apparatus and another, from one sample to another, or as a result of slight variations in measurement conditions utilised. It is also stated in the preceding paragraphs that the crystalline salts of Compound (I) provide X-ray powder diffraction patterns 'substantially' the same as the X-ray powder diffraction patterns shown in FIGS. 1, 4, 5, 6 and 19, and has substantially the most prominent peaks (2-theta angle values) shown in Tables I, IV, V, VI and XIX. It is to be understood that the use of the term 'substantially' in this context is also intended to indicate that the 2-theta angle values of the X-ray powder diffraction patterns may vary slightly from one apparatus to another, from one sample to another, or as a result of slight variations in measurement conditions utilised, so the peak positions shown in the Figures or quoted in the Tables are again not to be construed as absolute values.

The person skilled in the art of X-ray powder diffraction will realize that the relative intensity of peaks can be affected by, for example, grains above approximately 30 micrometer in size and non-unitary aspect ratios which may affect analysis of samples. Furthermore, it should be understood that intensities may fluctuate depending on experimental conditions and sample preparation such as preferred orientation of the particles in the sample. The use of automatic or fixed divergence slits will also influence the relative intensity calculations. A person skilled in the art can handle such effects when comparing diffraction patterns.

The person skilled in the art of X-ray powder diffraction will also realize that due to difference in sample heights and errors in the calibration of the detector position, a small is shift in the 2θ positions could occur. Generally, a difference of ±0.1° from the given value are to be considered correct.

The person skilled in the art will also appreciate that slight variations in the melting point measured by DSC may occur as a result of variations in sample purity, sample preparation and the measurement conditions (e.g. heating rate). It will be appreciated that alternative readings of melting point may be given by other types of equipment or by using conditions different to those described hereinafter. Hence the melting point and endotherm figures quoted herein are not to be taken as absolute values and such measurement errors are to be taken into account when interpreting DSC data. Typically, melting points may vary by ±5° C. or less.

The salts of Compound (I) described herein may also be characterised and/or distinguished from other physical forms using other suitable analytical techniques, for example NIR spectroscopy or solid-state nuclear magnetic resonance spectroscopy.

The chemical structure of the salts of Compound (I) described herein can be confirmed by routine methods for example proton nuclear magnetic resonance (NMR) analysis.

Preparation of Compound (I)

The free base (i.e. Compound (I)) used in the preparation of the salts described herein may be prepared as described in Example 57 of WO2009/067081. Compound (I) may also be prepared as illustrated in the Examples herein. One particular method for the preparation of Compound (I) is illustrated in Reaction Scheme 1, which also shows the final preparation of Compound (I) disaccharin salt Form A.

Reaction Scheme 1

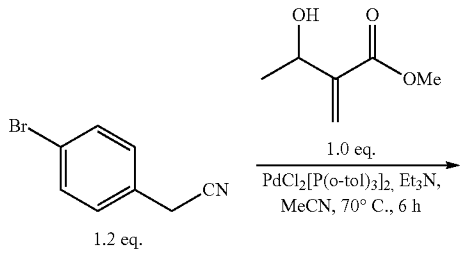

-continued

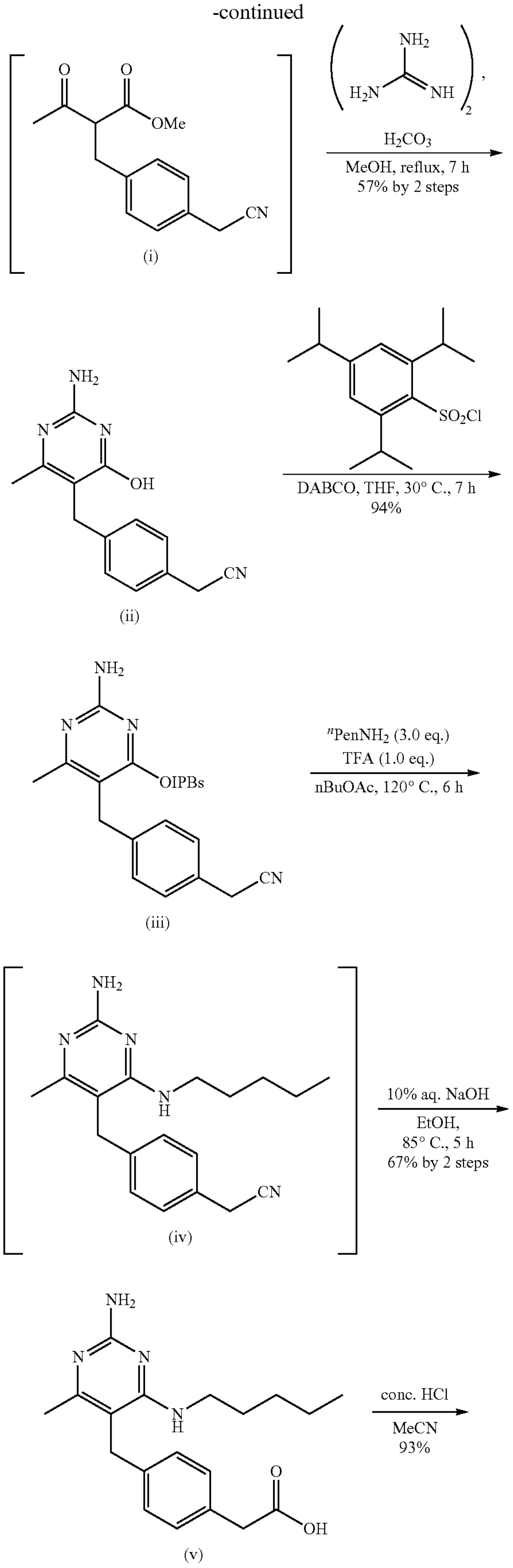

(i)

(ii)

(iii)

(iv)

(v)

-continued

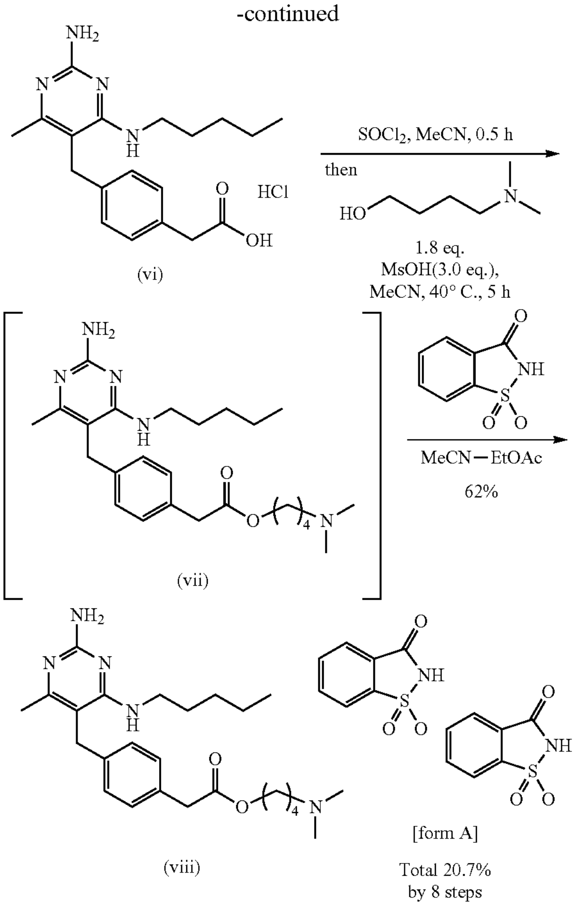

(vi)

(vii)

(viii)

The specific reaction conditions in Reaction Scheme 1 are described in more detail in the Examples. It is to be understood that the specific reaction conditions and solvents etc. are not limiting on the synthetic method illustrated in Reaction Scheme 1. Accordingly other reaction conditions may suitable for the preparation of Compound (I) using the method illustrated by Reaction Scheme 1.

For example in one independent aspect of Reaction Scheme 1, in Step (i) the coupling reaction of methyl 3-hydroxy-2-methylenebutanoate and the 2-(4-bromophenyl)acetonitrile is carried out in the presence of a suitable palladium catalyst and base. Suitably the palladium catalyst is for example, $PdCl_2[P(o\text{-}tol)_3]_2$ (as illustrated in Reaction Scheme 1), $Pd[P(t\text{-}Bu)_3]_2$, $Pd(OAc)_2$ with triphenylphosphine, or $Pd(OAc)_2$ with tetra-n-butylammonium bromide (TBAB). The base may be, for example, an organic amine base or an inorganic base. Examples of organic amine bases include triethylamine and N,N-dicyclohexylmethylamine. Examples of inorganic bases include a suitable carbonate base such as sodium bicarbonate. The reaction is conveniently carried out in the presence of a suitable solvent, for example a polar aprotic solvent, such as tetrahydrofuran (THF), acetonitrile, propionitrile or N,N-dimethylformamide (DMF). The reaction temperature may be 70-80° C. or the reflux temperature of the solvent in the case of THF.

For example in another independent aspect of Reaction Scheme 1, in Step (iii) the reaction of the product of Step (ii) (2-(4-((2-Amino-4-hydroxy-6-methylpyrimidin-5-yl)methyl)phenyl)acetonitrile) may be performed with an arylsulfonylhalide, in the presence of a base. Suitably the arylsulfonyl halide is for example, a substituted benzenesulfonyl halide such as 2,4,6-triisopropylbenzenesulfonyl chloride (IPBsCl—as illustrated in Reaction Scheme 1), 2,4-dimethoxybenzenesulfonyl chloride, 4-methoxybenzenesulfonyl chloride, or 2-mesitylenesulfonyl chloride (2,4,6-trimethylbenzenesulfonyl chloride). The base may be, for example, an organic amine base is or an inorganic base. Examples of organic amine bases include 1,4-diazabicyclo[2.2.2]octane (DABCO), N-methylpyrolidine, N-methylmorpholine, N,N,N',N'-tetramethyl-1,3-propanediamine (TMPDA), TMPDA with a catalytic amount of N-methylimidazole (NMI) 1,8-Diazabicyclo[5.4.0]undec-7-ene (DBU) with a catalytic amount of NMI, or trimethylamine hydrochloride with a double to triple molar ratio of triethylamine. Examples of inorganic bases include a suitable carbonate base such as potassium carbonate. The solvent may be a polar aprotic solvent or an aromatic hydrocarbon. The reaction is conveniently carried out in the presence of a suitable solvent, for example a polar aprotic solvent such as acetonitrile, tetrahydrofuran (THF) or 2-methyltetrahydrofuran; or an aromatic hydrocarbon such as toluene.

Diseases and Medical Conditions

The salts (including the solvated forms) according to the invention are useful as modulators of TLR7 activity and thus may administered to a mammal, including man, for the treatment of the following conditions or diseases:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;
2. skin: psoriasis, atopic dermatitis, contact dermatitis or other eczematous dermatoses, and delayed-type hypersensitivity reactions; phyto- and photodermatitis; seborrhoeic is dermatitis, dermatitis herpetiformis, actinic keratosis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia areata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;
3. eyes: blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; infections including viral, fungal, and bacterial;

4. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);
5. allograft rejection: acute and chronic following, for example, transplantation of kidney, heart, liver, lung, bone marrow, skin or cornea or following blood transfusion; or chronic graft versus host disease;
6. other auto-immune and allergic disorders including rheumatoid arthritis, irritable bowel syndrome, systemic lupus erythematosus, multiple sclerosis, Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome and Sazary syndrome;
7. oncology: treatment of common cancers including prostate, breast, lung, ovarian, pancreatic, bowel and colon, stomach, skin and brain tumours and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and,
8. infectious diseases: virus diseases such as genital warts, common warts, plantar warts, hepatitis B, hepatitis C, herpes simplex virus, molluscum contagiosum, variola, human immunodeficiency virus (HIV), human papilloma virus (HPV), cytomegalovirus (CMV), varicella zoster virus (VZV), rhinovirus, adenovirus, coronavirus, influenza, para-influenza; bacterial diseases such as tuberculosis and mycobacterium avium, leprosy; other infectious diseases, such as fungal diseases, chlamydia, candida, aspergillus, cryptococcal meningitis, pneumocystis carni, cryptosporidiosis, histoplasmosis, toxoplasmosis, trypanosome infection and leishmaniasis.

Thus, the present invention provides a salt of Compound (I) defined herein or a solvate of the salt, for use in therapy.

In a further aspect, the present invention provides the use of a salt of Compound (I) defined herein or a solvate of the salt, in the manufacture of a medicament for use in therapy.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

In particular, the salts (including the solvated forms) according to the invention may be used in the treatment of asthma, COPD, allergic rhinitis, allergic conjunctivitis, atopic dermatitis, cancer, hepatitis B, hepatitis C, HIV, HPV, bacterial infections and dermatosis. In addition the salts may also be useful as vaccine adjuvants.

Accordingly, as a further aspect of the invention there is provided a salt of Compound (I) defined herein or a solvate of the salt, for use in the treatment of asthma, COPD or allergic rhinitis.

As a further aspect of the invention there is provided a salt of Compound (I) defined herein or a solvate of the salt, for use in the treatment of asthma.

As a further aspect of the invention there is provided a salt of Compound (I) defined herein or a solvate of the salt, for use in the treatment of COPD.

As a further aspect of the invention there is provided a salt of Compound (I) defined herein or a solvate of the salt, for use in the treatment of allergic rhinitis.

As a further aspect of the invention there is provided a salt of Compound (I) defined herein or a solvate of the salt, for use as a vaccine adjuvant.

As a further aspect of the invention there is provided the use of a salt of Compound (I) defined herein or a solvate of the salt, in the manufacture of a medicament for the treatment of asthma, COPD or allergic rhinitis.

As a further aspect of the invention there is provided the use of a salt of Compound (I) defined herein or a solvate of the salt, in the manufacture of a medicament for the treatment of asthma.

As a further aspect of the invention there is provided the use of a salt of Compound (I) defined herein or a solvate of the salt, in the manufacture of a medicament for the treatment of COPD.

As a further aspect of the invention there is provided the use of a salt of Compound (I) defined herein or a solvate of the salt, in the manufacture of a medicament for the treatment of allergic rhinitis.

As a further aspect of the invention there is provided the use of a salt of Compound (I) defined herein or a solvate of the salt as a vaccine adjuvant, in the manufacture of a vaccine for the treatment of a disease or condition.

The invention therefore provides a method of treating an inflammatory disease in a patient suffering from, or at risk of, said disease, which comprises administering to the patient a therapeutically effective amount of a salt of Compound (I) defined herein or a solvate of the salt.

The invention also provides a method of treating an airways disease, e.g. a reversible obstructive airways disease such as asthma, in a patient suffering from, or at risk of, said disease, which comprises administering to the patient a therapeutically effective amount of a salt of Compound (I) defined herein or a solvate of the salt.

The invention still further provides a method of treating, or reducing the risk of, a disease or condition comprising or arising from abnormal cell growth (e.g. a cancer), which method comprises administering to a patient in need thereof a therapeutically effective amount of a salt of Compound (I) defined herein or a solvate of the salt.

The invention still further provides a method of treating, or reducing the risk of, a disease or condition, which method comprises administering to a patient in need thereof a therapeutically effective amount of a vaccine and a salt of Compound (I) defined herein or a solvate of the salt.

The invention still further provides a method of increasing the response to a vaccine in a patient, which method comprises administering to a patient in need thereof a therapeutically effective amount of a vaccine and a salt of Compound (I) defined herein or a solvate of the salt.

For the above-mentioned therapeutic uses the dosage administered will, of course, vary with the salt employed, the mode of administration, the treatment desired and the disorder indicated. For example, the daily dosage of the (solvated)

salt, if inhaled, may be in the range from 0.05 micrograms per kilogram body weight (μg/kg) to 100 micrograms per kilogram body weight (μg/kg). For example a dose of about 0.1, to 100 μg/kg such as a dose of about 0.1, 0.5, 1, 2, 5, 10, 20, 50 or 100 μg/kg. Alternatively, if the (solvated) salt is administered orally, then the daily dosage may be in the range from 0.01 micrograms per kilogram body weight (μg/kg) to 100 milligrams per kilogram body weight (mg/kg).

The dosages mentioned herein refer to the dose of Compound (I) as the free base. Accordingly, the equivalent dose of a particular salt will be higher because of the increased molecular weight of the salt compared to the free base.

The salts according to the invention may be used on their own but will generally be administered in the form of a pharmaceutical composition in which the salt or a solvate thereof (active ingredient) is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration, the pharmaceutical composition may comprise from 0.05 to 99% w (per cent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a salt of Compound (I) defined herein or a solvate of the salt in association with a pharmaceutically acceptable adjuvant, diluent or carrier.

The invention further provides a process for the preparation of a pharmaceutical composition of the invention which comprises mixing a salt of Compound (I) defined herein or a solvate of the salt with a pharmaceutically acceptable adjuvant, diluent or carrier.

The pharmaceutical compositions may be administered topically (e.g. to the skin or to the lung and/or airways (by oral or nasal inhalation) administration) in the form, e.g., of creams, solutions, suspensions, heptafluoroalkane (HFA) aerosols and dry powder formulations, for example, formulations in the inhaler device known as the Turbuhaler®; or systemically, e.g. by oral administration in the form of tablets, capsules, syrups, powders or granules; or by parenteral administration in the form of solutions or suspensions; or by subcutaneous administration; or by rectal administration in the form of suppositories; or transdermally.

Pharmaceutical Compositions for Administration by Inhalation

In an embodiment of the invention, the pharmaceutical composition is administered by inhalation (oral or nasal).

The salt of Compound (I) may be administered using a suitable delivery device, for example from a dry powder inhaler, a metered dose inhaler, a nebuliser or a nasal delivery device. Such devices are well known.

In a further embodiment, the pharmaceutical composition is administered by means of a dry powder inhaler (DPI).

The DPI may be "passive" or breath-actuated, or "active" where the powder is dispersed by some mechanism other than the patient's inhalation, for instance, an internal supply of compressed air. At present, three types of passive dry powder inhalers are available: single-dose, multiple unit dose or multidose (reservoir) inhalers. In single-dose devices, individual doses are provided, usually in gelatine capsules, and have to be loaded into the inhaler before use, examples of which include Spinhaler® (Aventis), Rotahaler® (GlaxoSmithKline), Aerohser™ (Novartis), Inhalator® (Boehringer) and Eclipse (Aventis) devices. Multiple unit dose inhalers contain a number of individually packaged doses, either as multiple gelatine capsules or in blisters, examples of which include Diskhaler® (GlaxoSmithKline), Diskus® (GlaxoSmithKline) and Aerohaler® (Boehringer) devices. In multidose devices, drug is stored in a bulk powder reservoir from which individual doses are metered, examples of which include Turbuhaler® (AstraZeneca), Easyhaler® (Orion), Novolizer® (ASTA Medica), Clickhaler® (Innovata Biomed) and Pulvinal® (Chiesi) devices.

An inhalable pharmaceutical composition or dry powder formulation for use in a DPI can be prepared by mixing finely divided active ingredient (having a mass median is diameter generally equal to or less than 10 μm, preferably equal to or less than 5 μm) with a carrier substance, for example, a mono-, di- or polysaccharide, a sugar alcohol, or another polyol. Suitable carriers are sugars or sugar alcohols, for example, lactose, glucose, raffinose, melezitose, lactitol, maltitol, trehalose, sucrose, mannitol; and starch. The carrier particles may have a mass median diameter of from 20 to 1000 μm, more usually from 50 to 500 μm. The powder mixture may then, as required, be dispensed into hard gelatine capsules, each containing the desired dose of the active ingredient.

Alternatively, an inhalable pharmaceutical composition may be prepared by processing a finely divided powder (e.g. consisting of finely divided active ingredient and finely divided carrier particles) into spheres that break up during the inhalation procedure. This spheronized powder is filled into the drug reservoir of a multidose inhaler, for example, that known as the Turbuhaler® in which a dosing unit meters the desired dose which is then inhaled by the patient.

Accordingly, the present invention also provides a dry powder inhaler, in particular a multiple unit dose dry powder inhaler, containing an inhalable pharmaceutical composition of the invention.

In a further embodiment, the salt of Compound (I) is administered by means of a metered dose inhaler (MDI), particularly a pressurised metered dose inhaler (pMDI). The pMDI contains the active as a suitable solution or suspension in a pressurised container. The active is delivered by actuating a valve on the pMDI device. Actuation may be manual or breath actuated. In manually actuated pMDIs the device is actuated by the user as they inhale, for example by pressing a suitable release mechanism on the pMDI device. Breath actuated pMDIs are actuated when the patient inhales through the mouthpiece of the pMDI. This can be advantageous as the actuation of the device is timed with the patients' inhalation and can result in a more consistent dosing of the active. An example of a pMDI device includes Rapihaler® (AstraZeneca).

An inhalable pharmaceutical composition for use in a pMDIcan be prepared by is dissolving or dispersing the salt of Compound (I) in a suitable propellant and with or without additional excipients such as solvents (for example ethanol), surfactants, lubricants, preservatives or stabilising agents. Suitable propellants include hydrocarbon, chlorofluorocarbon and hydrofluoroalkane (e.g. heptafluoroalkane) propellants, or mixtures of any such propellants. Preferred propellants are P134a and P227, each of which may be used alone or in combination with other propellants and/or surfactant and/or other excipients. When the salt of Compound (I) is used as a suspension, the salt is suitably present in finely divided form (having a mass median diameter generally equal to or less than 10 μm, preferably equal to or less than 5 μm).

In a further embodiment, the salt of Compound (I) is administered by means of a metered dose inhaler in combination with a spacer. Suitable spacers are well known and include Nebuchamber® (AstraZeneca) or Volumatic® (GSK).

In a further embodiment, the salt of Compound (I) is administered by means of a nebuliser. Suitable nebulisers are well known.

An inhalable pharmaceutical composition for use in a nebuliser can be prepared by dispersing or preferably dissolving the salt of Compound (I) in a suitable aqueous medium. The composition may also include for example suitable pH and/or tonicity adjustment, surfactants and preservatives. An example of a suitable composition includes a composition comprising the salt of Compound (I), a citrate buffer and saline.

In a further embodiment, the salt of Compound (I) is administered nasally as a spray from a suitable nasal delivery device, for example a spray pump or an MDI adapted for nasal delivery. Alternatively, the salt could be administered nasally as a powder using a suitable DPI device e.g. Rhinocort® Turbuhaler® (AstraZeneca).

A nasally inhalable pharmaceutical composition for use in a spray pump or MDI nasal delivery device can be prepared by dispersing or preferably dissolving the salt of Compound (I) in a suitable aqueous medium similar to those described above for inhalation via an MDI device. Suitable dry powder compositions for nasal delivery are as hereinbefore described in relation to DPI delivery. However, where it is desirable to limit the penetration of the compound into the lung and keep the compound in the nasal cavity, it may be necessary to use the compound as larger particle sizes, for example with an average particle diameter greater than about 10 μm, for example from 10 μm to 50 μm.

Accordingly, the present invention also provides an inhaler device suitable for nasal administration (for example a dry powder inhaler, in particular a multiple unit dose dry powder inhaler, or a pMDI inhaler) containing an inhalable pharmaceutical composition of the invention.

The salts according to the invention may also be administered in conjunction with other compounds used for the treatment of the above conditions. Examples of such additional compounds include those described in WO2009/067081.

It is to be understood that references to "a salt of Compound (I)" in relation to the uses, methods of treatment, pharmaceutical compositions and administration is intended to cover any one of the salts described herein, for example a benzoic acid, trans-cinnamic acid, methanesulphonic acid, disaccharin, 1-hydroxy-2-naphthoic acid, di-1-hydroxy-2-naphthoic acid, 2,5-dichlorobenzenesulphonic acid, di-2,5-dichlorobenzenesulphonic acid, 1,5-naphthalenedisulphonic acid, citric acid, phosphoric acid, diphosphoric acid, fumaric acid, difumaric acid, L-tartaric acid, succinic acid, disuccinic acid salt of 4-(dimethylamino)butyl 2-(4-((2-amino-4-methyl-6-(pentylamino)pyrimidin-5-yl)methyl)phenyl)acetate.

The invention therefore further relates to combination therapies wherein a salt according to the invention, or a pharmaceutical composition comprising a salt according to the invention, is administered concurrently or sequentially or as a combined preparation with another therapeutic agent or agents, for the treatment of one or more of the conditions listed.

EXAMPLES

The present invention will now be further explained by reference to the following illustrative examples in which, unless stated otherwise:

(i) Temperatures are given in degrees Celsius (° C.); operations were carried out at room or ambient temperature, that is, at a temperature in the range of 18-25° C.

(ii) In general, the course of reactions was followed by HPLC and reaction times are given for illustration only.

(iii) Yields are given for illustration only and are not necessarily those which can be obtained by diligent process development; preparations were repeated if more material was required.

(iv) Chemical symbols have their usual meanings; SI units and symbols are used.

(v) Solvent ratios are given in volume:volume (v/v) terms.

(vi) Unless stated otherwise, starting materials were commercially available.

General Methods

NMR $^1$H NMR spectra were recorded at 298K on a Varian Unity Inova 400 MHz (software: VNMR 6.1C and VNMRJ 1.1D; probe: Nalorac 5 mm DG400-5AT) or a Varian Mercury-VX 300 MHz (software: VNMR 6.1C; probe: Varian 5 mm AutoSW PFG) instrument. The central peaks of acetone-$d_6$ or dimethylsulphoxide (DMSO)-$d_6$ were used as internal references.

Differential Scanning Calorimetry (DSC)

Using standard methods (for example those described in Höhne, G. W. H. et al (1996), Differential Scanning Calorimetry, Springer, Berlin) the calorimetric response of a test sample to increasing temperature was investigated using a TA Instruments Q2000 Differential Scanning Calorimeter (DSC). Measurements were performed between 0 and 250° C. a ramp rate of 10° C. per minute. Approximately 0.5 to 5 mg of test sample was placed in aluminium pans with lids (no crimping) under a flow of nitrogen gas (50 mL/min).

As mentioned hereinbefore, it is well known that the DSC onset and peak temperatures may vary according to the purity of the sample and instrumental parameters, especially the temperature scan rate. A person skilled in the art can use routine optimization/calibration to set up instrumental parameters for a differential scanning calorimeter so that data comparable to the data presented here can be collected.

Abbreviations

The following abbreviations have been used.

| | |
|---|---|
| Aq: | aqueous |
| DABCO: | 1,4-diazabicyclo[2.2.2]octane |
| EDCI: | 1-ethyl-3-(3-dimethylaminopropyl) carbodiimide |
| EtOAc: | ethyl acetate |
| HOBT: | hydroxybenzotriazole |
| MeCN: | acetonitrile |
| $^i$PrOAc: | isopropyl acetate |
| RPHPLC: | reverse phase high performance liquid chromatography |
| THF: | tetrahydrofuran |

Adduct (Salt) Preparation

4-(Dimethylamino)butyl 2-(4-((2-amino-4-methyl-6-(pentylamino)pyrimidin-5-yl)methyl)phenyl)acetate adduct (salt) formation Unless stated otherwise the adducts (salts) described in the Examples below were prepared as follows:

To aliquots of a solution of 4-(dimethylamino)butyl 2-(4-((2-amino-4-methyl-6-(pentylamino)pyrimidin-5-yl)methyl)phenyl)acetate (20 mg) in acetonitrile (2 mL) was added 1 or 2 molar equivalents of the corresponding acid as either the solid or dissolved in acetonitrile (2 mL) (benzoic acid (solid), trans cinnamic acid (solid), methanesulphonic acid, 2,5-dichlorobenzenesulphonic acid, citric acid, 1,5-naphthalenedisulphonic acid, 85% aq phosphoric acid, succinic acid (solid), fumaric acid (solid), L-tartaric acid, saccharin (solid) or 2-hydroxy-1-naphthoic acid (solid)). The solvent was removed from the resulting mixtures by evaporation in the open air. Solvent (either acetonitrile, tetrahydrofuran, ethyl acetate, dimethoxyethylether, methyl tent-butyl ether, 1,4-dioxane or diethyl ether; 2 mL each) was then added to these residues and the mixtures were slurried for 7 days to form corresponding adducts. Solids were filtered using centrifuge and dried under vacuum.

Example 1

4-(Dimethylamino)butyl 2-(4-((2-amino-4-methyl-6-(pentylamino)pyrimidin-5-yl)methyl)phenyl)acetate benzoic acid salt

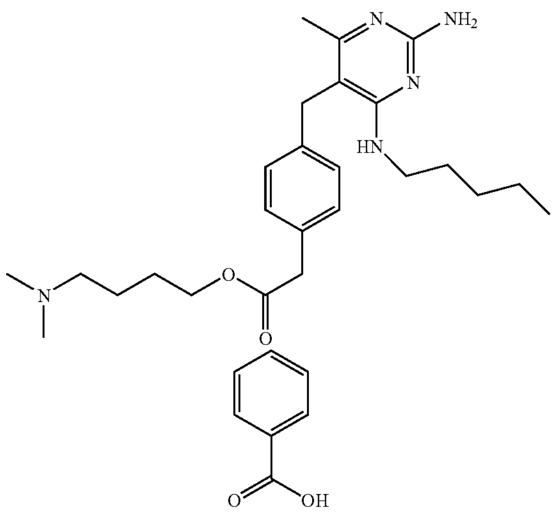

The preparation involved slurrying with acetonitrile. The stoichiometry, Compound (I) to acid, of 1:1 was confirmed by NMR.

$^1$H NMR DMSO-d6: δ 7.96-7.91 (2H, m), 7.59-7.54 (1H, m), 7.49-7.43 (2H, m), 7.14 (2H, d), 7.05 (2H, d), 6.36 (1H, t), 6.10 (2H, s), 4.01 (2H, t), 3.72 (2H, s), 3.58 (2H, s), 3.29-3.22 (2H, m), 2.19 (2H, t), 2.09 (6H, s), 2.04 (3H, s), 1.59-1.49 (2H, m), 1.48-1.34 (4H, m), 1.28-1.09 (4H, m), 0.82 (3H, t)

Example 2

4-(Dimethylamino)butyl 2-(4-((2-amino-4-methyl-6-(pentylamino)pyrimidin-5-yl)methyl)phenyl)acetate trans-cinnamic acid salt

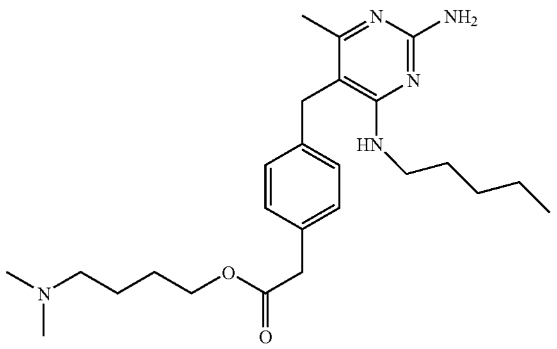

-continued

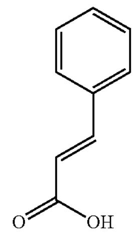

The preparation involved slurrying with diethyl ether. The stoichiometry, Compound (I) to acid, of 1:1 was confirmed by NMR.

$^1$H NMR DMSO-d6: δ 7.67-7.61 (m, 2H), 7.48 (d, 1H), 7.44-7.35 (m, 3H), 7.18-7.09 (m, 2H), 7.07-6.98 (m, 2H), 6.50 (d, 1H), 6.20-6.11 (m, 1H), 5.69 (s, 2H), 4.01 (t, 2H), 3.71 (s, 2H), 3.58 (s, 2H), 3.27-3.18 (m, 2H), 2.15 (t, 2H), 2.07 (s, 6H), 2.00 (s, 3H), 1.61-1.32 (m, 6H), 1.30-1.10 (m, 4H), 0.82 (t, 3H)

Example 3

4-(Dimethylamino)butyl 2-(4-((2-amino-4-methyl-6-(pentylamino)pyrimidin-5-yl)methyl)phenyl)acetate methanesulphonic acid salt

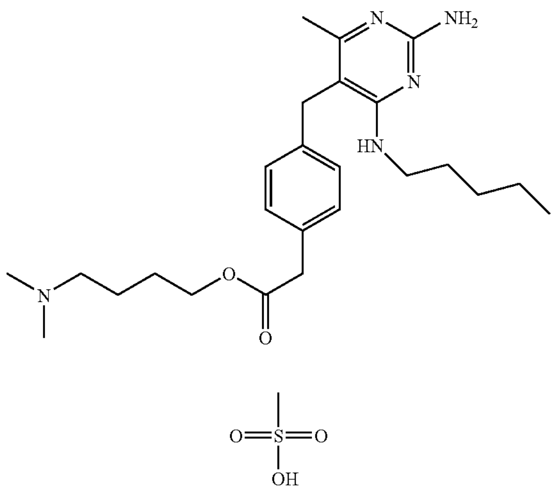

The preparation involved slurrying with diethyl ether. The stoichiometry, Compound (I) to acid, of 1:1 was confirmed by NMR.

$^1$H NMR DMSO-d6: δ 7.16 (2H, d), 7.07 (2H, d), 6.52 (2H, s), 4.02 (2H, t), 3.76 (2H, s), 3.61 (2H, s), 3.34-3.27 (2H, m), 2.69-2.60 (2H, m), 2.45 (3H, s), 2.30 (6H, s), 2.09 (3H, s), 1.61-1.40 (6H, m), 1.27-1.06 (4H, m), 0.81 (3H, t)

Example 4

4-(Dimethylamino)butyl 2-(4-((2-amino-4-methyl-6-(pentylamino)pyrimidin-5-yl)methyl)phenyl)acetate disaccharin salt (Form A)

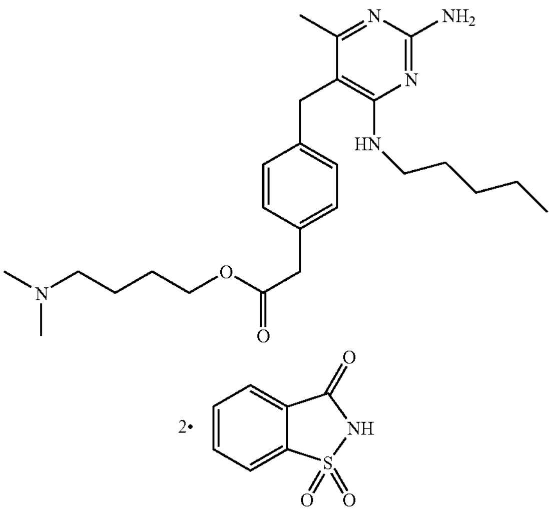

HATU (0.333 g) was added to a stirred solution of 2-(4-((2-amino-4-methyl-6-(pentylamino)pyrimidin-5-yl)methyl)phenyl)acetic acid (0.3 g), 4-(dimethylamino)butan-1-ol (0.308 g) and Hunig base (0.45 mL) in DMF (6 mL) at room temperature under a nitrogen atmosphere. The mixture was stirred at room temperature for 3 hours and then purified by RPHPLC on XBridge C8 (30×100 mm) column eluting with 0.2% aq $NH_3$ and acetonitrile. The resulting gum (225 mg) was dissolved in MeCN (5 mL) and then saccharin (186 mg) was added and the solvent evaporated under reduced pressure to leave a foam (411 mg). Slurrying (16 mg) in ethyl acetate (0.5 mL) with stirring for 7 days gave the title compound (the disaccharin salt of Compound (I) Form A), which was isolated by filtration.

The stoichiometry, Compound (I) to acid, of 1:2 was confirmed by NMR.

$^1H$ NMR DMSO-d6: δ 7.92 (t, 1H), 7.69-7.52 (m, 8H), 7.40 (s, 2H), 7.18 (d, 2H), 7.10 (d, 2H), 4.03 (t, 2H), 3.82 (s, 2H), 3.63 (s, 2H), 3.41-3.29 (m, 2H), 3.10-3.02 (m, 2H), 2.76 (s, 6H), 2.20 (s, 3H), 1.71-1.54 (m, 4H), 1.47 (quintet, 2H), 1.28-1.05 (m, 4H), 0.81 (t, 3H).

Example 4a

Alternative preparation of 4-(dimethylamino)butyl 2-(4-((2-amino-4-methyl-6-(pentylamino)pyrimidin-5-yl)methyl)phenyl)acetate disaccharin salt (Form A)

A suspension of 4-(Dimethylamino)butyl 2-(4-((2-amino-4-methyl-6-(pentylamino)pyrimidin-5-yl)methyl)phenyl) acetate (1.0 g) in EtOAc (10 mL) was heated to become a solution and then cooled to 20° C. Saccharin (0.9 g) was added to the solution and the mixture was stirred at the temperature for 3 hours. After stirred for 6 days, the resulting precipitate was collected by filtration and dried to give the disaccharin salt of Compound (I) Form A, 1.78 g.

Example 4b

Alternative preparation of 4-(dimethylamino)butyl 2-(4-((2-amino-4-methyl-6-(pentylamino)pyrimidin-5-yl)methyl)phenyl)acetate disaccharin salt (Form A)

4-(Dimethylamino)butyl 2-(4-((2-amino-4-methyl-6-(pentylamino)pyrimidin-5-yl)methyl)phenyl)acetate (0.50 g, 1.13 mmol) and saccharin (0.41 g, 2.26 mmol) were combined and MeCN (25 mL) was added. The suspension was sonicated until a clear solution was obtained. The solvent was evaporated to afford the disaccharin salt as oil. EtOAc (17 mL) was added to the oil. The oily residue did not dissolve completely at room temperature. The mixture was sonicated and formed a white suspension with some gum-like material observed on the flask wall. The mixture was stirred for 2 days and the resulting crystals collected by filtration and dried under reduced pressure to afford the disaccharin salt of Compound (I) Form A (757 mg, yield 83%).

Example 4c

Alternative preparation of 4-(dimethylamino)butyl 2-(4-((2-amino-4-methyl-6-(pentylamino)pyrimidin-5-yl)methyl)phenyl)acetate disaccharin salt (Form A)

(i) Methyl 2-(4-(cyanomethyl)benzyl)-3-oxobutanoate

A stirred mixture of methyl 3-hydroxy-2-methylenebutanoate (70.0 g), 2-(4-bromophenyl)acetonitrile (126.5 g), $PdCl_2[P(o\text{-}tol)_3]_2$ (4.2 g) and triethylamine (108.9 g) in acetonitrile (280 mL) was heated under nitrogen at 70° C. for 6 hours. The mixture was cooled to room temperature, diluted with toluene (840 mL) and water (840 mL) and stirred for 10 minutes. The organic layer was separated, washed with water (840 mL) and concentrated under reduced pressure to give the subtitle compound as a red oil, 158.7 g. This product was used in the next step without further purification.

LC-MS m/z 244 APCI−

(ii) 2-(4-((2-Amino-4-hydroxy-6-methylpyrimidin-5-yl)methyl)phenyl)acetonitrile

A stirred mixture of the crude product from step (i) and guanidine carbonate (128.1 g) in methanol (915 mL) was heated under reflux for 5 hours. The mixture was cooled to room temperature, diluted with water (923 mL) and nuetralised with acetic acid. The mixture was then cooled to 10° C. and the resulting precipitate collected by filtration, washed with methanol (501 mL) and dried under reduced pressure to give the subtitle compound as a solid, 82.4 g; $^1H$ NMR DMSO-d6: δ 10.91 (brs, 1H), 7.20-7.17 (m, 4H), 6.38 (s, 2H), 3.95 (s, 2H), 3.63 (s, 2H), 2.00 (s, 3H).

LC-MS m/z 255 APCI+

(iii) 2-(4-((2-Amino-4-((2,4,6-trimethylbenzenesulfonyl)oxy)-6-methylpyrimidin-5-yl)methyl)phenyl)acetonitrile N,N,N',N'-Tetramethyl-1,3-propanediamine (56.7 g) was added dropwise to a suspension of the product from step (ii) (85.0 g) and 2,4,6-trimethylbenzenesulfonyl chloride (87.8 g) in THF (452.9 g), and the mixture was heated at 45° C. for 7 hours. 2.5% HCl in water (1291 g) was added to the mixture, and the mixture was stirred at 5° C. for 30 minutes. The resulting precipitate was collected by filtration, washed with acetonitrile (2×68.0 g), and dried to give the crude subtitle compound as a solid. A stirred suspension of the solid in acetonitrile (654.5 g) was heated at 70° C. for 30 minutes, cooled to 5° C. and stirred at 5° C. for 30 minutes. The resulting precipitate was collected by filtration, washed with acetonitrile (2×68.0 g) and dried to give the subtitle compound as a solid, 113.1 g; $^1$H NMR CDCl3: δ 7.24 (d, 2H), 7.11 (d, 2H), 6.96 (s, 2H), 4.71 (s, 2H), 3.90 (s, 2H), 3.71 (s, 2H), 2.59 (s, 6H), 2.32 (s, 3H), 2.27 (s, 3H).

LC-MS m/z 373 multimode+

(iv) 2-(4-((2-Amino-4-methyl-6-(pentylamino)pyrimidin-5-yl)methyl)phenyl)acetonitrile Trifluoroacetic acid (27.4 g) was slowly added to a suspension of the product from step (iii) (105.0 g) and n-pentylamine (62.9 g) in butyl acetate (877.8 g) and the mixture was heated at 120° C. for 2 hours. The mixture was cooled to 20° C. and 4% aq. NaOH (997.5 g) was added to the mixture. The organic layer was separated, washed with water (997.5 g) and 10% aq. $NH_4Cl$ (997.5 g) respectively and the solvent evaporated under reduced pressure to afford a solid. The solid was dissolved in acetonitrile (221.1 g) at 50° C. and the solution was cooled to 42° C., seeded and stirred at this temperature for 1 hour. After the mixture was cooled to 5° C. and stirred at 5° C. for 1 hour, the resulting precipitate was collected by filtration, washed with acetonitrile (2x31.5 g) and dried under reduced pressure to give the subtitle compound as a solid, 52.0 g; $^1$H NMR DMSO-d6: δ 7.23 (d, 2H), 7.11 (d, 2H), 6.17 (t, 1H), 5.68 (s, 2H), 3.96 (s, 2H), 3.73 (s, 2H), 3.27-3.22 (m, 2H), 2.00 (s, 3H), 1.47-1.40 (m, 2H), 1.28-1.19 (m, 2H), 1.17-1.09 (m, 2H), 0.82 (t, 3H).

LC-MS m/z 324 multimode+

(v) 2-(4-((2-Amino-4-methyl-6-(pentylamino)pyrimidin-5-yl)methyl)phenyl)acetic acid A mixture of the product from step (iv) (51.7 g) and 5 M KOH (517 g) in ethanol (204 g) was heated at 80° C. for 4 hours. After the solvent was evaporated under reduced pressure, the residue was diluted with water (259 mL) and washed with t-butyl methyl ether (390 g) at 25° C. The solution was cooled to 5° C. and the pH of the solution was adjusted to pH 5 with conc. HCl. The resulting precipitate was collected by filtration, washed with a solution of water (200 mL) and MeCN (200 g) and dried to afford the subtitle compound as a solid, 57.0 g; containing 4.5% weight of water; $^1$H NMR DMSO-$d_6$: 7.12 (d, 2H), 7.02 (d, 2H), 6.32 (t, 1H), 5.94 (brs, 2H), 3.71 (s, 2H), 3.46 (s, 2H), 3.27-3.23 (m, 2H), 2.00 (s, 3H), 1.48-1.41 (m, 2H), 1.27-1.21 (m, 2H), 1.18-1.13 (m, 2H), 0.82 (t, 3H).

LC-MS m/z 343 multimode+

(vi) 4-(Dimethylamino)butyl 2-(4-((2-amino-4-methyl-6-(pentylamino)pyrimidin-5-yl)methyl)phenyl)acetate 4,4'-Dimethylaminobutanol (66.7 g), HOBt (30.8 g) and EDCI.HCl (43.8 g) were added to a suspension of the product of step (vii) (65.0 g) in DMF (619 g) under nitrogen at 25° C. The mixture was stirred at 45° C. for 4 hours and acidified with 2 M HCl (650 g). The mixture was washed with $CHCl_3$ (966 g), followed by 28% aq. $NH_3$ (176 g). The mixture was extracted with EtOAc (2×586 g) and the organic layer was washed with water (3×975 g). The solution was concentrated under reduced pressure to afford the is subtitle compound as a brown oil, 68.2 g; $^1$H NMR $CDCl_3$: 7.19 (d, 2H), 7.08 (d, 2H), 4.61 (brs, 2H), 4.29 (t, 1H), 4.10 (t, 2H), 3.73 (s, 2H), 3.58 (s, 2H), 3.29-3.25 (m, 2H), 2.26-2.23 (m, 2H), 2.25 (s, 3H), 2.19 (s, 6H), 1.69-1.61 (m, 2H), 1.52-1.46 (m, 2H), 1.42-1.35 (m, 2H), 1.27-1.18 (m, 2H), 1.12-1.03 (m, 2H), 0.82 (t, 3H).

LC-MS m/z 442 multimode+

(vii) 4-(Dimethylamino)butyl 2-(4-((2-amino-4-methyl-6-(pentylamino)pyrimidin-5-yl)methyl)phenyl) acetate disaccharin salt (Form A)

Saccharin (41.5 g) was added to a stirred solution of the product from step (vi) (50.0 g) in acetonitrile (150 mL). The mixture was heated to 40° C. and stirred at the temperature for 10 minutes. The mixture was diluted with EtOAc (500 mL), seeded with Form A crystals and stirred at 40° C. for 5 hours. The mixture was then cooled to 20° C. and stirred at the temperature for 2 hours. The resulting solid was collected by filtration, washed with EtOAc (200 mL) and dried under reduced pressure to give a crude sample of the subtitle compound as a white solid, 81.5 g.

The crude product obtained above (1.0 g) was dissolved in acetonitrile (2 mL), heated to 40° C., and stirred the temperature for 20 minutes. The heated solution was filtered through a paper filter (0.1 μm mesh). The filtrate was diluted with EtOAc (7 mL), seeded with Form A crystals and stirred at 40° C. for 30 minutes. The mixture was then cooled to 35° C. and stirred at for 4 hours. After the mixture was cooled to 15° C. and stirred at the temperature for 2 hours, the resulting precipitate was collected by filtration, washed with EtOAc (2 mL) and dried to give the title compound as a white solid, 0.9 g; $^1$H NMR DMSO-d6: δ 7.95 (brt, 1H), 7.68-7.63 (m, 2H), 7.62-7.56 (m, 6H), 7.19 (d, 2H), 7.15 (d, 2H), 4.03 (t, 2H), 3.82 (s, 2H), 3.63 (s, 2H), 3.38-3.33 (m, 2H), 3.07-3.02 (m, 2H), 2.76 (s, 6H), 2.20 (s, 3H), 1.69-1.55 (m, 4H), 1.51-1.43 (m, 2H), 1.27-1.17 (m, 2H), 1.16-1.07 (m, 2H), 0.80 (t, 3H).

LC-MS m/z 442 multimode+

Example 4d

Alternative Preparation of 4-(Dimethylamino)butyl 2-(4-((2-amino-4-methyl-6-(pentylamino)pyrimidin-5-yl)methyl)phenyl)acetate disaccharin salt Form A (i) Methyl 2-(4-(cyanomethyl)benzyl)-3-oxobutanoate A stirred mixture of methyl 3-hydroxy-2-methylenebutanoate (30.0 g, 0.23 mol), 2-(4-bromophenyl)acetonitrile (54.2 g, 0.28 mol), $PdCl_2[P(o\text{-}tol)_3]_2$ (1.8 g, 2 mmol) and triethylamine (46.7 g, 0.46 mol) in acetonitrile (90 g) was heated at 70° C. for 6 hours under a $N_2$ atmosphere. The mixture was cooled to 25° C., diluted with toluene (300 g) and 10% aq. acetic acid (360 g), and stirred for 10 minutes. The organic layer was separated, washed with water (360 g), and concentrated under reduced pressure to give the subtitle compound as a red oil, 67.3 g. This product was used in the next step without further purification.

LC-MS m/z 244 APCI−

(ii) 2-(4-((2-Amino-4-hydroxy-6-methylpyrimidin-5-yl)methyl)phenyl)acetonitrile

A stirred mixture of the crude product from step (i) and guanidine carbonate (36.7 g, 0.20 mol) in methanol (389 g) was heated under reflux for 7 hours. The mixture was cooled to 30° C., diluted with water (222 g), and the pH of the solution was adjusted to pH 6.5 with acetic acid. After the mixture was cooled to 5° C., the resulting precipitate was collected by filtration, washed with methanol twice (167 g, 333 g), and dried under reduced pressure to give the subtitle compound as a solid, 32.6 g.

$^1$H NMR DMSO-d6: δ 10.91 (brs, 1H), 7.20-7.17 (m, 4H), 6.38 (s, 2H), 3.95 (s, 2H), 3.63 (s, 2H), 2.00 (s, 3H).

LC-MS m/z 255 APCI+

(iii) 2-(4-((2-Amino-4-((2,4,6-triisopropylbenzene-sulfonyl)oxy)-6-methylpyrimidin-5-yl)methyl)phenyl)acetonitrile A suspension of the product from step (ii) (6.0 g, 23.6 mmol), 2,4,6-triisopropylbenzenesulfonyl chloride (9.28 g, 30.6 mmol) and DABCO (4.76 g, 42.5 mmol) in THF (48.0 g) was stirred at 30° C. for 7 hours. Water (9.6 g) was added to the mixture and the organic layer was separated and concentrated under reduced pressure to give a solid. The solid was dissolved in acetonitrile (57.0 g) and heated to 60° C. Water (36.0 g) was added to the solution and the mixture was stirred at 60° C. for 1 hour. Water (36.0 g) was added to the mixture and the mixture was cooled to 5° C. and stirred at 5° C. for 1 hour. The resulting precipitate was collected by filtration, washed duplicate with combined solution of water (9.0 g) and acetonitrile (3.6 g), and dried to give the subtitle is compound as a solid, 11.6 g.

$^1$H NMR DMSO: δ 7.32 (s, 2H), 7.23 (d, 2H, J=8.1 Hz), 7.06 (d, 2H, J=8.1 Hz), 6.54 (s, 2H), 4.01 (m, 2H), 3.98 (s, 2H), 3.78 (s, 2H), 2.97 (s, 1H), 2.21 (s, 3H), 1.23 (d, 6H, J=6.9 Hz), 1.16 (d, 12H, J=6.8 Hz).

LC-MS m/z 521 multimode+

(iv) 2-(4-((2-Amino-4-methyl-6-(pentylamino)pyrimidin-5-yl)methyl)phenyl)acetonitrile Trifluoroacetic acid (2.19 g, 19.2 mmol) was added to a suspension of the product from step (iii) (10.0 g, 19.2 mmol) and n-pentylamine (5.0 g, 57.6 mmol) in butyl acetate (65.0 g), and the mixture was heated at 120° C. for 6 hours. The mixture was cooled and concentrated under reduced pressure to give a solid. A suspension of the solid in toluene (30.0 g) was concentrated under reduced pressure again to give a solid. 5% aq. LiOH (60.0 g) was added to the solution of the solid in toluene (55.0 g) and THF (14.0 g), and the mixture was stirred at 40° C. The separated organic layer was washed with water (60.0 g) at 40° C. and concentrated under reduced pressure to afford a solid. A suspension of the obtained solid in toluene (42.0 g) was stirred at 54° C. for 1 hour and cooled to 5° C. and stirred at 5° C. for 10 hours. The resulting precipitate was collected by filtration and washed with acetonitrile (5.0 g) and water (12.0 g) respectively to give the subtitle compound as wet crystals. 5.90 g. This product was used in the next step without desiccation.

LC-MS m/z 324 multimode+

(v) 2-(4-((2-Amino-4-methyl-6-(pentylamino)pyrimidin-5-yl)methyl)phenyl)acetic acid The suspension of the wet product from step (iv) (5.90 g) in 10% aq.NaOH (34.2 g) and ethanol (24.9 g) was heated at 85° C. for 5 hours. The mixture was cooled to 25° C., and the pH of the solution was adjusted to pH 6.5 with 18% aq. acetic acid (31.1 g). The resulting precipitate was collected by filtration, washed with water (18.6 g) and acetonitrile (15.5 g) respectively, and dried to give the subtitle compound as a white solid, 4.43 g.

$^1$H NMR DMSO-$d_6$: δ 7.12 (d, 2H, J=8 Hz), 7.02 (d, 2H, J=8 Hz), 6.32 (t, 1H, J=6 Hz), 5.94 (brs, 2H), 3.71 (s, 2H), 3.46 (s, 2H), 3.27-3.23 (m, 2H), 2.00 (s, 3H), 1.48-1.41 (m, 2H), 1.27-1.21 (m, 2H), 1.18-1.13 (m, 2H), 0.82 (t, 3H, J=7 Hz).

LC-MS m/z 343 multimode+

(vi) 2-(4-((2-Amino-4-methyl-6-(pentylamino)pyrimidin-5-yl)methyl)phenyl)acetic acid hydrochloride A suspension of the product from step (v) (8.00 g, 23.4 mmol) in acetonitrile (48.0 g) was heated to 40° C., and 35% aq. HCl (2.68 g, 25.7 mmol) was slowly added to the suspension. After the mixture was stirred at 40° C. for 1 hour, isopropyl acetate (160 g) was slowly added to the mixture. The mixture was cooled to 15° C. and stirred for 1 hour. The resulting precipitate was collected by filtration, washed with combined solution of acetonitrile (5.14 g) and isopropyl acetate (13.9 g), and dried to give the subtitle compound as a white solid, 8.27 g.

$^1$H NMR DMSO-$d_6$: δ 12.31 (s, 1H), 7.98 (t, 1H, J=5 Hz), 7.17 (d, 2H, J=8 Hz), 7.08 (d, 2H, J=8 Hz), 3.81 (s, 2H), 3.51 (s, 2H), 3.38-3.34 (m, 2H), 2.19 (s, 3H), 1.51-1.44 (m, 2H), 1.25-1.16 (m, 2H), 1.15-1.07 (m, 2H), 0.81 (t, 3H, J=7 Hz).

LC-MS m/z 343 multimode+

(vii) 4-(Dimethylamino)butyl 2-(4-((2-amino-4-methyl-6-(pentylamino)pyrimidin-5-yl)methyl)phenyl) acetate (Compound (I))

The solution of the product from step (vi) (2.00 g, 5.28 mmol) and methanesulfonic acid (1.52 g, 15.8 mmol) in acetonitrile (16.0 g) was cooled to 20° C. and thionyl chloride (0.94 g, 7.92 mmol) was slowly added to the solution. After the mixture was stirred at 20° C. for 30 minutes, 4-dimethylamino-1-butanol (1.11 g, 9.50 mmol) was slowly added to the mixture. The mixture was heated to 40° C. and stirred at the temperature for 5 hours. After the reaction mixture was cooled to 20° C., ethyl acetate (18.0 g) and 25% aq. trimethylamine (18.0 g) was slowly added to the mixture. The organic layer was separated and washed respectively with 5% aq. $NH_4Cl$ (20.0 g), 1% aq. NaCl (20.0 g) and water (20.0 g). The solution of the subtitle compound was used in the next step without concentration.

LC-MS m/z 442 multimode+

(viii) 4-(Dimethylamino)butyl 2-(4-((2-amino-4-methyl-6-(pentylamino)pyrimidin-5-yl)methyl)phenyl)acetate disaccharin salt (Form A) (Compound (I) disaccharin salt (Form A))

The solution of the product from step (vii) was diluted with acetonitrile (9.3 g) and activated carbon (0.2 g) was added. The mixture was stirred at 25° C. for 30 minutes, filtered through a paper filter (1 μm mesh), and washed with acetonitrile (7.0 g). Saccharin (1.32 g, 7.21 mmol) was added to the filtrate and then the quantity of the product from step is (vii) in the solution was determined by HPLC analysis. The equivalent of saccharin for the product from step (vii) was adjusted to 2.00 molar ratio with an additional charge of saccharin (0.34 g, 1.86 mmol) and the solution was concentrated under reduced pressure. The corresponding residue was diluted with acetonitrile (4.1 g) and ethyl acetate (9.6 g), heated to 40° C. and seeded with form A crystals of the title compound. After the mixture was stirred at 40° C. for 1 hour, ethyl acetate (10.6 g) was added. The mixture was stirred at 40° C. for 1 hour, cooled to 10° C. and stirred for 2 hours. The resulting solid was collected by filtration, washed with combined solution of acetonitrile (0.8 g) and ethyl acetate (3.0 g), and dried under reduced pressure to give a crude sample of the subtitle compound as a white solid, 3.11 g.

The crude product obtained above (3.00 g) was suspended to acetonitrile (4.5 g) and the suspension was heated to 40° C. The resulting solution was filtered through a paper filter (1 μm mesh) and the filtrate was diluted with ethyl acetate (12.0 g). The mixture was seeded with Form A crystals of the disaccharin salt, and stirred for 1.5 hours. The suspension was diluted with ethyl acetate (18.0 g), stirred for 1 hour, and then cooled to 10° C. and stirred for 3 hours. The resulting solid was collected by filtration, washed with combined solution of acetonitrile (0.8 g) and ethyl acetate (3.9 g) and dried under reduced pressure to give the title compound as a white solid, 2.54 g.

$^1$H NMR DMSO-d6: δ 7.95 (brt, 1H, J=6 Hz), 7.68-7.63 (m, 2H), 7.62-7.56 (m, 6H), 7.19 (d, 2H, J=8 Hz), 7.15 (d, 2H, J=8 Hz), 4.03 (t, 2H, J=6 Hz), 3.82 (s, 2H), 3.63 (s, 2H), 3.38-3.33 (m, 2H), 3.07-3.02 (m, 2H), 2.76 (s, 6H), 2.20 (s, 3H), 1.69-1.55 (m, 4H), 1.51-1.43 (m, 2H), 1.27-1.17 (m, 2H), 1.16-1.07 (m, 2H), 0.80 (t, 3H, J=7 Hz).

LC-MS m/z 442 multimode+

Example 5

4-(Dimethylamino)butyl 2-(4-((2-amino-4-methyl-6-(pentylamino)pyrimidin-5-yl)methyl)phenyl)acetate disaccharin salt (Form B)

4-(Dimethylamino)butyl 2-(4-((2-amino-4-methyl-6-(pentylamino)pyrimidin-5-yl)methyl)phenyl)acetate (300 mg, 0.68 mmol) and saccharin (249 mg, 1.36 mmol) were combined and acetonitrile (15 mL) was added. The suspension was sonicated until a clear solution was obtained. The solvent was evaporated, the residue was redissolved in ethyl acetate (10 mL) and stirred for 3 days at room temperature to afford the disaccharin salt of is Compound (I) Form B; $^1$H NMR DMSO-d6: δ 7.91 (1H, s), 7.69-7.54 (8H, m), 7.39 (2H, s), 7.18 (2H, d), 7.10 (2H, d), 4.04 (2H, t), 3.82 (2H, s), 3.63 (2H, s), 3.39-3.33 (2H, m), 3.04 (2H, t), 2.75 (6H, s), 2.20 (3H, s), 1.71-1.54 (4H, m), 1.53-1.42 (2H, m), 1.28-1.17 (2H, m), 1.16-1.06 (2H, m), 0.81 (3H, t).

Example 5a

Alternative Preparation of 4-(dimethylamino)butyl 2-(4-((2-amino-4-methyl-6-(pentylamino)pyrimidin-5-yl)methyl)phenyl)acetate disaccharin salt (Form B)

4-(Dimethylamino)butyl 2-(4-((2-amino-4-methyl-6-(pentylamino)pyrimidin-5-yl)methyl)phenyl)acetate (400 mg, 0.91 mmol) dissolved in ethyl acetate (10 mL) and saccharin (332 mg, 1.81 mmol) dissolved and sonicated in ethyl acetate (40 mL) were combined. The solvent was evaporated, the residue was slurried in ethyl acetate (10 mL) and stirred for 3 days at room temperature to afford the disaccharin salt of Compound (I) Form B.

Example 5b

Alternative Preparation of 4-(dimethylamino)butyl 2-(4-((2-amino-4-methyl-6-(pentylamino)pyrimidin-5-yl)methyl)phenyl)acetate disaccharin salt (Form B)

4-(Dimethylamino)butyl 2-(4-((2-amino-4-methyl-6-(pentylamino)pyrimidin-5-yl)methyl)phenyl)acetate (523 mg, 1.18 mmol) was dissolved in 8 mL of acetonitrile. In a separate flask saccharin (434 mg, 2.37 mmol) was combined with 10 mL of acetonitrile (this resulted in a slurry), which was added to the Compound (I)-acetonitrile mixture. The mixture was stirred until a clear solution was obtained at room temperature (10 minutes). The solvent was evaporated. To this gummy residue was added EtOAc (25 mL) and the mixture seeded with 0.1 mg of Compound (I) disaccharin salt Form B. The mixture was stirred for 3 days at room temperature, filtered and dried (643 mg) to afford the disaccharin salt of Compound (I) Form B.

The stoichiometry, Compound (I) to acid, of 1:2 was confirmed by NMR.

1H NMR (400 MHz, DMSO) d 7.93 (t, 1H), 7.68-7.54 (m, 10H), 7.3-7.5 (m, 2H), 7.18 (d, 2H), 7.10 (d, 2H), 4.03 (q, 2H), 3.82 (s, 2H), 3.63 (s, 2H), 3.10-3.01 (m, 2H), 2.76 (s, 6H), 2.19 (s, 3H), 1.71-1.54 (m, 4H), 1.52-1.42 (m, 2H), 1.31-1.06 (m, 5H), 0.81 (t, 3H).

Example 6

4-(Dimethylamino)butyl 2-(4-((2-amino-4-methyl-6-(pentylamino)pyrimidin-5-yl)methyl)phenyl)acetate di-1-hydroxy-2-naphthoic acid salt

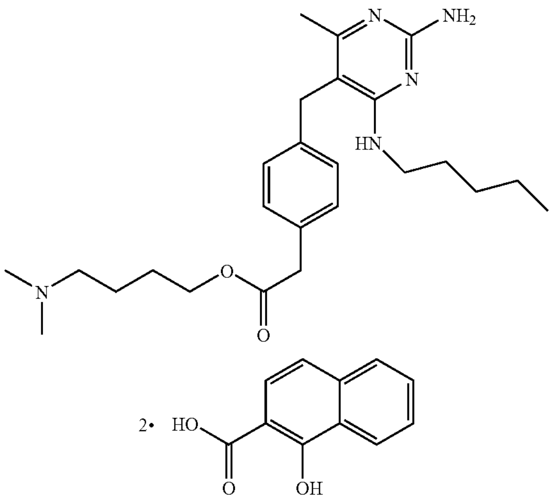

The preparation involved slurrying with ethyl acetate. The stoichiometry, Compound (I) to acid, of 1:2 was confirmed by NMR.

$^1$H NMR DMSO-d6: δ 8.20 (d, 2H), 7.98 (s, 2H), 7.80-7.71 (m, 5H), 7.51-7.45 (m, 2H), 7.43-7.37 (m, 2H), 7.16 (d, 2H), 7.12-7.05 (m, 4H), 4.03 (t, 2H), 3.82 (s, 2H), 3.60 (s, 2H), 3.40-3.32 (m, 2H), 2.99 (t, 2H), 2.71 (s, 6H), 2.24 (s, 3H), 1.72-1.55 (m, 4H), 1.48 (quintet, 2H), 1.28-1.05 (m, 4H), 0.81 (t, 3H)

Example 7

4-(Dimethylamino)butyl 2-(4-((2-amino-4-methyl-6-(pentylamino)pyrimidin-5-yl)methyl)phenyl)acetate mono-(2,5-dichlorobenzenesulphonic acid) salt

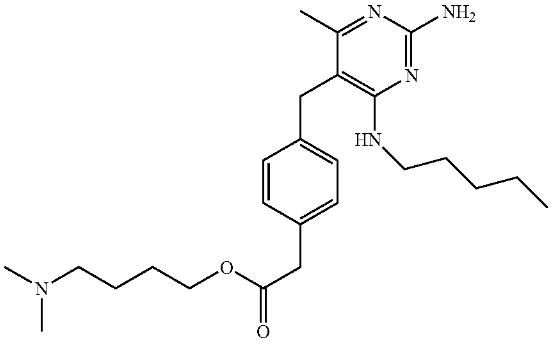

-continued

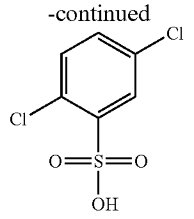

The preparation involved slurrying with methyl tent-butyl ether. The stoichiometry, Compound (I) to acid, of 1:1 was confirmed by NMR.

$^1$H NMR DMSO-d6: δ 7.83 (2H, d), 7.44-7.37 (4H, m), 7.18 (2H, d), 7.09 (2H, d), 4.03 (2H, t), 3.81 (2H, s), 3.63 (2H, s), 3.38-3.33 (2H, m), 2.99-2.92 (2H, m), 2.69 (6H, s), 2.16 (3H, s), 1.67-1.55 (4H, m), 1.51-1.42 (2H, m), 1.27-1.18 (2H, m), 1.15-1.07 (2H, m), 0.81 (3H, t)

Example 8

4-(Dimethylamino)butyl 2-(4-((2-amino-4-methyl-6-(pentylamino)pyrimidin-5-yl)methyl)phenyl)acetate di-(2,5-dichlorobenzenesulphonic acid) salt The preparation involved slurrying with ethyl acetate.

Example 9

4-(Dimethylamino)butyl 2-(4-((2-amino-4-methyl-6-(pentylamino)pyrimidin-5-yl)methyl)phenyl)acetate 1,5-naphthalenedisulphonic acid salt (Form A)

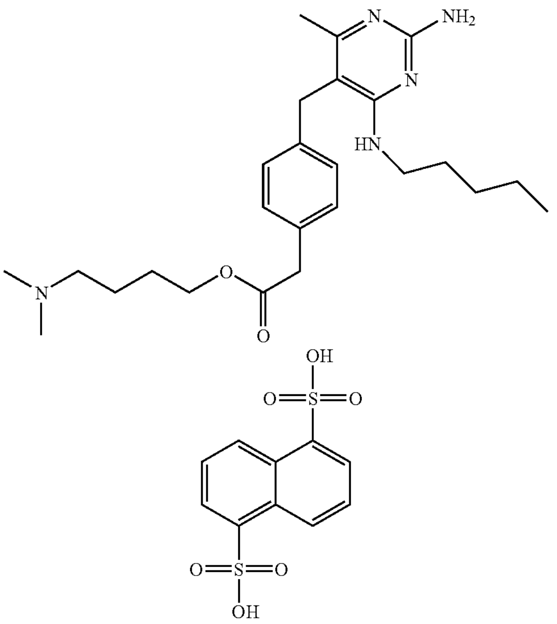

The preparation involved slurrying with dimethoxyethane. The stoichiometry, Compound (I) to acid, of 1:1 was confirmed by NMR.

$^1$H NMR DMSO-d6: δ 8.86 (2H, d), 7.92 (2H, dd), 7.40 (2H, dd), 7.18 (2H, d), 7.09 (2H, d), 4.03 (2H, t), 3.81 (2H, s), 3.63 (2H, s), 3.40-3.33 (2H, m), 3.07-3.01 (2H, m), 2.75 (6H, s), 2.18 (3H, s), 1.69-1.53 (4H, m), 1.52-1.41 (2H, m), 1.28-1.17 (2H, m), 1.15-1.05 (2H, m), 0.81 (3H, t)

Example 10

4-(Dimethylamino)butyl 2-(4-((2-amino-4-methyl-6-(pentylamino)pyrimidin-5-yl)methyl)phenyl)acetate 1,5-naphthalenedisulphonic acid salt (Form B)

The preparation involved slurrying with tetrahydrofuran. The stoichiometry, Compound (I) to acid, of 1:1 was confirmed by NMR.

$^1$H NMR DMSO-d6: δ 11.87 (2H, s), 9.18 (1H, s), 8.87 (2H, d), 7.94 (2H, d), 7.41 (2H, dd), 7.18 (2H, d), 7.09 (2H, d), 4.03 (2H, t), 3.81 (2H, s), 3.60 (2H, s), 3.39-3.33 (2H, m), 3.03 (2H, t), 2.74 (6H, s), 2.17 (3H, s), 1.79-1.73 (2H, m), 1.67-1.53 (2H, m), 1.50-1.42 (2H, m), 1.27-1.17 (2H, m), 1.15-1.05 (2H, m), 0.80 (3H, t)

Example 11

4-(Dimethylamino)butyl 2-(4-((2-amino-4-methyl-6-(pentylamino)pyrimidin-5-yl)methyl)phenyl)acetate citric acid salt (Form A)

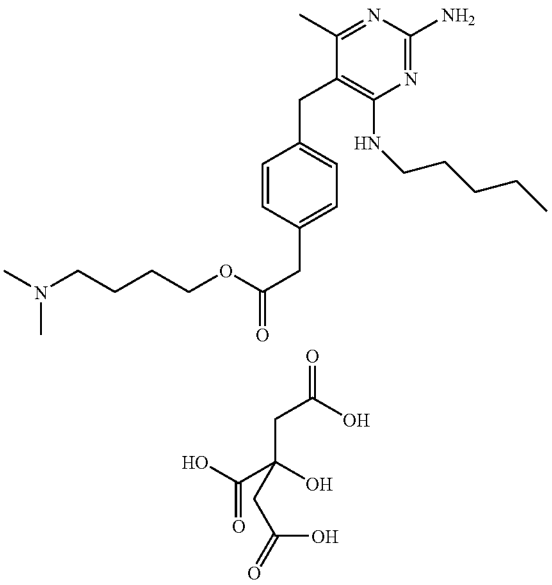

The preparation involved slurrying with acetonitrile. The stoichiometry, Compound (I) to acid, of 1:1 was confirmed by NMR.

$^1$H NMR MeOD: δ 7.13 (2H, d), 7.01 (2H, d), 4.01 (2H, t), 3.74 (2H, s), 3.51 (2H, s), 3.35 (2H, t), 2.87 (2H, t), 2.68 (2H, d), 2.61 (6H, s), 2.58 (2H, d), 2.14 (3H, s), 1.64-1.51 (4H, m), 1.47-1.38 (2H, m), 1.24-1.13 (2H, m), 1.11-0.99 (2H, m), 0.76 (3H, t)

Example 12

4-(Dimethylamino)butyl 2-(4-((2-amino-4-methyl-6-(pentylamino)pyrimidin-5-yl)methyl)phenyl)acetate citric acid salt (Form B)

The preparation involved slurrying with tetrahydrofuran. The stoichiometry, is Compound (I) to acid, of 1:1 was confirmed by NMR.

$^1$H NMR MeOD: δ 7.22 (2H, d), 7.10 (2H, d), 4.10 (2H, t), 3.82 (2H, s), 3.60 (2H, s), 3.43 (2H, t), 2.98 (2H, t), 2.77 (2H, d), 2.72 (6H, s), 2.67 (2H, d), 2.24 (3H, s), 1.75-1.61 (4H, m), 1.55-1.46 (2H, m), 1.31-1.22 (2H, m), 1.19-1.09 (2H, m), 0.84 (3H, t),

Example 13

4-(Dimethylamino)butyl 2-(4-((2-amino-4-methyl-6-(pentylamino)pyrimidin-5-yl)methyl)phenyl)acetate phosphoric acid salt

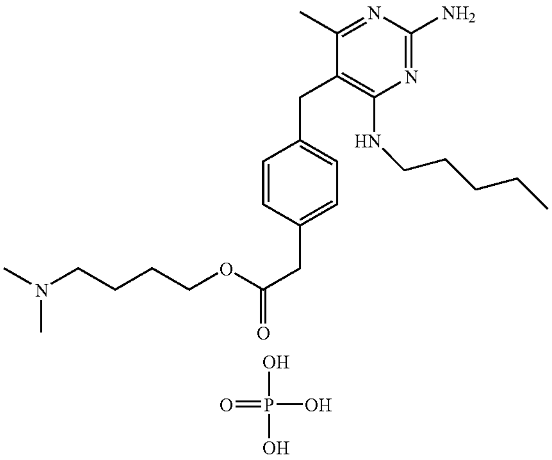

The preparation involved slurrying with dichloromethane.

Example 14

4-(Dimethylamino)butyl 2-(4-((2-amino-4-methyl-6-(pentylamino)pyrimidin-5-yl)methyl)phenyl)acetate diphosphoric acid salt The preparation involved slurrying with acetonitrile. The (di-) stoichiometry of the phosphate counter ion was confirmed by addition of trimethylphosphate. Proton and phosphorus spectra were acquired under assay conditions and the integrals of compound and trimethylphosphate accurately compared to determine the stoichiometry.

$^1$H NMR DMSO-d6: δ 7.16 (2H, d), 7.06 (2H, d), 6.92 (2H, s), 4.01 (2H, t), 3.75 (2H, s), 3.67 (18H, s), 3.60 (2H, s), 3.31-3.28 (2H, m), 2.42-2.39 (2H, t), 2.26 (6H, s), 2.08 (3H, s), 1.58-1.52 (2H, m), 1.49-1.41 (4H, m), 1.27-1.20 (2H, m), 1.17-1.11 (2H, m), 0.82 (3H, t)

$^{31}$P NMR DMSO-d6: δ 1.90 ($(CH_3O)_3PO$), −0.29 ($OP(OH)_2O^-$)

Example 15

4-(Dimethylamino)butyl 2-(4-((2-amino-4-methyl-6-(pentylamino)pyrimidin-5-yl)methyl)phenyl)acetate fumaric acid salt

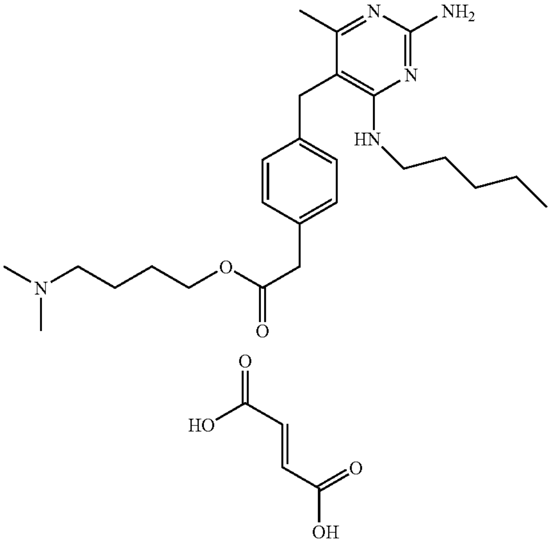

The preparation involved slurrying with acetonitrile. The stoichiometry, Compound (I) to acid, of 1:1 was confirmed by NMR.

$^1$H NMR DMSO-d6: δ 7.15 (d, 2H), 7.06 (d, 2H), 6.81 (s, 2H), 6.51 (s, 2H), 4.01 (t, 2H), 3.75 (s, 2H), 3.59 (s, 2H), 3.31-3.26 (m, 2H), 2.33 (t, 2H), 2.20 (s, 6H), 2.08 (s, 3H), 1.59-1.38 (m, 6H), 1.29-1.07 (m, 4H), 0.82 (t, 3H)

Example 16

4-(Dimethylamino)butyl 2-(4-((2-amino-4-methyl-6-(pentylamino)pyrimidin-5-yl)methyl)phenyl)acetate L-tartaric acid salt

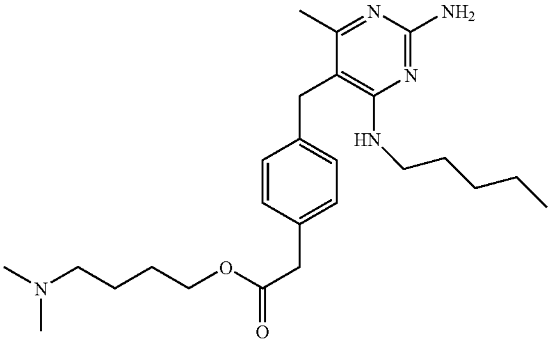

-continued

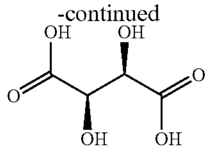

The preparation involved slurrying with acetonitrile. The stoichiometry, Compound (I) to acid, of 1:1 was confirmed by NMR.

$^1$H NMR DMSO-d6: δ 7.15 (2H, d), 7.06 (2H, d), 6.78 (1H, s), 6.43 (2H, s), 4.02 (2H, t), 3.94 (2H, s), 3.75 (2H, s), 3.60 (2H, s), 3.32-3.25 (2H, m), 2.57-2.45 (2H, m), 2.30 (6H, s), 2.07 (3H, s), 1.61-1.40 (6H, m), 1.31-1.09 (4H, m), 0.82 (3H, t)

Example 17

4-(Dimethylamino)butyl 2-(4-((2-amino-4-methyl-6-(pentylamino)pyrimidin-5-yl)methyl)phenyl)acetate succinic acid salt

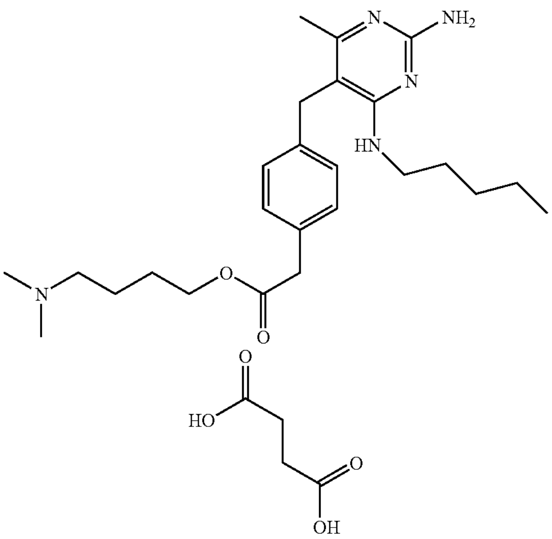

The preparation involved slurrying with diethyl ether. The stoichiometry, Compound (I) to acid, of 1:1 was confirmed by NMR.

$^1$H NMR DMSO-d6: δ 7.14 (2H, d), 7.05 (2H, d), 6.55-6.46 (1H, m), 6.12 (2H, s), 4.01 (2H, t), 3.73 (2H, s), 3.59 (2H, s), 3.31-3.23 (2H, m), 2.35 (4H, s), 2.29 (2H, t), 2.18 (6H, s), 2.03 (3H, s), 1.63-1.50 (2H, m), 1.50-1.37 (4H, m), 1.31-1.07 (4H, m), 0.82 (3H, t)

Example 18

4-(Dimethylamino)butyl 2-(4-((2-amino-4-methyl-6-(pentylamino)pyrimidin-5-yl)methyl)phenyl)acetate disuccinic acid salt The preparation involved slurrying with methyl tent-butyl ether. The stoichiometry, Compound (I) to acid, of 1:2 was confirmed by NMR.

$^1$H NMR DMSO-d6: δ 7.15 (2H, d), 7.06 (2H, d), 6.56-6.51 (1H, m), 6.12 (2H, s), 4.01 (2H, t), 3.73 (2H, s), 3.59 (2H, s), 3.31-3.24 (2H, m), 2.40-2.31 (10H, m), 2.22 (6H, s), 2.04 (3H, s), 1.59-1.51 (2H, m), 1.49-1.39 (4H, m), 1.28-1.10 (4H, m), 0.82 (3H, t)

Example 19

4-(Dimethylamino)butyl 2-(4-((2-amino-4-methyl-6-(pentylamino)pyrimidin-5-yl)methyl)phenyl)acetate difumaric acid salt

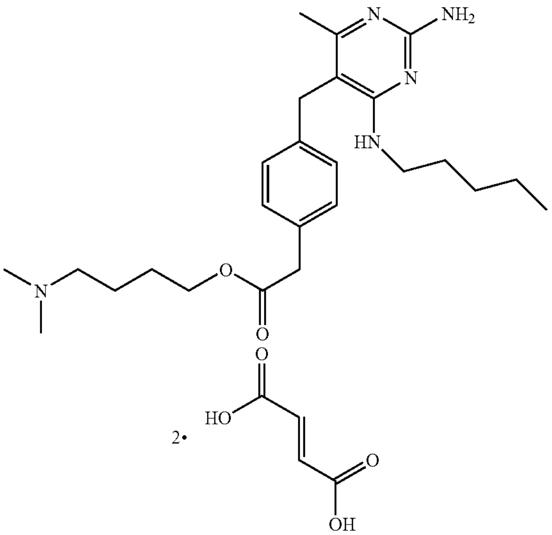

To 4-(dimethylamino)butyl 2-(4-((2-amino-4-methyl-6-(pentylamino)pyrimidin-5-yl)methyl)phenyl)acetate (200 mg, 0.45 mmol) dissolved in acetonitrile (4 mL) was added fumaric acid (105 mg, 2 molar equivalents) pre-dissolved in THF. The resulting mixture was concentrated in vacuo to a solid and diethyl ether (2 mL) was added and stirred for 7 days to afford the difumaric acid salt of Compound (I).

Example 19a

Alternative Preparation of 4-(dimethylamino)butyl 2-(4-((2-amino-4-methyl-6-(pentylamino)pyrimidin-5-yl)methyl)phenyl)acetate difumaric acid salt To 4-(dimethylamino)butyl 2-(4-((2-amino-4-methyl-6-(pentylamino)pyrimidin-5-yl)methyl)phenyl)acetate (100 mg, 0.23 mmol) dissolved in acetonitrile (4 mL) was added solid fumaric acid (105 mg, 2 molar equivalents). The resulting mixture was concentrated in vacuo to a solid and diethyl ether (2 mL) was added and stirred for 7 days to afford the difumaric acid salt of Compound (I).

The stoichiometry, Compound (I) to acid, of 1:2 was confirmed by NMR.

$^1$H NMR (299.947 MHz, DMSO) δ 7.64 (s, 2H), 7.31-7.12 (m, 3H), 7.08 (d, 2H), 6.54 (s, 4H), 4.02 (t, 2H), 3.77 (s, 2H), 3.61 (s, 2H), 3.38-3.26 (m, 2H), 2.39-2.22 (m, 8H), 2.13 (s, 3H), 1.61-1.37 (m, 6H), 1.30-1.07 (m, 4H), 0.82 (t, 3H).

Example 19b

Alternative Preparation of 4-(dimethylamino)butyl 2-(4-((2-amino-4-methyl-6-(pentylamino)pyrimidin-5-yl)methyl)phenyl)acetate difumaric acid salt Fumaric acid (52.6 mg) was added to a stirred solution of 4-(dimethylamino)butyl 2-(4-((2-amino-4-methyl-6-(pentylamino)pyrimidin-5-yl)methyl)phenyl)acetate (100.0 mg) in ethanol (0.6 ml). The solution was diluted with $^{i}$PrOAc (0.6 ml) and stirred at 25° C. for 5 h. The resulting precipitate was collected by filtration, washed with combined solution with $^{i}$PrOAc (0.6 ml) and ethanol (0.6 ml), and dried under reduced pressure to give the title compound as a white solid, 125.6 mg.

$^{1}$H NMR DMSO-d6: δ 7.17 (d, 2H, J=8 Hz), 7.07 (d, 2H, J=8 Hz), 6.52 (s, 4H), 4.01 (t, 2H, J=6 Hz), 3.77 (s, 2H), 3.60 (s, 2H), 3.34-3.29 (m, 2H), 2.56-2.45 (m), 2.34 (s, 6H), 2.13 (s, 3H), 1.59-1.52 (m, 2H), 1.49-1.42 (m, 4H), 1.28-1.18 (m, 2H), 1.16-1.09 (m, 2H), 0.81 (t, 3H, J=7 Hz).

LC-MS m/z 442 multimode+

Example 19c

Alternative Preparation of 4-(dimethylamino)butyl 2-(4-((2-amino-4-methyl-6-(pentylamino)pyrimidin-5-yl)methyl)phenyl)acetate difumaric acid salt Fumaric acid (31.6 g) was added to a stirred solution of the product from step (vi) in Example 4c (60.0 g) in ethanol (360 mL). The mixture was heated to 30° C. and stirred at the temperature for 30 minutes. The solution was diluted with $^{i}$PrOAc (180 mL), seeded with crystals of the difumaric acid salt and stirred at 30° C. for 2.5 hours. The mixture was diluted with additional $^{i}$PrOAc (180 mL), cooled to 20° C., and stirred at the temperature for 1 hour. The resulting precipitate was collected by filtration, washed with a solution of $^{i}$PrOAc (120 mL) and ethanol (90 mL), washed with $^{i}$PrOAc (120 mL) and dried under reduced pressure to give the title compound as a white solid, 81.9 g; $^{1}$H NMR DMSO-d6: δ 7.16 (d, 2H), 7.07 (d, 2H), 6.53 (s, 4H), 4.01 (t, 2H), 3.76 (s, 2H), 3.60 (s, 2H), 3.33-3.28 (m, 2H), 2.43 (t, 2H), 2.28 (s, 6H), 2.11 (s, 3H), 1.59-1.52 (m, 2H), 1.49-1.42 (m, 4H), 1.28-1.18 (m, 2H), 1.17-1.12 (m, 2H), 0.81 (t, 3H). LC-MS m/z 442 multimode+

Example 20

X-Ray Powder Diffraction Analyses

General Procedures

X-ray powder diffraction (XRPD) analyses may be performed on samples prepared according to standard methods (see for example Giacovazzo et al., eds., Fundamentals of Crystallography, Oxford University Press (1992); Jenkins & Snyder, eds., Introduction to X-Ray Powder Diffractometry, John Wiley & Sons, New York (1996); Bunn, ed., Chemical Crystallography, Clarendon Press, London (1948); and Klug & Alexander eds., X-ray Diffraction Procedures, John Wiley & Sons, New York (1974)).

X-ray powder diffraction patterns of the salts described in Examples 1 to 19 above (in is anhydrous form) were obtained as described below:

A Bragg-Brentano parafocusing powder X-ray diffractometer using monochromatic CuKα radiation (45 kV and 40 mA) was used for the analyses. The primary optics contained soller slits and an automatic divergence slit. Flat samples were prepared on zero background plates that were rotated during the measurements. The secondary optics contained soller slits, an automatic anti scatter slit, a receiving slit and a monochromator. The diffracted signal was detected with a proportional xenon-filled detector. Diffraction patterns were collected between 2°≦2θ (theta)≦40° in a continuous scan mode with 100-second exposure per 0.02°. Raw data were stored electronically. Evaluation was performed on raw or smoothed diffraction patterns.

A Panalytical X'pert MPD θ-θ diffractometer in reflection mode was used for the above-mentioned measurements. A person skilled in the art can set up instrumental parameters for a powder X-ray diffractometer so that diffraction data comparable to the data presented can be collected. The results obtained are shown in FIGS. 1 to 19. Tables I to XIX below each list the 2θ (2 theta) values (Accuracy: +/−0.1° 2Ø), d-spacings and the relative intensities of the peaks shown in the X-ray diffraction patterns of respectively FIGS. 1 to 19.

TABLE I

XRPD of Example 1 (Benzoic acid salt)

| 2Ø (°) | d-spacing (Å) | Relative Intensity (%) |
|---|---|---|
| 6.3 | 14.06 | 37 |
| 7.2 | 12.29 | 17 |
| 9.3 | 9.51 | 32 |
| 9.8 | 9.06 | 4 |
| 12.6 | 7.02 | 17 |
| 13.6 | 6.53 | 7 |
| 13.8 | 6.41 | 8 |
| 15.1 | 5.85 | 11 |
| 15.6 | 5.69 | 18 |
| 15.9 | 5.57 | 2 |
| 17.8 | 4.98 | 25 |
| 18.3 | 4.86 | 3 |
| 18.6 | 4.76 | 4 |
| 19.5 | 4.55 | 7 |
| 19.6 | 4.53 | 6 |
| 19.8 | 4.48 | 17 |
| 20.6 | 4.32 | 5 |
| 21.1 | 4.22 | 9 |
| 21.3 | 4.18 | 10 |
| 21.7 | 4.10 | 5 |
| 22.2 | 4.00 | 18 |
| 23.0 | 3.86 | 4 |
| 23.3 | 3.82 | 5 |
| 23.8 | 3.74 | 100 |
| 24.5 | 3.63 | 18 |
| 25.2 | 3.54 | 3 |
| 25.5 | 3.49 | 3 |
| 27.3 | 3.27 | 3 |
| 28.9 | 3.09 | 2 |

TABLE II

XRPD of Example 2 (Trans-Cinnamic salt)

| 2Ø (°) | d-spacing (Å) | Relative Intensity (%) |
|---|---|---|
| 3.9 | 22.55 | 100 |
| 6.1 | 14.60 | 1 |
| 9.2 | 9.63 | 1 |
| 11.2 | 7.92 | 1 |
| 13.6 | 6.52 | 1 |
| 15.6 | 5.66 | 2 |
| 17.9 | 4.96 | 2 |
| 19.6 | 4.53 | 3 |
| 20.3 | 4.37 | 4 |
| 20.6 | 4.32 | 3 |
| 22.8 | 3.90 | 1 |
| 26.5 | 3.36 | 1 |

TABLE III

XRPD of Example 3 (Methanesulphonic acid salt)

| 2Ø (°) | d-spacing (Å) | Relative Intensity (%) |
|---|---|---|
| 5.6 | 15.64 | 100 |
| 8.5 | 10.39 | 35 |
| 8.9 | 9.97 | 15 |
| 11.3 | 7.86 | 31 |
| 12.9 | 6.86 | 8 |
| 13.4 | 6.59 | 68 |
| 14.2 | 6.23 | 7 |
| 14.9 | 5.95 | 12 |

TABLE III-continued

| XRPD of Example 3 (Methanesulphonic acid salt) | | |
|---|---|---|
| 2Ø (°) | d-spacing (Å) | Relative Intensity (%) |
| 15.8 | 5.62 | 48 |
| 16.2 | 5.46 | 17 |
| 17.0 | 5.22 | 16 |
| 18.1 | 4.89 | 15 |
| 18.6 | 4.77 | 21 |
| 18.9 | 4.69 | 6 |
| 19.6 | 4.52 | 24 |
| 19.9 | 4.45 | 8 |
| 20.6 | 4.31 | 20 |
| 20.9 | 4.25 | 31 |
| 21.4 | 4.15 | 12 |
| 21.7 | 4.10 | 34 |
| 21.9 | 4.06 | 9 |
| 22.1 | 4.02 | 11 |
| 22.4 | 3.97 | 22 |
| 22.6 | 3.94 | 23 |
| 22.8 | 3.89 | 17 |
| 23.5 | 3.77 | 6 |
| 24.7 | 3.60 | 6 |
| 24.9 | 3.57 | 12 |
| 25.6 | 3.48 | 14 |
| 26.1 | 3.42 | 18 |
| 27.3 | 3.27 | 11 |
| 27.9 | 3.20 | 6 |
| 28.3 | 3.15 | 9 |

TABLE IV

| XRPD of Example 4 (Disaccharin salt - Form A) | | |
|---|---|---|
| 2Ø (°) | d-spacing (Å) | Relative Intensity (%) |
| 6.9 | 12.79 | 15 |
| 9.2 | 9.67 | 31 |
| 10.3 | 8.64 | 14 |
| 10.8 | 8.20 | 91 |
| 11.4 | 7.78 | 16 |
| 12.3 | 7.22 | 4 |
| 12.8 | 6.95 | 37 |
| 13.9 | 6.40 | 100 |
| 14.6 | 6.08 | 9 |
| 14.9 | 5.96 | 23 |
| 15.2 | 5.87 | 25 |
| 15.4 | 5.75 | 16 |
| 15.9 | 5.56 | 21 |
| 16.7 | 5.30 | 32 |
| 16.9 | 5.24 | 7 |
| 17.4 | 5.09 | 28 |
| 18.0 | 4.94 | 25 |
| 18.1 | 4.90 | 39 |
| 18.3 | 4.84 | 41 |
| 18.7 | 4.74 | 27 |
| 20.6 | 4.32 | 51 |
| 20.8 | 4.28 | 69 |
| 21.1 | 4.20 | 14 |
| 21.3 | 4.18 | 13 |
| 21.5 | 4.14 | 8 |
| 21.6 | 4.11 | 16 |
| 22.9 | 3.88 | 17 |
| 23.4 | 3.79 | 48 |
| 23.6 | 3.76 | 52 |
| 24.0 | 3.71 | 25 |
| 24.4 | 3.65 | 46 |
| 25.8 | 3.46 | 12 |
| 26.4 | 3.37 | 6 |
| 26.9 | 3.32 | 8 |
| 28.0 | 3.18 | 10 |
| 29.2 | 3.06 | 4 |
| 29.8 | 2.99 | 7 |

TABLE V

| XRPD of Example 5 (Disaccharin salt - Form B) | | |
|---|---|---|
| 2Ø (°) | d-spacing (Å) | Relative Intensity (%) |
| 3.5 | 24.96 | 68 |
| 6.2 | 14.13 | 7 |
| 7.0 | 12.70 | 58 |
| 10.4 | 8.48 | 11 |
| 10.8 | 8.16 | 8 |
| 12.0 | 7.38 | 69 |
| 12.5 | 7.10 | 100 |
| 13.9 | 6.37 | 27 |
| 16.4 | 5.42 | 47 |
| 17.3 | 5.14 | 28 |
| 17.5 | 5.06 | 29 |
| 18.1 | 4.90 | 16 |
| 19.8 | 4.49 | 28 |
| 20.8 | 4.26 | 23 |
| 23.1 | 3.85 | 29 |
| 24.4 | 3.65 | 19 |
| 25.8 | 3.45 | 13 |

TABLE VI

| XRPD of Example 6 (Di-1-hydroxy-2-naphthoic acid salt) | | |
|---|---|---|
| 2Ø (°) | d-spacing (Å) | Relative Intensity (%) |
| 8.3 | 10.65 | 100 |
| 9.5 | 9.33 | 35 |
| 11.0 | 8.08 | 10 |
| 11.5 | 7.70 | 22 |
| 11.8 | 7.51 | 28 |
| 12.4 | 7.12 | 6 |
| 12.8 | 6.92 | 33 |
| 13.2 | 6.72 | 12 |
| 13.6 | 6.52 | 37 |
| 14.3 | 6.19 | 14 |
| 15.0 | 5.90 | 7 |
| 15.7 | 5.65 | 20 |
| 16.6 | 5.34 | 82 |
| 16.9 | 5.26 | 39 |
| 17.7 | 5.00 | 19 |
| 18.1 | 4.89 | 9 |
| 18.6 | 4.76 | 6 |
| 19.4 | 4.58 | 55 |
| 20.6 | 4.30 | 39 |
| 21.2 | 4.18 | 14 |
| 22.3 | 3.98 | 16 |
| 22.9 | 3.89 | 32 |
| 23.1 | 3.85 | 49 |
| 23.4 | 3.81 | 62 |
| 26.0 | 3.43 | 37 |
| 27.4 | 3.26 | 8 |
| 28.9 | 3.09 | 5 |

TABLE VII

| XRPD of Example 7 (2,5-Dichlorobenzenesulphonic acid salt) | | |
|---|---|---|
| 2Ø (°) | d-spacing (Å) | Relative Intensity (%) |
| 3.2 | 27.25 | 100 |
| 4.4 | 20.24 | 32 |
| 4.9 | 18.01 | 42 |
| 6.4 | 13.80 | 33 |
| 7.0 | 12.64 | 14 |
| 8.7 | 10.16 | 12 |
| 11.8 | 7.52 | 13 |
| 14.0 | 6.31 | 14 |
| 14.6 | 6.05 | 17 |
| 16.6 | 5.34 | 8 |
| 19.2 | 4.63 | 25 |
| 19.6 | 4.53 | 20 |
| 22.3 | 3.99 | 8 |

TABLE VIII

XRPD of Example 8 (Di-2,5-dichlorobenzenesulphonic acid salt)

| 2Ø (°) | d-spacing (Å) | Relative Intensity (%) |
|---|---|---|
| 3.3 | 26.99 | 100 |
| 4.5 | 19.65 | 42 |
| 6.4 | 13.86 | 44 |
| 8.7 | 10.14 | 26 |
| 11.1 | 7.95 | 22 |
| 14.2 | 6.24 | 35 |
| 16.5 | 5.37 | 25 |
| 20.0 | 4.43 | 58 |
| 21.1 | 4.21 | 27 |
| 22.3 | 3.99 | 29 |
| 25.8 | 3.44 | 22 |

TABLE IX

XRPD of Example 9 (1,5-naphthalenedisulphonic acid salt - Form A)

| 2Ø (°) | d-spacing (Å) | Relative Intensity (%) |
|---|---|---|
| 4.0 | 22.03 | 17 |
| 7.9 | 11.14 | 100 |
| 9.2 | 9.57 | 11 |
| 10.0 | 8.80 | 22 |
| 10.2 | 8.67 | 24 |
| 10.7 | 8.23 | 15 |
| 12.1 | 7.28 | 10 |
| 15.2 | 5.82 | 35 |
| 15.7 | 5.65 | 54 |
| 17.0 | 5.22 | 12 |
| 18.3 | 4.84 | 11 |
| 19.1 | 4.64 | 16 |
| 19.4 | 4.56 | 36 |
| 20.2 | 4.40 | 17 |
| 22.0 | 4.04 | 19 |
| 22.5 | 3.96 | 32 |
| 22.9 | 3.89 | 14 |
| 23.7 | 3.75 | 25 |
| 26.7 | 3.34 | 9 |

TABLE X

XRPD of Example 10 (1,5-naphthalenedisulphonic acid salt - Form B)

| 2Ø (°) | d-spacing (Å) | Relative Intensity (%) |
|---|---|---|
| 3.4 | 26.34 | 11 |
| 6.6 | 13.41 | 100 |
| 8.3 | 10.70 | 9 |
| 9.0 | 9.88 | 12 |
| 10.5 | 8.40 | 10 |
| 11.8 | 7.51 | 6 |
| 12.0 | 7.39 | 8 |
| 12.2 | 7.24 | 6 |
| 13.2 | 6.73 | 8 |
| 14.1 | 6.30 | 13 |
| 14.5 | 6.13 | 38 |
| 15.6 | 5.69 | 14 |
| 16.5 | 5.37 | 17 |
| 17.7 | 5.00 | 20 |
| 18.8 | 4.72 | 10 |
| 20.3 | 4.37 | 30 |
| 21.1 | 4.21 | 31 |
| 21.9 | 4.06 | 13 |
| 24.1 | 3.70 | 12 |
| 24.4 | 3.64 | 10 |
| 28.5 | 3.14 | 9 |

TABLE XI

XRPD of Example 11 (Citric acid salt - Form A)

| 2Ø (°) | d-spacing (Å) | Relative Intensity (%) |
|---|---|---|
| 5.1 | 17.26 | 23 |
| 9.1 | 9.76 | 100 |
| 10.0 | 8.82 | 22 |
| 11.6 | 7.61 | 15 |
| 13.7 | 6.47 | 24 |
| 15.1 | 5.86 | 55 |
| 17.1 | 5.19 | 11 |
| 18.1 | 4.90 | 42 |
| 18.8 | 4.72 | 11 |
| 20.8 | 4.27 | 9 |
| 21.2 | 4.19 | 34 |
| 21.8 | 4.08 | 7 |
| 22.9 | 3.88 | 6 |
| 23.9 | 3.72 | 8 |
| 27.2 | 3.28 | 23 |

TABLE XII

XRPD of Example 12 (Citric acid salt - Form B)

| 2Ø (°) | d-spacing (Å) | Relative Intensity (%) |
|---|---|---|
| 5.3 | 16.82 | 100 |
| 9.3 | 9.53 | 5 |
| 12.4 | 7.13 | 2 |
| 12.9 | 6.85 | 2 |
| 13.9 | 6.37 | 9 |
| 15.5 | 5.73 | 2 |
| 16.6 | 5.35 | 1 |
| 18.0 | 4.92 | 2 |
| 18.5 | 4.79 | 4 |
| 19.5 | 4.56 | 3 |
| 19.9 | 4.47 | 3 |
| 21.5 | 4.14 | 2 |
| 22.9 | 3.88 | 2 |
| 24.4 | 3.65 | 2 |
| 24.9 | 3.57 | 3 |
| 25.3 | 3.52 | 4 |

TABLE XIII

XRPD of Example 13 (Phosphoric acid salt)

| 2Ø (°) | d-spacing (Å) | Relative Intensity (%) |
|---|---|---|
| 7.4 | 12.02 | 100 |
| 8.4 | 10.54 | 9 |
| 9.5 | 9.29 | 3 |
| 11.8 | 7.50 | 3 |
| 14.7 | 6.03 | 8 |
| 16.7 | 5.31 | 4 |
| 18.0 | 4.92 | 12 |
| 19.1 | 4.64 | 11 |
| 20.3 | 4.38 | 5 |
| 22.0 | 4.05 | 9 |
| 24.9 | 3.58 | 6 |

TABLE XIV

XRPD of Example 14 (Diphosphoric acid salt)

| 2Ø (°) | d-spacing (Å) | Relative Intensity (%) |
|---|---|---|
| 6.2 | 14.23 | 11 |
| 6.7 | 13.16 | 100 |
| 8.0 | 11.00 | 60 |
| 10.1 | 8.77 | 13 |
| 11.0 | 8.06 | 20 |
| 12.0 | 7.37 | 4 |

TABLE XIV-continued

| XRPD of Example 14 (Diphosphoric acid salt) | | |
|---|---|---|
| 2Ø (°) | d-spacing (Å) | Relative Intensity (%) |
| 12.6 | 7.01 | 23 |
| 13.4 | 6.60 | 33 |
| 14.5 | 6.10 | 5 |
| 15.3 | 5.78 | 8 |
| 16.0 | 5.55 | 3 |
| 17.0 | 5.20 | 5 |
| 18.3 | 4.85 | 32 |
| 19.2 | 4.62 | 6 |
| 20.2 | 4.40 | 18 |
| 21.1 | 4.21 | 7 |
| 21.5 | 4.13 | 11 |
| 22.5 | 3.95 | 25 |
| 24.1 | 3.68 | 14 |
| 24.8 | 3.58 | 3 |
| 25.4 | 3.51 | 4 |
| 27.0 | 3.29 | 3 |
| 28.0 | 3.19 | 4 |
| 29.3 | 3.05 | 2 |

TABLE XV

| XRPD of Example 15 (Fumaric acid salt) | | |
|---|---|---|
| 2Ø (°) | d-spacing (Å) | Relative Intensity (%) |
| 6.3 | 13.94 | 52 |
| 7.4 | 11.87 | 11 |
| 8.7 | 10.20 | 37 |
| 10.0 | 8.82 | 3 |
| 10.8 | 8.21 | 8 |
| 12.3 | 7.22 | 16 |
| 12.7 | 6.98 | 14 |
| 13.2 | 6.70 | 9 |
| 13.8 | 6.43 | 21 |
| 14.8 | 6.00 | 18 |
| 15.4 | 5.74 | 3 |
| 16.0 | 5.52 | 10 |
| 17.3 | 5.11 | 14 |
| 17.6 | 5.02 | 55 |
| 18.9 | 4.70 | 2 |
| 20.0 | 4.45 | 59 |
| 20.8 | 4.26 | 7 |
| 21.2 | 4.20 | 7 |
| 21.6 | 4.11 | 10 |
| 21.9 | 4.05 | 8 |
| 22.6 | 3.93 | 20 |
| 23.0 | 3.86 | 31 |
| 23.2 | 3.82 | 22 |
| 24.3 | 3.67 | 58 |
| 25.0 | 3.56 | 5 |
| 25.6 | 3.48 | 31 |
| 26.1 | 3.41 | 4 |
| 28.2 | 3.16 | 3 |
| 29.0 | 3.08 | 2 |

TABLE XVI

| XRPD of Example 16 (L-Tartaric acid salt) | | |
|---|---|---|
| 2Ø (°) | d-spacing (Å) | Relative Intensity (%) |
| 5.8 | 15.14 | 68 |
| 7.9 | 11.16 | 93 |
| 9.4 | 9.42 | 6 |
| 10.7 | 8.30 | 19 |
| 12.7 | 6.99 | 11 |
| 13.6 | 6.52 | 100 |
| 13.9 | 6.35 | 12 |
| 15.0 | 5.90 | 15 |
| 15.3 | 5.78 | 67 |
| 17.1 | 5.17 | 57 |

TABLE XVI-continued

| XRPD of Example 16 (L-Tartaric acid salt) | | |
|---|---|---|
| 2Ø (°) | d-spacing (Å) | Relative Intensity (%) |
| 18.2 | 4.87 | 28 |
| 18.9 | 4.70 | 47 |
| 19.4 | 4.57 | 16 |
| 20.6 | 4.31 | 25 |
| 21.5 | 4.13 | 78 |
| 21.7 | 4.09 | 46 |
| 22.4 | 3.98 | 10 |
| 22.7 | 3.91 | 11 |
| 23.0 | 3.87 | 9 |
| 23.3 | 3.81 | 6 |
| 23.9 | 3.73 | 13 |
| 24.5 | 3.64 | 40 |
| 25.1 | 3.54 | 20 |
| 26.1 | 3.41 | 3 |
| 26.8 | 3.33 | 8 |
| 27.4 | 3.25 | 5 |

TABLE XVII

| XRPD of Example 17 (Succinic acid salt) | | |
|---|---|---|
| 2Ø (°) | d-spacing (Å) | Relative Intensity (%) |
| 5.3 | 16.73 | 97 |
| 8.6 | 10.25 | 23 |
| 10.2 | 8.69 | 81 |
| 10.8 | 8.19 | 3 |
| 12.2 | 7.25 | 3 |
| 12.4 | 7.12 | 5 |
| 12.9 | 6.83 | 7 |
| 13.5 | 6.54 | 42 |
| 14.3 | 6.20 | 7 |
| 14.6 | 6.05 | 4 |
| 15.4 | 5.77 | 7 |
| 15.8 | 5.61 | 21 |
| 16.7 | 5.30 | 91 |
| 17.2 | 5.14 | 29 |
| 17.5 | 5.07 | 20 |
| 18.1 | 4.89 | 10 |
| 18.8 | 4.72 | 46 |
| 20.0 | 4.43 | 44 |
| 20.4 | 4.36 | 28 |
| 21.1 | 4.20 | 14 |
| 21.6 | 4.11 | 17 |
| 22.3 | 3.99 | 45 |
| 22.9 | 3.88 | 90 |
| 23.3 | 3.82 | 100 |
| 24.5 | 3.63 | 9 |
| 24.9 | 3.57 | 16 |
| 25.4 | 3.50 | 6 |
| 26.4 | 3.37 | 4 |
| 26.9 | 3.32 | 9 |
| 27.6 | 3.23 | 6 |
| 27.9 | 3.19 | 12 |
| 28.2 | 3.16 | 10 |
| 29.3 | 3.05 | 7 |

TABLE XVIII

| XRPD of Example 18 (Disuccinic acid salt) | | |
|---|---|---|
| 2Ø (°) | d-spacing (Å) | Relative Intensity (%) |
| 6.6 | 13.41 | 52 |
| 7.7 | 11.41 | 21 |
| 8.2 | 10.77 | 20 |
| 8.8 | 10.07 | 5 |
| 9.5 | 9.35 | 13 |
| 10.3 | 8.57 | 5 |
| 11.0 | 8.03 | 4 |
| 12.1 | 7.34 | 4 |

TABLE XVIII-continued

| XRPD of Example 18 (Disuccinic acid salt) | | |
|---|---|---|
| 2Ø (°) | d-spacing (Å) | Relative Intensity (%) |
| 12.9 | 6.86 | 7 |
| 13.3 | 6.65 | 5 |
| 14.0 | 6.32 | 12 |
| 14.3 | 6.18 | 9 |
| 14.9 | 5.96 | 4 |
| 15.6 | 5.69 | 40 |
| 16.4 | 5.42 | 12 |
| 16.8 | 5.27 | 21 |
| 17.7 | 4.99 | 48 |
| 18.9 | 4.70 | 14 |
| 19.6 | 4.53 | 33 |
| 21.1 | 4.21 | 50 |
| 21.7 | 4.08 | 12 |
| 22.2 | 4.01 | 11 |
| 23.1 | 3.85 | 100 |
| 24.2 | 3.67 | 27 |
| 26.1 | 3.41 | 8 |
| 26.5 | 3.37 | 8 |
| 26.9 | 3.31 | 6 |
| 27.5 | 3.24 | 4 |
| 28.7 | 3.10 | 7 |
| 30.9 | 2.89 | 13 |

TABLE XIX

| XRPD of Example 19 (Difumaric acid salt) | | |
|---|---|---|
| 2Ø (°) | d-spacing (Å) | Relative Intensity (%) |
| 6.3 | 14.01 | 3 |
| 7.8 | 11.38 | 11 |
| 9.1 | 9.68 | 23 |
| 10.2 | 8.66 | 17 |
| 10.4 | 8.51 | 14 |
| 11.1 | 7.96 | 6 |
| 11.6 | 7.63 | 9 |
| 12.0 | 7.37 | 5 |
| 13.2 | 6.72 | 3 |
| 14.2 | 6.23 | 34 |
| 14.7 | 6.03 | 52 |
| 15.2 | 5.81 | 9 |
| 15.4 | 5.76 | 13 |
| 15.8 | 5.62 | 52 |
| 15.9 | 5.56 | 21 |
| 17.4 | 5.09 | 31 |
| 18.7 | 4.74 | 37 |
| 19.0 | 4.68 | 40 |
| 19.5 | 4.55 | 22 |
| 19.9 | 4.47 | 37 |
| 20.4 | 4.35 | 85 |
| 21.2 | 4.20 | 25 |
| 21.4 | 4.15 | 8 |
| 21.7 | 4.08 | 35 |
| 23.1 | 3.83 | 100 |
| 23.4 | 3.80 | 71 |
| 24.1 | 3.69 | 34 |
| 24.4 | 3.65 | 24 |
| 24.7 | 3.60 | 51 |
| 25.3 | 3.51 | 38 |
| 25.8 | 3.46 | 78 |

Example 21

Dynamic Vapour Sorption (DVS)

DVS analysis was performed using an SMS Dynamic Vapour Sorption DVS-Advantage instrument. The solid sample (approximately 1-5 mg) was placed into a platinum sample holder and the weight of the sample was recorded during a dual cycle step method (40 to 90 to 0 to 90 to 0% relative humidity (RH), in steps of 10% RH).

The responses of the mono-fumaric acid salt and the difumaric acid salt (Examples 15 and 19) to changes in humidity were investigated using DVS. The hygroscopicity was calculated as the relative change in weight of the sample between 0% RH at the start of the second cycle and 80% RH during the increase of humidity in the second cycle.

The hygroscopicity of a sample is dependent on factors in addition to the inherent properties of the pure solid form itself, for example the purity and the crystallinity of the sample will have some impact on the result.

The difumaric acid salt of Compound (I) (Example 19) was found to be slightly hygroscopic (0.2 to 2% w/w moisture uptake at 80% Relative humidity) as illustrated in FIG. 22.

Figure 23:
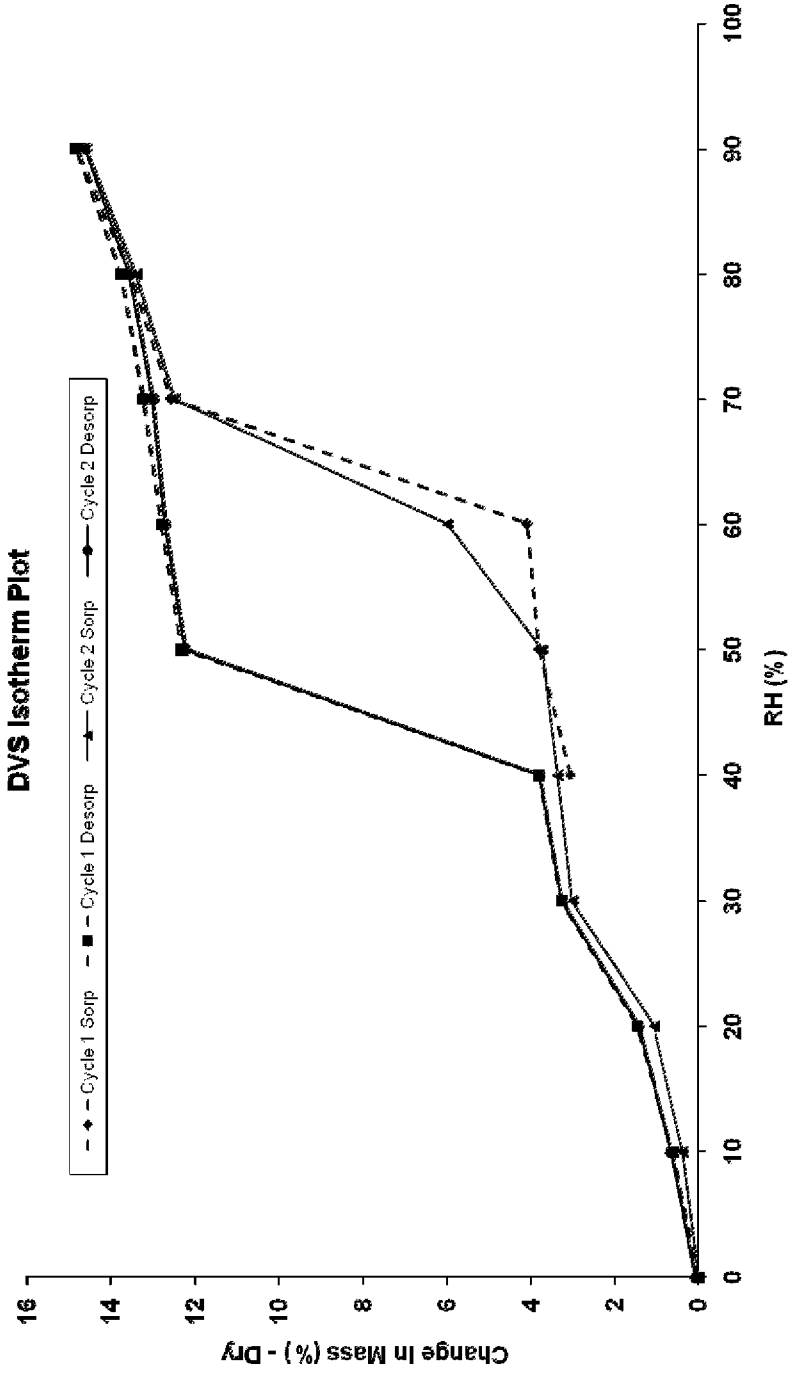
FIG. 23 shows a dynamic vapour sorption (DVS) isothermal plot for the mono-fumaric acid salt of Compound (I). The x-axis shows the relative humidity (RH %) and the y-axis shows the change in mass of the sample.

The mono-fumaric acid salt of Compound (I) (Example 15) was found to be hygroscopic (more than 2% w/w moisture uptake at 80% Relative humidity) as illustrated in FIG. 23.

Example 22

Salt Stability

The stability of the stability of the mono-saccharin (2 different batches), mono-trans-cinnamic acid, mono-succinic acid, mono-benzoic acid, difumaric acid, dixinafoic acid (di-1-hydroxy-2-naphthoic acid) and disaccharin salts of Compound (I) when stored at 40° C. and 75% relative humidity was measured as follows.

Approximately 30 mg of each salt was weighted into 4 mL screw cap vials, the vials closed and stored at 40° C./75% relative humidity with constant control of the environmental conditions. For every time point the samples were removed from the storage facility and analysed by HPLC for the presence of the acid degradation product of the Formula (A):

Formula (A)

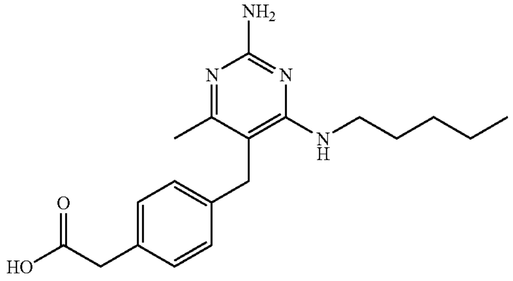

The HPLC analysis was performed using the following method:

A sample solution was prepared at approximately 0.1 to 0.2 mg/mL in the sample diluent, 0.03% trifluoroacetic acid in 50/50 v/v acetonitrile/water, using sonication as required. The following chromatographic conditions were applied:

| | | |
|---|---|---|
| Mobile phase: | A: 0.03% v/v trifluoroacetic acid aqueous<br>B: 0.03% v/v trifluoroacetic acid in acetonitrile | |
| Column: | Waters XBridge 50 × 4.6 mm internal diameter, 2.5 µm packing | |
| Column temperature: | 40° C. | |
| % B | Time | % B |
| | 0 | 5 |
| | 10 | 60 |
| | 10.1 | 5 |
| | 15 | 5 |

-continued

| | |
|---|---|
| Flow rate: | 0.7 mL/min. |
| Wavelength: | 220 nm |
| Injection volume: | 5 μL |
| Run time: | 15 min. |

Figure 24:
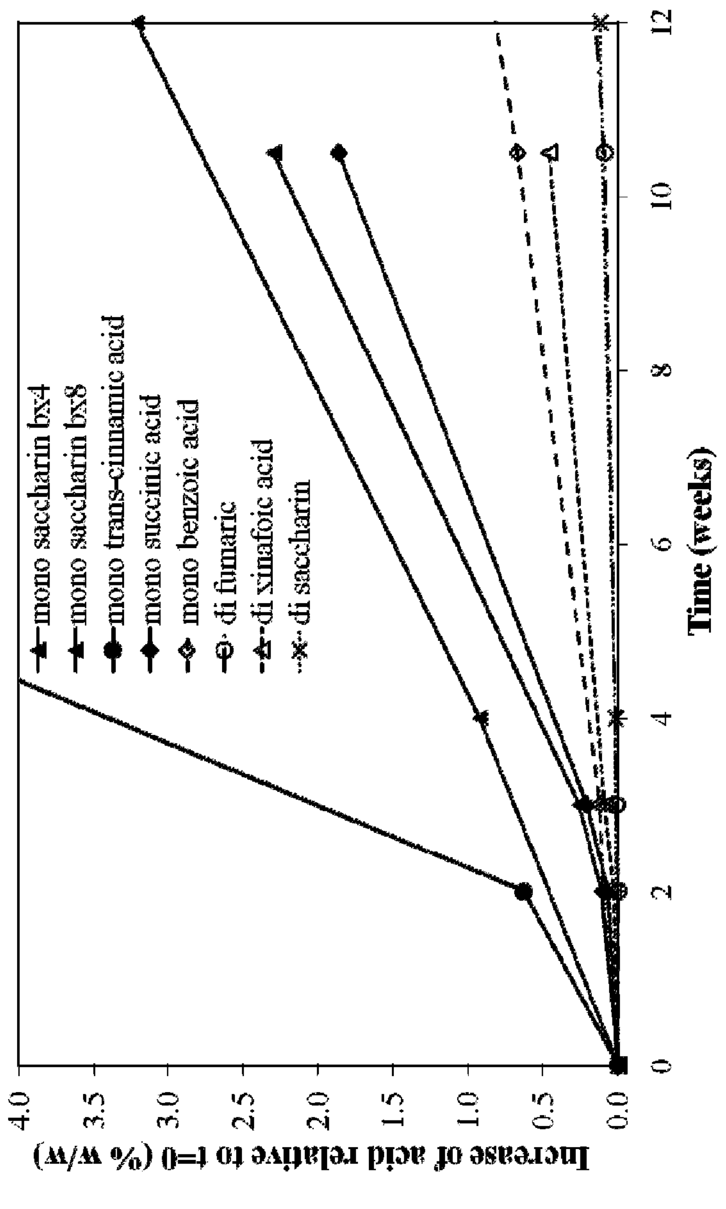
FIG. 24 shows the storage stability of the mono-saccharin (2 different batches, solid triangles), mono-trans-cinnamic acid (solid circles), mono-succinic acid (solid diamonds), mono-benzoic acid (open diamonds), difumaric acid (open circles), dixinafoic acid (open triangles) and disaccharin (crosses) salts of Compound (I) when stored at 40° C. and 75% relative humidity. The x-axis shows time (weeks) and the y-axis the % (w/w) of the acid degradation product of Formula (A) (described in Example 22).

The results of the stability study are shown in FIG. 24. The mono-saccharin salt of Compound (I) is described in Example 57 of WO2009/067081. As will be realised the dixinafoic acid salt in FIG. 24 is the di-1-hydroxy-2-naphthoic acid salt of Compound (I).

Example 23

Salt/Lactose Monohydrate Stability

The storage stability of blends of lactose monohydrate with the mono-saccharin, mono-benzoic acid, difumaric acid and disaccharin salts of Compound (I) when stored at is 40° C. and 75% relative humidity was measured as follows.

Approximately 5 grams of each salt were micronised using a 1" jet mill (MC One, Jetpharma, Balerna, Switzerland) with Nitrogen as the flow gas.

10 g of bulk lactose blend of each salt was prepared by the following method:

Micronised lactose monohydrate (9800 mg) was added to a 60 ml clear glass bottle. To this was added the micronised salt of compound (I) (200 mg) and a rubber stopper and aluminium screw cap used to close the bottle.

The bottle containing the salt and lactose monohydrate was placed in a trembling blender (Turbula T2C, W. Bachofen, Basel, Switzerland) blending vessel and the mixture blended for 10 minutes on speed 1 (30 rpm). A sample (2 g) of the lactose/salt blend was removed. The remaining of lactose/salt blend (8 g) was placed in a stability suite (controlled environmental conditions) at 40° C./75% relative humidity. The sample was temporarily removed from the storage facility for analysis. For each analysis 50 mg of the lactose/salt blend were dissolved in the sample diluents and analysed by HPLC for the compound of Formula (A) as described above in Example 23.

Figure 25:
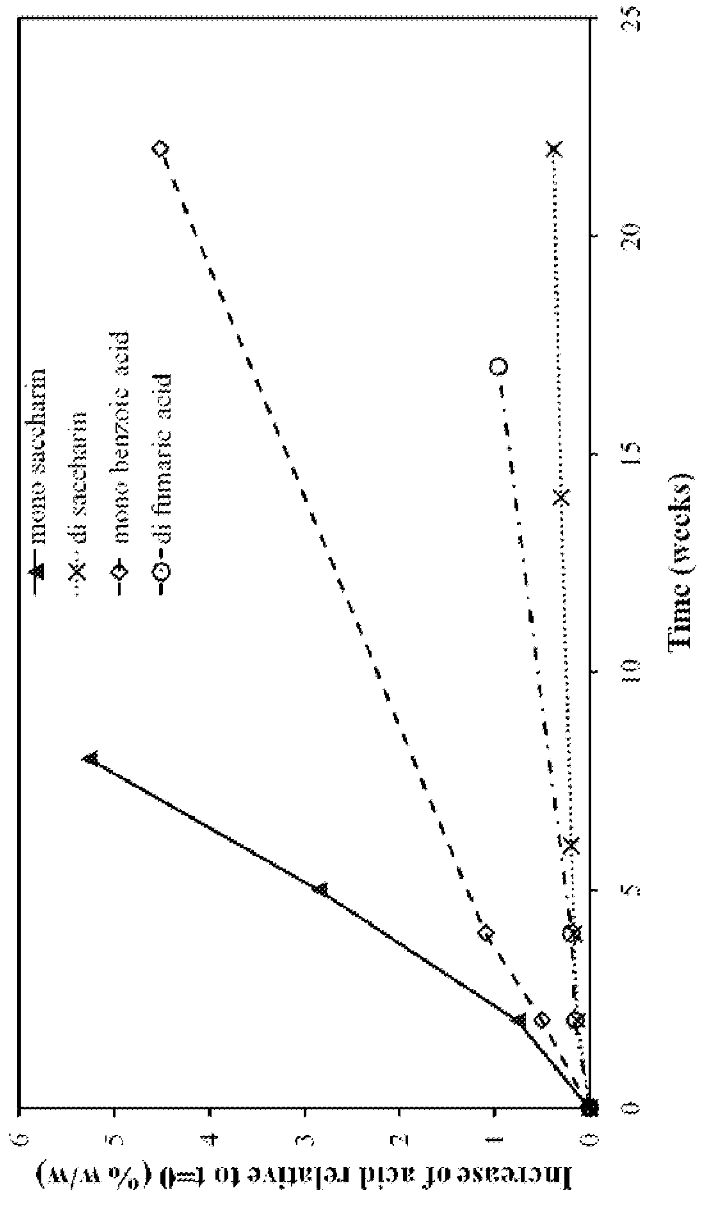
FIG. 25 shows the storage stability of blends of lactose monohydrate with the mono-saccharin (solid triangles), mono-benzoic acid (open diamonds), difumaric acid (open circles) and disaccharin (crosses) salts of Compound (I) when stored at 40° C. and 75% relative humidity. The x-axis shows time (weeks) and the y-axis the % (w/w) of the acid degradation product of Formula (A) (described in Example 22).

The results of the stability study on the lactose monohydrate/salt blends are shown in FIG. 25.

Biological Activity

Compound (I) and pharmaceutically acceptable salts thereof have antedrug properties. An antedrug is defined as an active synthetic derivative that is designed to undergo biotransformations to a readily excretable less active form upon entry into the systemic circulation, therefore minimizing systemic side-effects. Thus, on administration, a compound of the invention is rapidly degraded enzymatically to yield a, degradation product having a substantially reduced medical effect. A medical effect as defined herein means a pharmacological activity of the compound of the invention, including specifically interferon inducing activity and/or suppression of IL4/IL5 production activity. The medical effect of the degradation product is preferably 10 times, more preferably 100 times less than that of the compound of the invention (i.e. parent compound). The pharmacological activity can be measured using methods known in the art, suitably using in vitro evaluation methods such as commercially available ELISA kits or the human TLR7 assay described below.

Human TLR7 Assay

Recombinant human TLR7 was stably expressed in a HEK293 cell line already stably expressing the pNiFty2-SEAP reporter plasmid; integration of the reporter gene was maintained by selection with the antibiotic zeocin. The most common variant sequence of human TLR7 (represented by the EMBL sequence AF240467) was cloned into the mammalian cell expression vector pUNO and transfected into this reporter cell-line. Transfectants with stable expression were selected using the antibiotic blasticidin. In this reporter cell-line, expression of secreted alkaline phosphatase (SEAP) is controlled by an NFkB/ELAM-1 composite promoter comprising five NFkB sites combined with the proximal ELAM-1 promoter. TLR signaling leads to the translocation of NFkB and activation of the promoter results in expression of the SEAP gene. TLR7-specific activation was assessed by determining the level of SEAP produced following overnight incubation of the cells at 37° C. with the standard compound in the presence of 0.1% (v/v) dimethylsulfoxide (DMSO). Concentration dependent induction of SEAP production by compounds was expressed as the concentration of compound which produced half of the maximal level of SEAP induction for that compound (pEC50). Tests carried out using the disaccharin salt of Compound (I) (in amorphous form prior to dissolving in the DMSO) gave a mean pEC50 of 6.9 (n=8).

The invention claimed is:

1. Form A of 4-(dimethylamino)butyl 2-(4-((2-amino-4-methyl-6-(pentylamino)pyrimidin-5-yl)methyl)phenyl)acetate disaccharin salt, characterised in that said Form A has an X-ray powder diffraction pattern with specific peaks at 2θ about 9.2°, 13.9°, 14.9° or 15.2° when measured using CuKα radiation.

2. Form B of 4-(dimethylamino)butyl 2-(4-((2-amino-4-methyl-6-(pentylamino)pyrimidin-5-yl)methyl)phenyl)acetate disaccharin salt, characterised in that said Form B has an X-ray powder diffraction pattern with specific peaks at 2θ about=12.0°, 12.5°, 16.4° or 19.8° when measured using CuKα radiation.

3. 4-(Dimethylamino)butyl 2-(4-((2-amino-4-methyl-6-(pentylamino)pyrimidin-5-yl)methyl)phenyl)acetate difumaric acid salt, characterised in that said salt has an X-ray powder diffraction pattern with specific peaks at 2θ about =9.1°, 14.2°, 15.8° or 20.4° when measured using CuKα radiation.

4. 4-(Dimethylamino)butyl 2-(4-((2-amino-4-methyl-6-(pentylamino)pyrimidin-5-yl)methyl)phenyl)acetate di-1-hydroxy-2-naphthoic acid salt, characterised in that said salt has an X-ray powder diffraction pattern with specific peaks at 2θ about =8.3°, 16.6°, 19.4° or 23.4° when measured using CuKα radiation.

5. 4-(Dimethylamino)butyl 2-4-((2-amino-4-meth-6-(pentylamino)pyrimidin-5-yl)methyl)phenyl)acetate mono-benzoic acid salt, characterised in that said salt has an X-ray powder diffraction pattern with specific peaks at 2θ about =6.3°, 9.3°, 17.8° or 23.8° when measured using CuKα radiation.

6. A pharmaceutical composition comprising a salt as claimed in claim 1 in association with a pharmaceutically acceptable adjuvant, diluent or carrier.

7. The pharmaceutical composition according to claim 6, which is in a dry powder formulation suitable for inhalation therapy.

8. A dry powder inhaler containing a pharmaceutical composition as claimed in claim 7.

9. The pharmaceutical composition according to claim 7, comprising lactose monohydrate as a carrier.

10. The pharmaceutical composition according to claim 9, wherein the lactose monohydrate is in particle form, wherein the particles have a mass median diameter of 20-1000 μm.

11. Form A of 4-(dimethylamino)butyl 2-(4-((2-amino-4-methyl-6-(pentylamino)pyrimidin-5-yl)methyl)phenyl)acetate disaccharin salt according to claim 1, characterised in that said Form A has an X-ray powder diffraction pattern substantially as shown in FIG. 4 when measured using CuKα radiation.

12. Form B of 4-(dimethylamino)butyl 2-(4-((2-amino-4-methyl-6-(pentylamino)pyrimidin-5-yl)methyl)phenyl)acetate disaccharin salt according to claim 2, characterised in that said Form B has an X-ray powder diffraction pattern substantially as shown in FIG. 5 when measured using CuKα radiation.

13. 4-(Dimethylamino)butyl 2-(4-((2-amino-4-methyl-6-(pentylamino)pyrimidin-5-yl)methyl)phenyl)acetate difumaric acid salt according to claim 3, characterised in that said salt has an X-ray powder diffraction pattern substantially as shown in FIG. 19 when measured using CuKα radiation.

Figure 2:
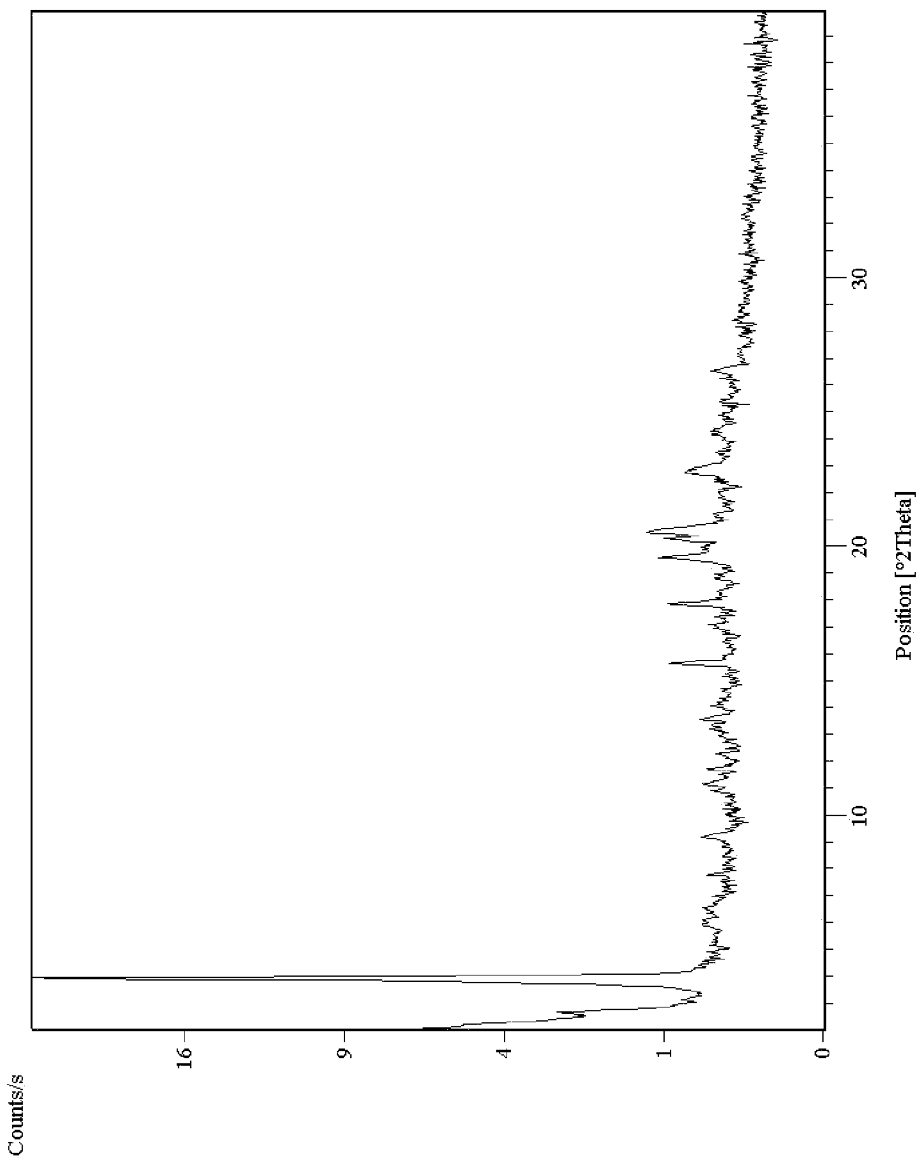
FIG. 2 shows an X-ray powder diffraction pattern of a mono trans-cinnamic acid salt of Compound (I).
Figure 3:
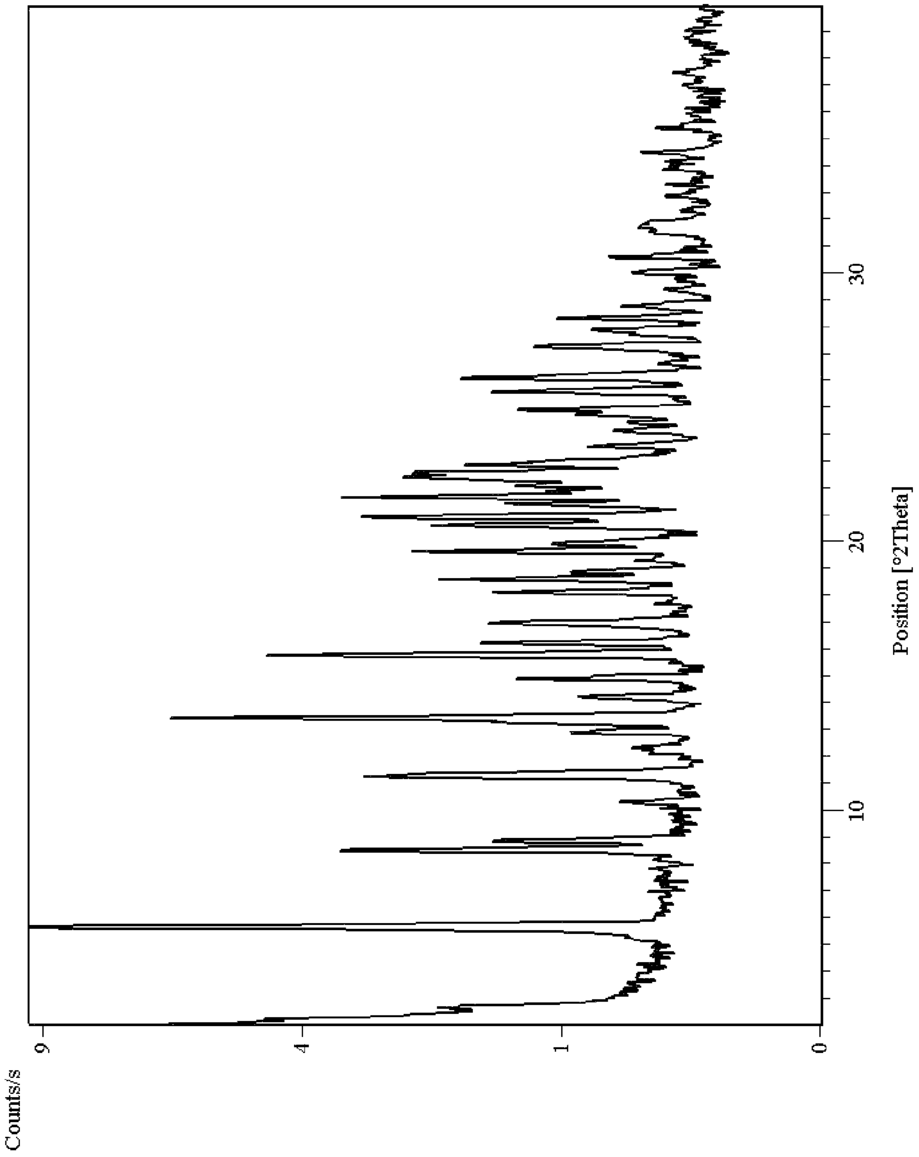
FIG. 3 shows an X-ray powder diffraction pattern of a mono-methanesulphonic acid salt of Compound (I).

14. 4-(Dimethylamino)butyl 2-(4-((2-amino-4-methyl-6-(pentylamino)pyrimidin-5-yl)methyl)phenyl)acetate di-1-hydroxy-2-naphthoic acid salt according to claim 4, characterised in that said salt has an X-ray powder diffraction pattern substantially as shown in FIG. 2 when measured using CuKα radiation.

15. 4-(Dimethylamino)butyl 2-(4-((2-amino-4-methyl-6-(pentylamino)pyrimidin-5-yl)methyl)phenyl)acetate monobenzoic acid salt according to claim 5, characterised in that said salt has an X-ray powder diffraction pattern substantially as shown in FIG. 1 when measured using CuKα radiation.

16. A pharmaceutical composition comprising a salt as claimed in claim 2 in association with a pharmaceutically acceptable adjuvant, diluent or carrier.

17. The pharmaceutical composition according to claim 16, which is in a dry powder formulation suitable for inhalation therapy.

18. A dry powder inhaler containing a pharmaceutical composition as claimed in claim 17.

19. The pharmaceutical composition according to claim 17, comprising lactose monohydrate as a carrier.

20. The pharmaceutical composition according to claim 19, wherein the lactose monohydrate is in particle form wherein the particles have a mass median diameter of 20-1000 μm.

21. A pharmaceutical composition comprising a salt as claimed in claim 3 in association with a pharmaceutically acceptable adjuvant, diluent or carrier.

22. The pharmaceutical composition according to claim 21, which is a dry powder formulation suitable for inhalation therapy.

23. A dry powder inhaler containing a pharmaceutical composition as claimed in claim 22.

24. The pharmaceutical composition according to claim 22, comprising lactose monohydrate as a carrier.

25. The pharmaceutical composition according to claim 24, wherein the lactose monohydrate is in particle form wherein the particles have a mass median diameter of 20-1000 μm.

26. A pharmaceutical composition comprising a salt as claimed in claim 4 in association with a pharmaceutically acceptable adjuvant, diluent or carrier.

27. The pharmaceutical composition according to claim 26, which is in a dry powder formulation suitable for inhalation therapy.

28. A dry powder inhaler containing a pharmaceutical composition as claimed in claim 27.

29. The pharmaceutical composition according to claim 27, comprising lactose monohydrate as a carrier.

30. The pharmaceutical composition according to claim 29, wherein the lactose monohydrate is in particle form wherein the particles have a mass median diameter of 20-1000 μm.

31. A pharmaceutical composition comprising a salt as claimed in claim 5 in association with a pharmaceutically acceptable adjuvant, diluent or carrier.

32. The pharmaceutical composition according to claim 31, which is in a dry powder formulation suitable for inhalation therapy.

33. A dry powder inhaler containing a pharmaceutical composition as claimed in claim 32.

34. The pharmaceutical composition according to claim 32, comprising lactose monohydrate as a carrier.

35. The pharmaceutical composition according to claim 34, wherein the lactose monohydrate is in particle form wherein the particles have a mass median diameter of 20-1000 μm.

* * * * *